US008691506B2

(12) United States Patent
Bausch et al.

(10) Patent No.: US 8,691,506 B2
(45) Date of Patent: Apr. 8, 2014

(54) GENE EXPRESSION PROFILES BEING PREDICTIVE FOR THE RESPONSE OF TUMORS TO PHARMACEUTICALLY EFFECTIVE COMPOUNDS

(75) Inventors: Niko Bausch, Freiburg (DE); Heinz-Herbert Fiebig, Freiburg (DE); André Korrat, Freiburg (DE); Martina Maurer, Freiburg (DE); Thomas Metz, Glottertal (DE); Julia Schüler, Freiburg (DE)

(73) Assignee: Oncotest GmbH, Freiburg (DE)

( * ) Notice: Subject to any disclaimer, the term of this patent is extended or adjusted under 35 U.S.C. 154(b) by 1758 days.

(21) Appl. No.: 11/911,222

(22) PCT Filed: Apr. 13, 2006

(86) PCT No.: PCT/EP2006/003421

§ 371 (c)(1),
(2), (4) Date: Dec. 11, 2007

(87) PCT Pub. No.: WO2006/108659

PCT Pub. Date: Oct. 19, 2006

(65) Prior Publication Data

US 2011/0243925 A1 Oct. 6, 2011

Related U.S. Application Data

(60) Provisional application No. 60/670,863, filed on Apr. 13, 2005.

(30) Foreign Application Priority Data

Apr. 13, 2005 (EP) .................................... 05008088

(51) Int. Cl.
*C12Q 1/68* (2006.01)
*C12P 21/06* (2006.01)

(52) U.S. Cl.
USPC ......................... 435/6.11; 435/69.1; 435/6.14

(58) Field of Classification Search
None
See application file for complete search history.

(56) References Cited

FOREIGN PATENT DOCUMENTS

| | | | |
|---|---|---|---|
| WO | 03/057916 | A2 | 7/2003 |
| WO | 2004/111603 | A2 | 12/2004 |

OTHER PUBLICATIONS

Zembutsu et al. IDS—Citation No. 2, Oct. 11, 2007.*
Zembutsu, H., et al., "Gene-expression profiles of human tumor xenografts in nude mice treated orally with the EGFR tyrosine kinase inhibitor ZD1839," International Journal of Oncology, 2003, 23(1):29-39.
Zembutsu, H., et al., "Genome-wide cDNA Microarray Screening to Correlate Gene Expression Profiles with Sensitivity of 85 Human Cancer Xenografts to Anticancer Drugs," Cancer Research, Jan. 15, 2002, 62:518-527.
Bergsland, E., et al., "Maximizing the Potential of Bevacizumab in Cancer Treatment," The Oncologist, 2004, 9(suppl 1):36-42.
Ghadimi, B.M., et al., "Effectiveness of Gene Expression Profiling for Response Prediction of Rectal Adenocarcinomas to Preoperative Chemoradiotherapy," Journal of Clinical Oncology, Mar. 20, 2005, 23(9):1826-1838.

* cited by examiner

*Primary Examiner* — Catherine Hibbert
(74) *Attorney, Agent, or Firm* — McDonnell Boehnen Hulbert & Berghoff LLP

(57) ABSTRACT

The present invention relates to a method for providing a gene expression profile being predictive for the specific response of an individual tumor to a pharmaceutically effective compound, the use thereof, a microarray wherein the nucleotide sequences attached to the substrate consist of nucleotide sequences corresponding to the predictive genes of said gene expression profile, and a diagnostic kit containing said microarray.

5 Claims, 2 Drawing Sheets

SEQUENCE LISTING

<160> NUMBER OF SEQ ID NOS: 118

<210> SEQ ID NO 1
<211> LENGTH: 462
<212> TYPE: DNA
<213> ORGANISM: Homo sapiens

<400> SEQUENCE: 1
ccattccagc tggagtcgtg gggctgggca caggggaatt tttccagagc tgagcctgac 60
gtctgctctg aagaatgctt agaaggttcc cagacaccag agccagatgt cccccaccac 120
cggtcaggac ctccttgagg tgcacaagca cggtctcctc tgagttcacc ccagcccacc 180
cccgcaccca ctaattctgc ttttcctgcc ccttgctccg taaaagtatc aaatactttc 240

-continued tccttggtat ctcaaggagg tttctgagat aggtagaagt cttgagacgg aggctggcca 300
tccattcagc cctgagcgtg ctgagttctg tgtttctctg aatagaggtg tggaacctga 360
ggggccagca ggcctctctg aaggcctcca tggagcaaac ggagccacct cgggaaagag 420
tttaatggaa tatttttgta cccgatgttt acagatgctg tt 462

<210> SEQ ID NO 2
<211> LENGTH: 471
<212> TYPE: DNA
<213> ORGANISM: Homo sapiens

<400> SEQUENCE: 2
agacctggtg ctctaatgcc aagttataca cgggacagtt gctggcatgt cttcattggc 60
tctctaaaat gtggccaaga agataggctc tcagtaagaa gtctgatggt gagcagtaac 120
tgtccctgct ttctggtata aagctctcaa atgtgaccat gtgaatctgg gtgggataat 180
ggactcagct ctgtctgctc aatgccattg tgcagagaag caccctaatg cataagcttt 240
ttaatgctgt aaaatatagt cgctgaaatt aaatgccact ttttcagagg tgaattaatg 300
gacagtctgg tgaacttcaa aagctttttg atgtataaaa cttgataaat ggaactattc 360
catcaatagg caaaagtgta acaacctatc tagatggata gtatgtaatt tctgcacagg 420
tctctgttta gtaaatacat cactgtatac cgatcaggaa tcttgctcca a 471

<210> SEQ ID NO 3
<211> LENGTH: 559
<212> TYPE: DNA
<213> ORGANISM: Homo sapiens

<400> SEQUENCE: 3
attttgtttt catctgtgat agtcatggat gcttttattt tccttggggt gctgaaattg 60
agctgaaaaa aaaaggctct ttgaatatag ttttaatttc tctctacagt tttttttgtt 120
tggtttgtgg gctgttggaa ttgtaatttt taattgcctt ctaaaaaatg gaaatttaac 180
aatgtctgat ctcagctgaa caaattagat gtttcagttg ctcttgggtc aactggctta 240
cagatttaca tgtgcacaca cacacaaatt tcttatcaca ttttcgactt cttcacttga 300
cctaactgat tatgcgaaat acccaagatt catgctactg taccacagat ttgttttcac 360
agcaataaat cttcagttct gttgtttatg attccactta acaaaaggcc tgcagaagtg 420
atttattatt tgggtatttg gagataatac atttgatggt tttttggaaa accttttca 480 ctccatactc agatatgctt cattgtcaaa tgcatattta gattagatta ttgaattgta 540
atgtttatct gctgctttt 559

<210> SEQ ID NO 4
<211> LENGTH: 379
<212> TYPE: DNA
<213> ORGANISM: Homo sapiens
<220> FEATURE:
<221> NAME/KEY: misc_feature
<222> LOCATION: (142)..(142)
<223> OTHER INFORMATION: n = g, c, a, or t

<400> SEQUENCE: 4
atccatttct tgcccttcaa taattgtcca tgcctgcctt ttgttgttta catgctcttc 60
tgcccagact gttagtaatc tagggacccc ctttggagct gataagtaca gttcagcctt 120
ttctcctcaa atatataatg anctttaaca ttcctaagaa tataggtatt tctgaatgat 180
ttaaatttga ggaattttaa tacataaaat acaatgtaca aactttctgc ccactcagat 240

-continued ctcttctcca tcatgtactt agtatttccc attaacctac acactgattt ttatgctact 300
ccttgtagaa acaaaattct ggtttgactc agtttttgtg tttataaact tttggaatgt 360
gtaccccgtt tatgtgaag 379

<210> SEQ ID NO 5
<211> LENGTH: 495
<212> TYPE: DNA
<213> ORGANISM: Homo sapiens

<400> SEQUENCE: 5
ggctcatgcg ggatttcaag cggttacaag aggacccacc tgtgggtgtc agtggcgcac 60
catctgaaaa caacatcatg cagtggaatg cagttatatt tggaccagaa gggacacctt 120
ttgaagatgg tacttttaaa ctagtaatag aattttctga agaatatcca aataaaccac 180
caactgttag gtttttatcc aaaatgtttc atccaaatgt gtatgctgat ggtagcatat 240
gtttagatat ccttcagaat cgatggagtc caacatatga tgtatcttct atcttaacat 300
caattcagtc tctgctggat gaaccgaatc ctaacagtcc agccaatagc caggcagcac 360
agctttatca ggaaaacaaa cgagaatatg agaaaagagt ttcggccatt gttgaacaaa 420
gctggaatga ttcataatag acaactggtc tgttaatctt tttcatcatt gttgtgtata 480
atttacctct catta 495

<210> SEQ ID NO 6
<211> LENGTH: 379
<212> TYPE: DNA
<213> ORGANISM: Homo sapiens

<400> SEQUENCE: 6
gtgacaacct cgtcaacaag ccagacgagc gcggcttcac ccccctcatc tgggcctccg 60
cctttggaga gattgagacc gttcgcttcc tgctggagtg ggtgccgac ccccacatcc 120 tggcaaaaga gcgagagagc gccctgtcgc tggccagcac aggcggctac acagacattg 180
tggggctgct gctggagcgt gacgtggaca tcaacatcta tgattggaat ggagggacgc 240
cactgctgta cgctgtgcgc gggaaccacg tgaaatgcgt tgaggccttg ctggcccgag 300
gcgctgacct caccaccgaa gccgactctg gctacacccc gatggacctt gccgtggccc 360
tgggataccg gaaagtgca 379

<210> SEQ ID NO 7
<211> LENGTH: 398
<212> TYPE: DNA
<213> ORGANISM: Homo sapiens

<400> SEQUENCE: 7
ggcaactcca gacctctggg aacaagactg cgggctctgc ccccagctct gccaggacgg 60
ctgcaagacc agctggcccg ggaggggaca acgggctgtt gcgggtgcgc ggcagctgga 120
gacactcccc cgcagggcca acccctgccc tgttgctctg ccctgcaggg gtcccggcgc 180
atggtcacct ggggtgcaca caggtcacac agtgccaaga ggccccaggg cccagggact 240
ccccccacag cagggtggga cccgggaccc gcggctcagt ggcccgctag ccacgtcagc 300
caagccactt taggtccatt ttttaatttt aacagtgctc ttccatcttg tgcataagcc 360
tgagatttgg aaagaataaa acaccgaatt gcagaaga 398

<210> SEQ ID NO 8
<211> LENGTH: 558

-continued

<212> TYPE: DNA
<213> ORGANISM: Homo sapiens

<400> SEQUENCE: 8

```
tgctccacct ttcagtgaca tttaagacat catattcccg taacattatg tctcagtctg     60

atcgtcttta ccagtatgaa agtcattcat ttagtgctac caaaggggat acacaagccc    120

tttaggaagc agtacctctc gcctggagga tctgtgccat cttggattga gaattgcaga    180

tgtgacagaa tggattgacc ctagttggtt ggtattgatg acttcagcct ggaaattgct    240

tgccttttaa agaagcatat atgggttgga attatgccaa agcataggaa gctgggaata    300

agcaaacaaa tgctgatata gtcagcaaat ttggatagtc tctagggctc atcatttttc    360

atactacctc tctcttctgg cctgtgtcta aggaattgta caacataggc cagggccaac    420

aaagtggaga ggtggacaca ttttcatgtt cattactaaa acaaacagca aaactattgg    480

tttgttattc tgtgttttcc tcaagtcagt acatactatt tggtttcagg atttctttcc    540

atttctctat caagcatt                                                   558
```

<210> SEQ ID NO 9
<211> LENGTH: 268
<212> TYPE: DNA
<213> ORGANISM: Homo sapiens

<400> SEQUENCE: 9

```
ttacatttga actatatcct tcctagtggg ttagtgtgaa aaagagtttg gctgattcct     60

aaaactctgc cagccctgca gtaatctcca ggcctggtta ttgttcagac attccatggt    120

gattcctggg aaggaagctt ggctgctcag tttctgagtc tggggtgaga taatgttctg    180

gaaggacatc tgttctttgg tgtaatctct catggtgaaa tctgctctgt acatcagaca    240

attgcattgc taccaagttt cataccaa                                        268
```

<210> SEQ ID NO 10
<211> LENGTH: 506
<212> TYPE: DNA
<213> ORGANISM: Homo sapiens

<400> SEQUENCE: 10

```
aatcagcatc tttccaatga ggtcaaaact tggaaggaaa gaacccttaa aagagaggct     60

cacaaacaag taacttgtga gaattctcca aagtctccta aagtgactgg aacagcttct    120

aaaaagaaac aaattacacc ctctcaatgc aaggaacgga atttacaaga tcctgtgcca    180

aaggaatcac caaaatcttg tttttttgat agccgatcaa agtctttacc atcacctcat    240

ccagttcgct attttgataa ctcaagttta ggcctttgtc cagaggtgca aaatgcagga    300

gcagagagtg tggattctca gccaggtcct tggcacgcct cctcaggcaa ggatgtgcct    360

gagtgcaaaa ctcagtagac tcctctttgt cacttctctg gagatccagc attccttatt    420

tggaaatgac tttgtttatg tgtctatccc tggtaatgat gttgtagtgc agcttaattt    480

caattcagtc tttactttgc cactag                                          506
```

<210> SEQ ID NO 11
<211> LENGTH: 461
<212> TYPE: DNA
<213> ORGANISM: Homo sapiens

<400> SEQUENCE: 11

```
acttcttctc tcatgaatca tccagtcatt ccaatggcaa ataagttctc acctaccctt     60

gagctgcaag gtgaattctc tccattacag tcatctttgc cttgtgacat tcatctggtt    120
```

-continued

```
aatttgagaa caatacagtc aaaggtgggc aatgggcact ccaatgaggc agccttgatc    180

ctccacagaa aagggtttga ttgtcggttc tctagcaaag gcacagggct gttttgttct    240

actactcagg gaaagatatt ggtacagaaa cttttaaaca agtttattgt cgaaagtctc    300

acaccttcat cactatcctt gatgcattca cctcccggca ctcagaatat aagtgagatc    360

aacttgagtc caatggaaat cagcacattc cgaatccagt tgaggtgaac ctgactttca    420

catttggatt gagaatcatt ggcttttata cctttcttgg t                        461
```

<210> SEQ ID NO 12
<211> LENGTH: 550
<212> TYPE: DNA
<213> ORGANISM: Homo sapiens

<400> SEQUENCE: 12

```
gaggagaaca ctagacatgc caactcggga gcattctgcc tgcctgggaa cggggtggac     60

gagggagtgt ctgtaaggac tcagtgttga ctgtaggcgc ccctggggtg ggtttagcag    120

gctgcagcag gcagaggagg agtacccccc tgagagcatg tgggggaagg ccttgctgtc    180

atgtgaatcc ctcaataccc ctagtatctg gctgggtttt caggggcttt ggaagctctg    240

ttgcaggtgt ccgggggtct aggactttag ggatctggga tctggggaag gaccaaccca    300

tgccctgcca agcctggagc ccctgtgttg gggggcaagg tgggggagcc tggagcccct    360

gtgtgggagg gcgaggcggg ggagcctgga gcccctgtgt gggagggcga ggcgggggat    420

cctggagccc ctgtgtcggg gggcgaggga ggggaggtgg ccgtcggttg accttctgaa    480

catgagtgtc aactccagga cttgcttcca agcccttccc tctgttggaa attgggtgtg    540

ccctggctcc                                                           550
```

<210> SEQ ID NO 13
<211> LENGTH: 549
<212> TYPE: DNA
<213> ORGANISM: Homo sapiens

<400> SEQUENCE: 13

```
ctttttcttc taagcctgtg tgttataatt taccagttcc ccaaaatgcc atttttaacg     60

ccgaactgtg taatatacat ggaaaacagc tttttacaat taattttcaa agttgtaatt    120

ttaaagaatt tgggtgtata cctatgttaa tgaaacaaca gaagtacaaa aaagaatatc    180

agatacaaaa atcaatcgtg aagaaaatct gttcttaata tatttcatta tgattgaaaa    240

acataaaaac taacatagga aagtgaatga tcagttactt atgatatatt ttgtttcctc    300

ttgtggttta ataaagtgaa gtgtgtgtgt gtgtgtgtgt gtgtgtgtgt gtgtatacct    360

gggggtgggc agtgctcttt ttctaaaact aatatggctt atatatctga attatgccct    420

ttttagtgtg tattaggatg tgggctggtt tgcttttcta ccacctttgt aattttatgt    480

atcccatctc ctttgtgtga attcatatat tatagcaaaa tacaagagac atgggactgt    540

ttgcaatac                                                            549
```

<210> SEQ ID NO 14
<211> LENGTH: 523
<212> TYPE: DNA
<213> ORGANISM: Homo sapiens

<400> SEQUENCE: 14

```
tacgccctcg acaggatgca gtttggtgtc ccactggcca ggaaccagct gattcagaag     60

aagctggcag acatgctcac tgagattacc ctgggccttc acgcctgcct gcagctcggc    120
```

-continued cgcttgaagg accaggacaa ggctgccccc gagatggttt ctctgctgaa gaggaataac 180
tgtgggaaag ccctggacat cgcccgccag gcccgagaca tgctgggggg gaatgggatt 240
tctgacgagt atcacgtgat ccggcacgcc atgaacctgg aggccgtgaa cacctacgaa 300
gtcgttcaga tgtgttcctt aaaaagaaga tggaattctc tgtagagcgt ctcaatccac 360
ttttaaccat ggatgagagc agactccatt taccctgaaa tagcagcttc tcttgagagg 420
agagtgacat ggaagcaact ccgtctgctg cagctgaccc cctcacactg agttcacagt 480
gcgccctccc tccctcccat ctgggggtag tgccttatgc tgg 523

<210> SEQ ID NO 15
<211> LENGTH: 466
<212> TYPE: DNA
<213> ORGANISM: Homo sapiens

<400> SEQUENCE: 15
gttggttgtg actgtactat tctagtatag tgaactacat actgaatatc caagttctca 60
gcacctactt ttgtcaaatc ttaacatttt gccacttcga gatcacattg ccttcctccc 120
ctccaagagg taacaattat ccacaatttg atgtttatca ttcctgtgtt gttgtacttt 180
cactgtgtat aacctaaacc atctactctt tagtactgtt ttatatattt ttaagcctca 240
tacttgctca ttctacagct tttttcactc attattgtat aattatatct gaagctctcg 300
ttcattaatt ttagtcctgt gtagcagaat tcaattacgg gaaactacca taatttatct 360
gttctccagt ccagttgaag gcatgaagtt gttgccagtt tctgtattat aacactgtag 420
tggaacattc ttctgcattg ggctactcgc gtgttaccta agacgt 466

<210> SEQ ID NO 16
<211> LENGTH: 143
<212> TYPE: DNA
<213> ORGANISM: Homo sapiens

<400> SEQUENCE: 16
gtggcacagt ggtctatggg ggcaaggtta tggatcgccc tggaaattat gtagaaccga 60
caattgtgac aggtcttggc cacgatgcgt ccattgcaca cacagagact tttgctccga 120
ttctctatgt ctttaaattc cag 143

<210> SEQ ID NO 17
<211> LENGTH: 486
<212> TYPE: DNA
<213> ORGANISM: Homo sapiens

<400> SEQUENCE: 17
tgttcgaatg ccttatagcc ttcctcacag cacccaggat tgtgactgac tctgcatttt 60
taattcttga aacttggctt tccataacat ggtacatgct tcaggactac atatgaccca 120
gagagcaagg tggctgaact atagtctgga agccctcagg taaagaggca catctcacca 180
ctcattggtt aaacaatgca tcatagcgag cacttttcct ttccctggag aatgggatgt 240
gaagcagtag accgcagcca cgccgatggt tatacagtga agaagacttc acctcttcct 300
attgagtttg cttggaatgc tgacagcatc aggcaactct gaactgaaca tttgctttgt 360
cagaaaatat cttttttttt actttgaagt ttggcaacct tcatgttacc ccaaagcaaa 420
accattgtgt caggagtcaa acaaatgttt agaaagcaaa catgacgtct ctattgtaca 480
acctcc 486

-continued

<210> SEQ ID NO 18
<211> LENGTH: 513
<212> TYPE: DNA
<213> ORGANISM: Homo sapiens

<400> SEQUENCE: 18
taatctggtg aatgatcccg ctacagatga aacagttttg gctgttttgg ctgatattgc 60
accttccaca gatgacttgg cctccctcag tgaaaaaaat accactgcag agtgctggga 120
tgagaaattt acctgcacaa ggctctactc tgtgcatcgg ccggttaaac aatgcattca 180
tcagttatgc ttcaccagtt tacgacgtat gtacatcgtc aacaaggaga tctgctctcg 240
tcttgtctgt aaggaacacg aagctatgaa agatgagctt tgccgtcaga tggctggtct 300
gccccctagg agactccgtc gctccaatta cttccgactt cctccctgtg aaaatgtgga 360
tttgcagaga cccaatggtc tgtgatcatt gaaaaagagg aaagaagaaa aaatgtatgg 420
gtgagaggaa ggaggatctc cttcttctcc aaccattgac agctaaccct tagacagtat 480
ttcttaaacc aatccttttg caatgtccag ctt 513

<210> SEQ ID NO 19
<211> LENGTH: 470
<212> TYPE: DNA
<213> ORGANISM: Homo sapiens

<400> SEQUENCE: 19
gagagagtat gctctgtgtc gtcccagaca tttctgcatt ccgagaaggt tggagatggg 60
tccggcaacc agtccaggtt ccagtaactt tggtccgaaa tgatggaatc atttattcca 120
ccagccttac ctttacctac acaccagaac cagggccgcg gccacattgc agtgcagcag 180
gagcaatcct tcgagccaat tcaagccagg tgccccctaa cgaatcaaac acaaacagcg 240
agggaagtta cacaaacgcc agcacaaatt caaccagtgt cacatcatct acagccacag 300
tggtatccta actaccgtct ttttgctagg acttaaactg acttgagtgt ggcaaaaagt 360
taacaaaaaa ggagaaaaaa tgaacaatcg tttgtggttt cttgggaaaa cttttcatac 420
caggtgatac tattcaaaaa ccccgttgtc tccctgcaag tgctgatttg 470

<210> SEQ ID NO 20
<211> LENGTH: 509
<212> TYPE: DNA
<213> ORGANISM: Homo sapiens
<220> FEATURE:
<221> NAME/KEY: misc_feature
<222> LOCATION: (157)..(222)
<223> OTHER INFORMATION: n = g, c, a, or t

<400> SEQUENCE: 20
tgtcttcaca gcgtccctaa ggaagatttt tgcagcactc tctggagctg aggggagtga 60
aatttggtcc agagaaggcg gaaggaaata gttttcctgt ttccttttct cgaggtggat 120
gtcctcaggc ttccttcaca cctccttctc atgggtncgg ntggcagtac agtcaggctg 180
tggaggaggg ctgagaagaa aggggcactg gtccagcccc anggtttggt ctgagacagg 240
tacacagcag ataccatccc accttcctct ctaaagaaca ggccagccac acatataacc 300
ctttccctac tttactaatg tatcccttat gtggtaccag caatggagga caggcagact 360
taccccctgc catctagaga gaatgttgtt attacccgta aaacttgacc acccccatat 420
cccactcctt tttgtaaaaa caaatgctta aacctgtgag cctgccgttc ctttctatgt 480
gttaatcagt ttccttccat ttgagctgt 509

<210> SEQ ID NO 21
<211> LENGTH: 528
<212> TYPE: DNA
<213> ORGANISM: Homo sapiens
<220> FEATURE:
<221> NAME/KEY: misc_feature
<222> LOCATION: (126)..(193)
<223> OTHER INFORMATION: n = g, c, a, or t

<400> SEQUENCE: 21
gcacctggcc cataaattgt catactttta aagagcctat tacacaaagt atcatcagaa 60
tcatcccaag actcatttcc tgattcctaa ttatttaaaa ttttgctttt aggcgaggca 120
tggtgnctca agcctatnnt cccagcactt tgggagncna aggcaggcag atcatttgag 180
gtcaggagtt tnngaccagc ctggccaaca tggtgaaacc tgaaacccca tctctaccaa 240
aaaaatggaa aaatttagcc aggtgtggtg gtgcatgcct gtaatcccag cctcccgagt 300
agctggggct caggcgtgcg ccaccatgcc cggctaattt ttgtatattt atggaaatgc 360
caagagatag ttcaatctgc ctctctggca agccatggac accaggtctg acaaactctc 420
ttactcctta agacaaatgc tcacctgatc aatatgggga aataagctgc atggtaccat 480
aatttctatt ctaaaaggga aaagtatctc tttggtattg ctttggaa 528

<210> SEQ ID NO 22
<211> LENGTH: 523
<212> TYPE: DNA
<213> ORGANISM: Homo sapiens

<400> SEQUENCE: 22
gatcaactta cctgtctgat cctcgtctta cagcgaatgg tttcaagata aaattgatac 60
caggagtttc aattactgaa aattacttgg aaatagaagg aatggctaat tgtctcccat 120
tctatggagt agcagattta aaagaaattc ttaatgctat attaaacaga aatgcaaagg 180
aagtttatga atgtagacct cgcaaagtga taagttattt agagggagaa gcagtgcgtc 240
tatccagaca attacccatg tacttatcaa aagaggacat ccaagacatt atctacagaa 300
tgaagcacca gtttggaaat gaaattaaag agtgtgttca tggtcgccca ttttttcatc 360
atttaaccta tcttccagaa actacatgat taaatatgtt taagaagatt agttaccatt 420
gaaattggtt ctgtcataaa acagcatgag tctggtttta aattatcttt gtattatgtg 480
tcacatggtt attttttaaa tgaggattca ctgacttgtt ttt 523

<210> SEQ ID NO 23
<211> LENGTH: 477
<212> TYPE: DNA
<213> ORGANISM: Homo sapiens
<220> FEATURE:
<221> NAME/KEY: misc_feature
<222> LOCATION: (33)..(75)
<223> OTHER INFORMATION: n = g, c, a, or t

<400> SEQUENCE: 23
gacatgtctt ccaagagtgc caattactgc ttnnnnnnnc gcctaaagna tacaggactg 60
ctgctcttat cagnngtagc tctaggtcag tgtaatgaac tactagaggc caatcctaag 120
gccgaaggat tgcttcaagg taaacatagc accaaggggc tgggcaagat ggctcccagt 180
tctgcccact tcgtcaccct gtaagtactc agaaccagga ggactagaag actccttttg 240
gccagataag actacgttct ctattgcagc ttctgaacca gagactgatg ttgacacact 300
ttttttccat ttggcaggaa tgggagtaca gtgccattag gaccagcaag tgacacagga 360
attctgaatc cagatggtta taccctcaac tacaatgaat atattgtata taaccccaac 420
caggtccgta tgcggtacct tttaaaggtt cagtttaatt tccttcagct gtggtga 477

<210> SEQ ID NO 24
<211> LENGTH: 544
<212> TYPE: DNA
<213> ORGANISM: Homo sapiens

<400> SEQUENCE: 24
ttctgatgtg ccagaaaccg ccctgagatc tgccggtcat ctccatggac ttctgcaccc 60
cattccatac ccttcttcac ctggggtacc ccttccagtt ttccccttgc ttcccaggcc 120
cttgacatgg cttacctgcc ttcactccca gcaccttgcc caacaggata agctggatcc 180
ccttggcctt ctgaatatcc cagtgtcttc aggtttccca agaccacttc cctgtgggct 240
tccaaaatgg cctttatcat ttctccagtc tgtcaccctc ctttcctgct cccatacacc 300
caaggcttgt ttcttcccct gtaaaaacca ctgcctcaat ctctggttca ctcaactagt 360
caccatgtcc tgaggcatga agcctcctca gctcttggaa ttgctggcaa ggggtgactg 420
cctctgagtc attgtgtttt tcaaagtgat ttcttttctg tagctttttg acctaagatc 480
tcagcaattt gaacactaac ctctcccctc ctggctcaag aattactccg aagtcagtct 540
gcag 544

<210> SEQ ID NO 25
<211> LENGTH: 536
<212> TYPE: DNA
<213> ORGANISM: Homo sapiens
<220> FEATURE:
<221> NAME/KEY: misc_feature
<222> LOCATION: (330)..(330)
<223> OTHER INFORMATION: n = g, c, a, or t

<400> SEQUENCE: 25
tgaagcatcc accagcactt caaggggtcc atagtatttt ttttttgct gcctcaaagt 60 ccccaaagcc ttcgagcaga agtggcagta gatggttgcc aatcagccaa tgcagacttt 120
cactgggaca acaagaaagc agatcttctg ggttttgatg gaacttggca gtggggacat 180
tcagctgatg cattatatac cccgtcagag cacacttgta tcttttacct tccctttgcc 240
ccatgccccc aaactgctta ggtcttctct gtccctttac tgctgctgca cagagatgat 300
ataaaagagg ctctttggct atttgcattn tgcttcctct tcttttccag attacagtat 360
gaagctttat tttctttgta caagcttaaa atttcaacat catcatccgc caaagttgtt 420
cctccctttt cggaggatct agggggaaag aggagcattc atcacaagtt tcctagagag 480
aggagacaaa tcggtgtgcc attgacaaca tgagccaggg taaaggcacc ctttgg 536

<210> SEQ ID NO 26
<211> LENGTH: 542
<212> TYPE: DNA
<213> ORGANISM: Homo sapiens
<220> FEATURE:
<221> NAME/KEY: misc_feature
<222> LOCATION: (499)..(507)
<223> OTHER INFORMATION: n = g, c, a, or t

<400> SEQUENCE: 26
gtcctggcta attgtgtggt cattggaaaa ctctgcaata caataatttt ctttattttc 60
tttttctttt ttaaattctt agtgtaattg aaacgtgctc tatagatatt gactctgtgt 120
tccctctttt acagctggac agaaagaagt caatgtcacg aaatgatttt ctattgtaga 180
tactttgtcc cttgcacttc tctgaatctg tccttttgtg gattcttgtg attttccttc 240

-continued caagtgtttc agttgtatga cagtcagtat tgacaataaa atggctttta attatttgtt 300
atttgtttac accctattcc tcagttatta ttactgtggt tctgattaac tactggaaat 360
tatatttgat tatatcacca attagttaaa tcagtgcttc gactcactct tatctgttct 420
gttcaaaact atttgttcaa agaacccgtt agtgttgttt acagggttac agtttctctc 480
acatgctttc ctcaccccnt taccccnctt tttgaaagcc tttattttgt tcggagtctc 540
tt 542

<210> SEQ ID NO 27
<211> LENGTH: 486
<212> TYPE: DNA
<213> ORGANISM: Homo sapiens

<400> SEQUENCE: 27
atgcctgacg gatcatttca aacctttgtg ggccaggaat gtgcccaaat ttggactagc 60
tcatctcatg gctctggggc tgggtccatg gctggcagtg gaaatccctg atctgattca 120
gaagggcgtc atccaccaca aagagaaatg caaccaatga agaatcaagc cactgaggca 180
gggcagaggg acctttgata ggctacgata ctattttcct gtgcatcaca cttaactcat 240
ctaactgctt ccccggacac cctccacctc tagttgttac taagtagctg cagtaggcat 300
tgctggggaa gaaacaaaca cacaccaaac agtactgcta cttagtttct aaggctgcac 360
agggaaggga aagactgggc tttggacaat ctagaggtaa tttatatccg cccccaggtg 420
gagcaacatg cgattctgga ggcacggggg taactgaaag tgagtacata tagtctttct 480
ggtttc 486

<210> SEQ ID NO 28
<211> LENGTH: 436
<212> TYPE: DNA
<213> ORGANISM: Homo sapiens

<400> SEQUENCE: 28
catagctgct ggaatcacac ctgagaactg agatatacca atatttaaca ttgttacaaa 60
gaagaaaaga tacagatttg gtgaatttgt tactgtgagg tacagtcagt acacagctga 120
cttatgtaga tttaagctgc taatatgcta cttaaccatc tattaatgca ccattaaagg 180
cttagcattt aagtagcaac attgcggttt tcagacacat ggtgaggtcc atggctcttg 240
tcatcaggat aagcctgcac acctagagtg tcggtgagct gacctcacga tgctgtcctc 300
gtgcgattgc cctctcctgc tgctggactt ctgcctttgt tggcctgatg tgctgctgtg 360
atgctggtcc ttcatcttag gtgttcatgc agttctaaca cagttggggt tgggtcaata 420
gtttcccaat ttcagg 436

<210> SEQ ID NO 29
<211> LENGTH: 319
<212> TYPE: DNA
<213> ORGANISM: Homo sapiens

<400> SEQUENCE: 29
attcaagaga gatgtccacg gccgaaacat acggtgaata attcacgctc acgtcgttct 60
tccacagtat cttgttttga tcatttccac tgcacatttc tcctcaagaa aagcgaaagg 120
acagactgtt ggctttgtgt ttggaggata ggagggagag agggaagggg ctgaggaaat 180
ctctggggta agagtaaagg cttccagaag acatgctgct atggtcactg aggggttagc 240
tttatctgct gttgttgatg catccgtcca agttcactgc ctttattttc cctcctccct 300
cttgttttag ctgttacac 319

<210> SEQ ID NO 30
<211> LENGTH: 544
<212> TYPE: DNA
<213> ORGANISM: Homo sapiens

<400> SEQUENCE: 30
ttggatgccc taactgctga tgtgaaggag aaaatgtata acgtcttgtt gtttgttgat 60
ggagggtgga tggtggatgt tagagaggat gccaaagaag accatgaaag aacacatcaa 120
atggtcttac tgagaaagct ttgtctgcca atgttgtgtt ttctgcttca tacgatattg 180
cacagtactg gtcagtatca ggaatgccta cagttagcag atatggtatc ctctgagcgc 240
cacaaactgt acctggtatt ttctaaggaa gagctaagga agttgctgca gaagctcaga 300
gagtcctctc taatgctcct agaccaggga cttgacccat tagggtatga aattcagtta 360
tagtttaatc tttgtaatct cactaatttt catgataaat gaagttttta ataaaatata 420
cttgttatta gtaatttttt cttttgcatt accatgtaaa atttagacat ttgaattttg 480
tacttttcag aatattatcg tgacactttc aacatgtagg gatatcagcg tttctctgtg 540
tgct 544

<210> SEQ ID NO 31
<211> LENGTH: 548
<212> TYPE: DNA
<213> ORGANISM: Homo sapiens
<220> FEATURE:
<221> NAME/KEY: misc_feature
<222> LOCATION: (510)..(510)
<223> OTHER INFORMATION: n = g, c, a, or t

<400> SEQUENCE: 31
ttttctaaac cacctctggg actcagctcc ccccgccaaa aaaaatgggt ctccttctgg 60
gctccaggat tgtctcccca ctccagcatc cccaaactgg tactccctga cccaggcccc 120
caatcctggg ctcttacaga gcatccatga gtcaagcccc ctccccacac ctggactcca 180
gaattcaccc tctcccctgc agtctgggtt cccagactga gtcctctccc caaatcaggg 240
ctctagaccc gagccctcca aacctggact ctgggactta ggccccctta aatctagact 300
tctctttata ggtttcaggt ctcctatggg tgcctgggaa gtccttgaaa gtggactgtt 360
ctcaggcttg acctgcccca ccccatcccc gcggttgagg ctgtgggggc agcagatcag 420
gagcccactg ataaggggcc ctagggtaca gggtgctgcc cagcaggtcg ccaccgagtg 480
tcttctcatt ttatttcagc tccattttgn ccatagatgg gcagaggggt gagattggct 540
catccccc 548

<210> SEQ ID NO 32
<211> LENGTH: 424
<212> TYPE: DNA
<213> ORGANISM: Homo sapiens

<400> SEQUENCE: 32
cagtcttcta taatgtgcct accaaaaagc ctagtcctag cccatctgcc tcaactcctc 60 tccctttag gttgtaggga agaggccgga gtgtagagta tattatatct tctgtccccc 120
ttatgccaac aagatggcct tcccctctga aacaaagtaa aactgcaaca ctgtgacttc 180
ttaaatgagg gatatgtgaa aaggctatga aaaatacaaa ggctttccta ggaaatgtgt 240
tataatgcag cgggaagcta attcttgaaa tatgcacatt atagttactc agtctcacat 300
actctagtta ctggcaaaga agttactgag aatatgtcat tcaaaggcat aggggccttt 360
gaatggaaca aatgctttca catcatttaa agtaaaaaaa aacctccaac aactgtgaat 420
ttat 424

<210> SEQ ID NO 33
<211> LENGTH: 458
<212> TYPE: DNA
<213> ORGANISM: Homo sapiens

<400> SEQUENCE: 33
ataatatccc ccagtatttt ccatattaaa tgctaattat cttttgattt ctttttcata 60
agcagatctg gcatttatta cagggctgcc gcttaagaga actcattata atgaacgttt 120
attatatttt gcagttccat gcctgttgtc cattgattga catgagcacc cctgttttct 180
ctggagaaat acctcccctc tctggggtgc ttcctgtggt agtgtctttc aggtatccgt 240
tccactagct acaggtgagc attttaccca ttgttggata atggtaatct ctttttcaga 300
attttgagtc tgtaattcat ttgtacatga accagaaaat gtgggaactc attcattctt 360
gtcccagaat tctgttgaga acatccattc attctggcta attgattaca agaataactg 420
tggatacgat ccctttagaa cctgcttctc tgatctgt 458

<210> SEQ ID NO 34
<211> LENGTH: 452
<212> TYPE: DNA
<213> ORGANISM: Homo sapiens

<400> SEQUENCE: 34
ggatcagctc aagaccatgg gttggagaat taatgttcac acttctattt ggagactttg 60
aatcccctct acacaagcta cgcaagtcaa gttagttgcc aagaaagcac agatgacaac 120
ctattaatgc tgtgagaatg tttctagatc agtgcatgga tggctccatt gctctacggg 180
ccattgtgtc tgagatccca gtctttgagg agaaaaaaaa caatggttaa aaaggcattg 240
gggaaatatt ttgagtttgg gggtgtactt tgccacccca ttattgggga gctgtcacca 300
cgaatgttcc caaacttagc aacagcggca aactactggg ccaagatgag caaccccaca 360
tttttgggat ttaaagctcc tgatgttata ccaggatcaa ccatcacact ccctttgctt 420
caaatggcgt ctaccccgta agatcttgag gg 452

<210> SEQ ID NO 35
<211> LENGTH: 340
<212> TYPE: DNA
<213> ORGANISM: Homo sapiens

<400> SEQUENCE: 35
caggaaggaa gggcgcagcg tcccctcctt cagaggaggc tctgggtggg gcctgctccc 60
catcccccca agcccaccca gcactctcat tgctgctgtt gagttcagct tttaccagcc 120
tcagtgtgga ggctccatcc cagcacacag gcctggggct tggcaggggc ccagctgggg 180
ctgggccctg ggttttgaga aactcgctgg caccacagtg ggcccctgga cccggccgcg 240
cagctggtgg actgtagggg ctcctgactg ggcacaggag ctcccagctt ttgtccacgg 300
ccagcaggat gggctgtcgt gtatatagct ggggcgaggg 340

<210> SEQ ID NO 36
<211> LENGTH: 494
<212> TYPE: DNA
<213> ORGANISM: Homo sapiens

<400> SEQUENCE: 36
gagaagacgc cacagatttc cttccctctc ctccaggaga ccataagata gatcccccat 60
cctctcagcc ctattcccat gcctccctct cattggagga gctgaccaaa gcagccctaa 120
cgggccataa cacttgacca attcagctgc tggcagaggg aggaaacaag tgttttccca 180
agtggcattt tcatctcgct ttcaccctga ctaaagattg tcttaagtag cagcccagcc 240
cgcccagccc caggtgggta gtggggagga gagctggcat tcctccaggt ggcaaatggc 300
gactctatac tctccgcccg ccccagggct ggatggatta gaaaaatccc tatttttctt 360
gtatcgatgt agagactcta ttttctccca aagacactat ttttgcagct gtttgaagtt 420
tgtatatttt ccgtactgca gagcttacac aaaattgaag aatgttaatg ttcgagtttt 480
cttatcttgt gttt 494

<210> SEQ ID NO 37
<211> LENGTH: 381
<212> TYPE: DNA
<213> ORGANISM: Homo sapiens

<400> SEQUENCE: 37
gacatttggg atttactttt ctccaatacc tgccaataca gaaaactatt atcagttgtt 60
attgttatcc cttgaaaagc gagggtgaca aaaacaacaa aacaccgtta taaacacatc 120
aaaggttcat tctgactgag gtaagacttt ccaagccctt gttagattag gccttataaa 180
acttgtgtgc attataacct aagctgtgca acctggtgaa gccaagagtg aactgatgtt 240
tcatttatat tttcatccaa atgacattat ctgcacgttt ttaaaattta aaaacaaagg 300
actatttaaa aatacagttt attaacaaac gtgaaactac tttctgttac attaggtgtt 360
ccctagtgtt tcttaatttc t 381

<210> SEQ ID NO 38
<211> LENGTH: 483
<212> TYPE: DNA
<213> ORGANISM: Homo sapiens
<220> FEATURE:
<221> NAME/KEY: misc_feature
<222> LOCATION: (45)..(60)
<223> OTHER INFORMATION: n = g, c, a, or t

<400> SEQUENCE: 38
cagaatagcc aagaaatccc tccttttcaa cgctctgtgc ctggnaacca ttagaggagn 60
tttaaaaacc atccctcata gcccacaatt ttgggtcaac tctcaaaatt gggaataaga 120
aaactggcac tgttgggaga aaaatcgttc ttactgaaac atgaactggc tcaggcaagc 180
aaatagcggg agtcggcaca ggaaggagtg tgtgctgcgg ggatgcgtgg tggcgtcacc 240
ttcaaaacta aagtggtgcc aggcggacag atgagtcctt gatcttgttt cctgatcttg 300
tttccatttg actgaattct gaaccttcat tgtcttcaca gtcttgccac ttgcctagtg 360
aggcttttcc gaacctggaa ggagacgtct agaaatccca actttgctgt gtaaggacca 420
ttagctgcaa gtcagtggaa gtctatagaa agcagtgtga attccatagt ggtcttgact 480
tct 483

<210> SEQ ID NO 39
<211> LENGTH: 403
<212> TYPE: DNA
<213> ORGANISM: Homo sapiens
<220> FEATURE:
<221> NAME/KEY: misc_feature
<222> LOCATION: (333)..(333)
<223> OTHER INFORMATION: n = g, c, a, or t

<400> SEQUENCE: 39
ttgatggatt ttcatttctt cgcacttctg agacggcaaa gccaaccact tagaagcctt 60
ccacatcttt gtcacctgcc tggctcctgc tctctgatgt acctctgggt agtgagatgg 120
aaatggtgcc tgcagaagtt ggggagaagg atacttttgc acagcctcca tgatgtcttt 180
attgcaaata tggatgacaa gggtctctgt tacaggggcc tcagagcacc ttcgtttctc 240
ctctagacca gggacaggtg tagagataag gactggcaac cagagcctca gcatccaaag 300
atggactgaa gtgggatggc tgacaggcac atnacttacg ggaaagggaa tttcatacat 360
acgatttttg ttttgtgggt aggagggctt atcatcaaca ctg 403

<210> SEQ ID NO 40
<211> LENGTH: 313
<212> TYPE: DNA
<213> ORGANISM: Homo sapiens
<220> FEATURE:
<221> NAME/KEY: misc_feature
<222> LOCATION: (38)..(38)
<223> OTHER INFORMATION: n = g, c, a, or t

<400> SEQUENCE: 40
taagatgcgc tgatctctgg tggttgtcac tagttctnct aggtgataat gatttaccca 60
tagatggagc tgttggatat tattttattg tacaaattca tgtttaaaaa actttgtgac 120
tgtttctagt taagtaattt tttaaccttt cttgggtcat agacttcttt ggtaaactat 180
gaactctcac caaaaagata cacatgcaac atgttaaata catgttagac tttgcataca 240
attttagggg ctcatgggcc tctaagccta tccatgtatt ccaggttaag ccctctgtta 300
tgatcaatcc att 313

<210> SEQ ID NO 41
<211> LENGTH: 289
<212> TYPE: DNA
<213> ORGANISM: Homo sapiens
<220> FEATURE:
<221> NAME/KEY: misc_feature
<222> LOCATION: (34)..(75)
<223> OTHER INFORMATION: n = g, c, a, or t

<400> SEQUENCE: 41
gagtcatcac actgttggaa tagtctgctc tttnacatgc tcaggtaggg aaaataggac 60
caaatatatt tccanagtgc ctaccactgt gtcatgttta cagtgagagt ttaaatattg 120
ttgatgtcct gactctgtga gctcataggg agtatcttca tagtaatgac atttgatcag 180
ccataaaatt tacattatgt tcatatgcac ccaaaaaagc tagtcaggta atgaataccc 240
ttgaagtgaa tagcaatttt gatttaggca gtgtgttagg ccatccttg 289

<210> SEQ ID NO 42
<211> LENGTH: 560
<212> TYPE: DNA
<213> ORGANISM: Homo sapiens

<400> SEQUENCE: 42
tgttctttca gctgctccaa ggattgagac ccaagtcatc atgaaaaagg cccaagtaca 60
gtcttaatgc gataaatcca ctagctaaga cgtcgagtgc caagaccagc cttccagccg 120
aggtttggac aaagtctcag gttcccgtga ctcagggtaa ggtgctgggg ctgccagagg 180
acctgcccca gcaagatttt tgtcaagagc gagactccat cagcccaggc agacgggagc 240

-continued

```
aggttcttgg ccagcgtaga cagcagcaaa cagcagcagg gaagccattc tcactgcatc    300

ctccctgcag tagccacggc caggccctta ggaggagcag tgaccggggg tgtccagaaa    360

tatcctgtcc ctggatggaa actaggtctc gtttggattt tttttttttt tttttttgcc    420

gtgttaggaa attatttatt aatttacaag acaggtttta actcagccga ggtgggaaat    480

ggtgtccctg tccctcccaa agcacagagc acagaaatga ggccgtttac atggcgagtc    540

tccgtgctgg tgtttaagtc                                                560
```

```
<210> SEQ ID NO 43
<211> LENGTH: 551
<212> TYPE: DNA
<213> ORGANISM: Homo sapiens
<220> FEATURE:
<221> NAME/KEY: misc_feature
<222> LOCATION: (235)..(235)
<223> OTHER INFORMATION: n = g, c, a, or t

<400> SEQUENCE: 43

tgttcatttt ccaactgcac taattgtgca tattactctg cctaatcttg tgcatgtttt     60

cattgatttc cctctcccgg cttttgcttc tcttgaaact gttgcccagt cacttctgct    120

ccaattctct tcctctctaa atagtagttt aattactgcc acatctccat gcatcagcaa    180

aatgttggtg acatttttct agcctggcag aacagattac ttaaagctat ttcanttcaa    240

agcagactga atgtgacttc atctaaaggc agcattaggt actgcatgga aataggtcat    300

taacttgaaa ctcttatcaa aatatatttt accagtttcc agaatttcca gtacaggacc    360

gcctgaagag agagccattg ttcaattcca attcagtgtg agtgacaaag tgaaatttag    420

aagtgaagtt gtctatttga tatttaactc tttattaaat ctttctttaa atttctgcct    480

gtcagtctat attgctgttt ttattataca tcagtttctt tgtataactt gtgagttccc    540

atgtgttttg t                                                         551
```

```
<210> SEQ ID NO 44
<211> LENGTH: 316
<212> TYPE: DNA
<213> ORGANISM: Homo sapiens

<400> SEQUENCE: 44

atttccggga cattggcgtt cccatgacca gtgtgcggct gccctgctat tttgagaacc     60

tcctctccca cttcttgccc cagaaagccc cagacggaaa gagctacttg ctgagcttgc    120

ccacaggtga cgttcccatg gatggcatgt ccgtgtctga cctgggtcct gtggtgctca    180

gccttttgaa gatgccagaa aaatacgtcg gccagaacat cgggctgagc acttgcaggc    240

acacggccga ggagtacgct gccctgctca ccaagcacac ccgcaaggtc gtgcacgatg    300

ccaagatgac tcctga                                                    316
```

```
<210> SEQ ID NO 45
<211> LENGTH: 569
<212> TYPE: DNA
<213> ORGANISM: Homo sapiens

<400> SEQUENCE: 45

tttgcccagt ttgagccaga ttccacagag tatatcaagg ttcatcacaa gacctatgaa     60

gatatagata aacgtggaaa atatgacctt ttacgttcaa caagatactt tggtggaatg    120

gtgtggtatt ttgtaaataa taaaaagatt gatggtttgc tgattgacca gattcagaga    180

gatttaatcg atgatgcaac caacttggtc cagctgtatc acgtgctcca tccagatggc    240
```

-continued

```
cagtcggctc aaggggccaa ggatcaggct gctgagggaa taaatttaat caaggtcttt    300

gcaaaaacag aagcacagaa gggagcctat atagaactaa cactgcagac ttatcaagaa    360

gcactcagtc gccattctgc agcttcctaa aaatatttta aaaatacatt tattttacta    420

aatactgact acatttctct gttaatattg agctaaatgt taaaaaatgg ccagattaaa    480

agatatcaat ttgtagttct ccctacaaag caaaaattat taccctactc acttttcgta    540

ggctacaagg atatttgagt gcctggtta                                      569
```

<210> SEQ ID NO 46
<211> LENGTH: 516
<212> TYPE: DNA
<213> ORGANISM: Homo sapiens

<400> SEQUENCE: 46

```
ttttaacaaa gtctgcacct cccagtactt tctttggtac ctctgcttac tgcctcttgt     60

gatgccacta gtcagaatgc cttggaaaag agctgtagtt ctcctaatgt tatggtttat    120

agggcaggcc atgtggctgg ctcctgccta tgttctagag tttcaaggaa agaacacctt    180

tctgtttatt tggttagctg gtttgttctt tcttcttatc aattgttcca tcctgattca    240

aattatttcc cattacaaag aagaacccct gacagagaga atcaaatatg actagtgtat    300

gttccacacc ctctgctact gtgttacatt ctgattgtct tgtatggacc agaagagagc    360

tttgggacat tttttctgaa cattctaagc attctagtga aagttcccat gttccaacag    420

aacttaaaag caatgtttgc cttatatata aaaggtacac aataattgag gtccaccttc    480

taggaaatcc taggactcgt ttatttggga catggt                              516
```

<210> SEQ ID NO 47
<211> LENGTH: 452
<212> TYPE: DNA
<213> ORGANISM: Homo sapiens

<400> SEQUENCE: 47

```
ttttgttcac ctctgcagac tgtgaatcct agctgccagt ttgcctatta tatgccaagg     60

catttgcaaa aatctcatta atctaaatca aaatagcttt aaagaaaaat gcatacactt    120

cctcagatca tcaaacagac tctggtccaa ggttggtaat gaaatgactg ttcctgacag    180

ggaggaatag cagggcccaa tcttctgaga tggcttctgg gtctttccat ggtcagagaa    240

gatctatagt ccgtcctgag gtctgtcaat gtcacaggaa aaggcaaact tgaggggatc    300

gtcgcctgct ggctaagacc agggagctaa aaacttgagg aagggaacct gcctgggtgg    360

gtgctacttc tgattcattg tccttgtccc tgtcataagt acctccctat tgtagataga    420

agggaaggaa actgttgact tgagcttggc ta                                  452
```

<210> SEQ ID NO 48
<211> LENGTH: 564
<212> TYPE: DNA
<213> ORGANISM: Homo sapiens

<400> SEQUENCE: 48

```
ggagaatgga acaaaagctg ggcacagcct tctcatggat gccagggatc tggtccttaa     60

gggaaaaggg aagtcacctt tggaccctcg acctggtttt gtctttgccc cgtgtcccca    120

tgaactccct tgtccccagt tgaccaacct ggcctgtagc ttctcacagg cgtaccatcc    180

catccccttc agctggaaca agaaaccaaa ggaagaaaag ttctctatgg tgatccttgc    240

tcgggggtct ccagaggagg ctcatcgctg gccccgtatc actcagcctg tccttaaacg    300
```

gcctcgccat gtgcattgtc acttgtgctg tccagatggg cacatgcagc atgctgtgct 360
cacagcccgc cggcacggca ggtatggggg gtgtgaccaa aatcagtggg atgtggcagg 420
aagctgcagc ccacgccagc atctgttccc acagggattt gtatcgttgt gcccgtgtca 480
gctcctgggg agatctttta cctgtgctta ctccgtctgc gtttcctcca tctacggctc 540
aggatccctc tgagagttga tgag 564

<210> SEQ ID NO 49
<211> LENGTH: 527
<212> TYPE: DNA
<213> ORGANISM: Homo sapiens

<400> SEQUENCE: 49
ttttgggagg ttgttgtggg agatggttga tttaggtttt caaaagctag aaataaaatt 60
tacatgcctt agatttcata aaattctgct ctaattgggt ggaaggtgct gtatctaact 120
tgtgttcctc ctaaggttat gtcctaataa ctattctttt aggagtatac ttctacttta 180
tagaaggttg cttttctttt taattttttc taacaaagaa aagaataaag tatttattaa 240
taagaaccag aaagcacttg aaactgatgt ttttaatggc tcatttaggg tagatttatt 300
tatctcatta acttaaaaca gctatgtgta tgaaataggt cacaacagaa cttgaacacc 360
aggttggtgt ctgagcaatc cctttcttat gggaaaaaca atgttcttgt ttgaacagag 420
ggtatcattg cagtcagtat tcacgtgtat attgttatat aagttgtata atatgcttgt 480
aaaggctgag ggtgagctgt atctggatgc ctttttacaa tttgatt 527

<210> SEQ ID NO 50
<211> LENGTH: 521
<212> TYPE: DNA
<213> ORGANISM: Homo sapiens

<400> SEQUENCE: 50
gatggcccca aaggctgagg gccccaaagc cacttgtctc ctaggatcca ggcctctggg 60
cttctgccaa gaactcaggg tggccctatg acttggagga gcaagatcag accgctcaaa 120
ggtccccgtg ttcactgtta cccagaggct cttgttacta cccacttcat tccccaccgc 180
tgccagtgcc actgccaacc ctgttcacag gcgcttccag cccactccag ccaggggagc 240
agggaagaag aaggggctcc ctcctcttca cattcccccc gaccccaaag ccagagaaag 300
ccagatggca ccagctgctc cggatgtgcc tgcccacatt gggggacagg gccgggcctg 360
ggctcggttc ccaggtttga gctctgcagc ctctctcctg gagtgagggg gctgaagtca 420
gaccaaagga agaactcaga aatgtcttgt ttatttgtgt ttgtgaccaa gcagcctctc 480
ccttcaccca ggtttatggc ctcgttttca cttgtatatt t 521

<210> SEQ ID NO 51
<211> LENGTH: 479
<212> TYPE: DNA
<213> ORGANISM: Homo sapiens

<400> SEQUENCE: 51
gcagaagaaa gtcttcccac aaccccattt tatttcatat tgggaaaaca caggcaacag 60
caggatgaaa aactaaacga aactttagag aatgagctgg tacaactacc cttaacagaa 120
aacatacccg caattagtga gcttcttcac actccagccc atgtcctgcc atctgctgct 180
ttcctgtgct ccatgtttgt aaattcattg ctgctgtcta aagagactaa gagtgctaag 240
gaaattcctg aagatgtaga tatggaagaa gaaaaagaaa gtgaagattc agatgaagaa 300
aatgatttta ccgaaaaagt ccaggataca agtaacacag gtttaggaga agacattata 360
catcagttgt caaaatctga agaaaaagaa ctgagaaaat ttaggaaaat agactacagc 420
tggatagctg ccctttaagc cttggagatg gggaggatcc ttggactttg tgtttttga 479

<210> SEQ ID NO 52
<211> LENGTH: 506
<212> TYPE: DNA
<213> ORGANISM: Homo sapiens
<220> FEATURE:
<221> NAME/KEY: misc_feature
<222> LOCATION: (106)..(117)
<223> OTHER INFORMATION: n = g, c, a, or t

<400> SEQUENCE: 52
gaagccatcg gctgagacta cacagcttgg ggcccgagga tgaaggcgtg taccactgtg 60
cccccagcgc ctgggtgcag catgccgact acagctggta ccaggngggc agtgccngct 120
cagggcctgt tacagtctac ccctacatgc atgccctgga caccctattt gtgcctctgc 180
tggtgggtac aggggtggcc ctagtcactg gtgccactgt ccttggtacc atcacttgct 240
gcttcatgaa gaggcttcga aaacggtgat cccttactcc ccaggtcttg caggtgtcga 300
ctgtcttccg gcccagctcc aagccctcct ctggttgcct ggacaccctc tccctctgtc 360
cactcttcct ttaatttatt tgacctccca ctacccagaa tgggagacgt gcctcccctt 420
ccccactcct tccctcccaa gcccctccct ctggccttct gttcttgatc tcttagggat 480
cctataggga ggccatttcc tgtcct 506

<210> SEQ ID NO 53
<211> LENGTH: 563
<212> TYPE: DNA
<213> ORGANISM: Homo sapiens
<220> FEATURE:
<221> NAME/KEY: misc_feature
<222> LOCATION: (122)..(122)
<223> OTHER INFORMATION: n = g, c, a, or t

<400> SEQUENCE: 53
agggcttgaa cctgagtctg cccagctcca gaactgagct tgcagccatt agccacagct 60
gtctcctgca tgtctgagca aagaaaggcc tttacacagc atcaccctgt gccatcccat 120
gncaccgtgg gactcagcta aaggactgtg caaagagggg gctcctgagt tggatttagg 180
caaaaggggc agaattcgtt tgatttttag agaaaatctc tggagagttt cttttgattc 240
atagaattcc ttttagattt ctttccagca taccaactag ctttagtagt gctgctacaa 300
ccagctctta taagtaagag tgaaaaagta ttcttttctt ctttaaaaaa taagtttttc 360
ttgcttatag ttaattctag aaaggcaata ctaaaggtat atattttttt caaaatgcta 420
ttttttactg cacttgataa ttatcctgac agctctgatc tctgtaatag attcactctt 480
cagctctggg cagaaccaga ggcagggttc acaccaaatt tgtaaatacc atatgtgggt 540
ctggtgtcca ggaacttttt tct 563

<210> SEQ ID NO 54
<211> LENGTH: 481
<212> TYPE: DNA
<213> ORGANISM: Homo sapiens
<220> FEATURE:
<221> NAME/KEY: misc_feature
<222> LOCATION: (368)..(374)
<223> OTHER INFORMATION: n = g, c, a, or t

<400> SEQUENCE: 54
taactagtta gttatcacct cgtcccttaa agtcagtgac ctcctgtgtt tgatgtatat 60
tacatagagt cttaagtcag tgtacagttc cactggaatt tgacagttgt ctctacagtc 120
atgcaactcg aagtagaaaa gagtgctgga cataggaagg gggtgcttgg tttgaggggt 180
taatgtgagg ccttttttgaa aaatgaatat tttgataaaa agaattcttg ttttagcaca 240
gttgatgcac ataagtgatt ctcatatttg ttgtataaac tggtttaata catttggaac 300
atagttggat tacattcatt tcctgggaaa gctagcttac catacattca agtttataaa 360
acaatttncc atangcaaag ccatttaaaa agttcattct gaaattattt catttaccta 420
cagtgaaata attgtgaact aagtagtctt tctgaaaact gttgggttct aggcattcct 480
g 481

<210> SEQ ID NO 55
<211> LENGTH: 545
<212> TYPE: DNA
<213> ORGANISM: Homo sapiens

<400> SEQUENCE: 55
gtgattgcag caggggtctc tgccccctcg ctcccaattc ctagtcgtga cttcatttct 60
aaaacagagc ctgaccaacc ttccatgtat ctccatcctc ccctgctcca gccagggagg 120
actgagggag tgccccgaga cccacgcaca tgttggggct tctgggccaa gagtactttt 180
tatataacta atttctaaat ccaaaagctc aaggaataga cagtgttctg tgacatggat 240
tggtttgaag gagttaccca ccatcccagc acgataatgt catctcccaa gttggatggc 300
agcacgatct ggccctaggg agcttcctgt tcccagaagt cattgtcctg ggctatccag 360
atgtccctag taaatcttgc ttccttctgc aatgttagta atgccttaag ctgacagttg 420
ctattttgca gaacagtttt cctctttgct tagctagtaa cttgcctctg agcctgggct 480
gatctgagaa acaggtgtga caagagcatg aaccagaggt gcacctgggg cagttcccta 540
ataaa 545

<210> SEQ ID NO 56
<211> LENGTH: 533
<212> TYPE: DNA
<213> ORGANISM: Homo sapiens

<400> SEQUENCE: 56
gtgctgaatt gtcactcatg ggcttgagag taggagactg gagaccaagg tggctagaat 60
ccagttgggc ctgatgtctc cctgttgaaa gggctccttg tggaatgaat agcacatggc 120
tcctgtggtg gatctgatag tggcatagca ccaagtgatg caggcctgcc aggggccaca 180
gacacagaag atgctcccgg ggtcccccat gtactccaga cacactgcag gccacctctc 240
ccagcaggtt gccagtcatg ggccccatca tcatgacttc tgtccaaggt actgtgtgca 300
gaaatgtgat tgagattcaa gtcagggcct ctctgccctt ttccctccag aaacaaaacc 360
aagataattt atcctgaaca cggtgaaaaa aggaagggag ggaggagaaa aagtccgggt 420
ctcacctggg attctctgtc tcctgcaaca tgaaggattt agcctgggag gaggtggtga 480
gaactctggg agagaaaaaa gaaggaaaga atagttttac ccatgctgaa gtt 533

<210> SEQ ID NO 57
<211> LENGTH: 434
<212> TYPE: DNA
<213> ORGANISM: Homo sapiens

<400> SEQUENCE: 57
gacattggtg gctcaaaggc ccctgtccca tgctttggac cagtcttcac agaggttgag 60
aaggccaaga tagagaactc tcccacaccc ttctgtgttg gagataaatt tttcgtacct 120
ctgcagagac tccttgcgta tcccaagttg aaccgcttat gtgctaatga agagatgatg 180
agatcagtca ttgctgactc aattcctctg agcagtgatg gttctgcagt ggtggctgac 240
ctgcgtaatt attttgatga acagtttgag ttttgaacca tgtttatttc ctgaaatttc 300
agggtctcag cgatagttgt gctcacttag aatttagttt tttttgtgta atcctaattc 360
aagtaatgtt tttaaagttt cactgcaaaa gtctatgttc caagccattg gacagacctg 420
cttgagatat ggcc 434

<210> SEQ ID NO 58
<211> LENGTH: 488
<212> TYPE: DNA
<213> ORGANISM: Homo sapiens

<400> SEQUENCE: 58
accttcaccc tacagcatta caggctttaa tcagattctg ctggaaagac acaggctgat 60
ccacgtgacc tcttctgcct tcactgggct ggggtgatcc ttggtgcctt tgtttccaca 120
aggccttttc ctgccccctg ccttgccaaa gacatttaat cagcacacag ctgccagact 180
attcccacag tgctccaaat gcacatgaac aacagtgacg gctccagcct tcgacccaga 240
gccccgtgcc cagtgcgtca gtgggcctgg ggttccaggc tacatcaagc actgatggtg 300
tcagggctgg tagttaccaa atcagggtta agaaacatca gggccacatt tcactacctt 360
cacagatcaa actcagcagc agtcatgact gtctgtcact acactgggga tcccaattcc 420
acataagcac ttttggaaga aaacagccaa agttggccta aaattggcgc tggaatttgg 480
gctgggaa 488

<210> SEQ ID NO 59
<211> LENGTH: 427
<212> TYPE: DNA
<213> ORGANISM: Homo sapiens
<220> FEATURE:
<221> NAME/KEY: misc_feature
<222> LOCATION: (314)..(314)
<223> OTHER INFORMATION: n = g, c, a, or t

<400> SEQUENCE: 59
ggtgcaccat gattagctca cacacaatgc caaggctgtg cttctattat ctgatacata 60
gtttgacaat gggtaattct actcagaccc tccctactga ttggctagga tgcctgtcag 120
gaactcatta tgctactggt tgtttgggga tccccatagt ggactacttt caggaatggc 180
atgaattgta accaactgag tgctgccccc actgttacgg aagtttataa aaccttagtt 240
ccagaagacc caaaggagag tactggtttg tgtttggtgc ttggcctaga tccagccacc 300
actctgaaac tcancacatc ttcattgaca gggagggagc ccaggacata tgtgtggctc 360
attgaccaga aggctttctt agtcccaaca gccatgaacc atgcacttat ggatacccag 420
cctttta 427

<210> SEQ ID NO 60
<211> LENGTH: 504
<212> TYPE: DNA
<213> ORGANISM: Homo sapiens

<400> SEQUENCE: 60
gcttgcacag accagcagtc acagaaatca ttcttcctgc tgtactgggc cttaactgcc 60

-continued

```
tgcaaatgtc cagcactact gcataggatg ccagagccac cgaaggaaaa cacagccaag    120

tttaataata ataaaaggaa aaatctcagc ctgcagaact ctggttttga cccaccatcg    180

gccagatgca catcttcagg gcctgttgag caccttctga aaagcagggc tcgtaataga    240

ctccagcaca ttccatcaga gtcaggaaaa ctgcggtgag tcccagagaa tctagggtgc    300

agggcaggga gcaggagtca taaggagtga taacctaaac tgtgtgtagt cagcggggag    360

ggtcttatgt tatcaggtga aatgagagcc agtaagttag ttgatcctgt cacagatata    420

accctgataa caccccatag atacgcgaca cgtgtgtcct gcccctgctt tccccatcca    480

acatggttct tctgttccac agac                                            504
```

```
<210> SEQ ID NO 61
<211> LENGTH: 512
<212> TYPE: DNA
<213> ORGANISM: Homo sapiens
<220> FEATURE:
<221> NAME/KEY: misc_feature
<222> LOCATION: (134)..(134)
<223> OTHER INFORMATION: n = g, c, a, or t

<400> SEQUENCE: 61

atgggcagca gctcttagac gccctgcagc atgaactggt gaccactcag cgcctcctgg     60

gagaacttga tgttggtgat tcggaagaaa atgtgcaggt gctggactta ctgagcgaac    120

tcaaggacgt gacngcgaaa aaggaccttg agctccgaag gagctttgcc caggtgctgg    180

aactctccgc agaggcaagc aaagaggcag ccttggcaaa ccaggaagtc tgggaagaga    240

cccagggcat ggcgcccccc agccggtggt atttcaatca agacagtgcc tgcagagaat    300

ctgggggagc acccaagaac acgcccctgt ctgaggacga caacccgggt gcctcgtcag    360

cccccgctca ggccacgttc atcagcccaa gcgaagattt ttcttcaagc agccaggcag    420

aagtcccgcc ctctctctct cgttcaggga gggacttgtc atgactcatg gttacattca    480

ggatacttga gcactttata tactaccgta gc                                  512
```

```
<210> SEQ ID NO 62
<211> LENGTH: 363
<212> TYPE: DNA
<213> ORGANISM: Homo sapiens
<220> FEATURE:
<221> NAME/KEY: misc_feature
<222> LOCATION: (160)..(162)
<223> OTHER INFORMATION: n = g, c, a, or t

<400> SEQUENCE: 62

tccagttctt tgaagcatcc tctgctgggt cttggggtgt gtggatggat tggctgtctg     60

atgggattgg taacccctcg ctactcaaga tggggggata caaacacctt cagggaaggg    120

gagcctggtt cttctcgttt tccttttttt ttttttttn nnaaaaaaaa actatttaat    180

tttttaattt atttttggtt gttttttgca caatgaagtt tcagcttctc aaccttctcc    240

cctacccagg gctgtggacc cagactggcc ttgagccaca gtccctcttt ccctcctcac    300

cctcttcccc ctgcgggctc ccgggtctgt ccatttgtta ctgtgctgtg ctggggattg    360

gcg                                                                  363
```

```
<210> SEQ ID NO 63
<211> LENGTH: 353
<212> TYPE: DNA
<213> ORGANISM: Homo sapiens

<400> SEQUENCE: 63
```

```
gtgtttgctg cggcaaggac gagccggggc gctgaagact atgctccagg aagcccaggt     60

gtttcgagga cttgcttcta cggtttcttt gtctgcggaa tcagggaaga gtgaaaaggg    120

tcagccacag aattccaaga agcaaagtcc accaaaaaag ccagccccag tgcctgctga    180

gccgtttgac aacactacct acaagaacct gcagcatcat gactacagca cgtacacctt    240

cttagacctc aacctcgaac tctcaaaatt caggatgcct cagccctcct caggccggga    300

gtcacctcga cactgagggc cctcggtgtg aagatgaacc ttccaccgtc ttc           353
```

<210> SEQ ID NO 64
<211> LENGTH: 483
<212> TYPE: DNA
<213> ORGANISM: Homo sapiens
<220> FEATURE:
<221> NAME/KEY: misc_feature
<222> LOCATION: (34)..(41)
<223> OTHER INFORMATION: n = g, c, a, or t

<400> SEQUENCE: 64

```
ttaatacttt cctactgata atgaaattta aaantggaaa ntttgtgagt gtttttcttg     60

tccaatagag cctaattgtt tcctttttta gtgatttaac aatctcttga gggctgcacc    120

tttaaattcc cagattgtca atagacatgt acagtatatg ggataaggtg gacacaagtg    180

cacatataaa taaaatcttc ttaagacttt taactattca tttacagtag gagagtatgt    240

agaaatcatc atccacaagt cataattagg ttgtgtgcct actgtagttt tttccatttc    300

tgtattatat aaacatttgc atattaaaat ttgatttttc ccagagacaa gtattatata    360

ctgtatctat atttaaatca aactgtggta atatatttct cagaaaataa tgttggggac    420

tatagcctga acatgtggac ttgaagcgac atggaggagg aggttgatcc cattgtgtat    480

aag                                                                  483
```

<210> SEQ ID NO 65
<211> LENGTH: 321
<212> TYPE: DNA
<213> ORGANISM: Homo sapiens

<400> SEQUENCE: 65

```
gatgtctttt ttggcagtgc acagccagag aacaacacat cacacacaag aaacagttgt     60

gctcatgtga tgggggcctc agcactagga aggagtggac tgttggcgca cgcagcagct    120

tgaataaatc tgaaagtcac tacgctgcgt aagagaagcc aaataaagcg catgctgtgt    180

acagagggtg tcgagaatgc ctcctacgtg acggaaagca gatccgtggt tccctgcaga    240

ctggcaggag cagattccaa aggcacagga agaagcttgc aggtagaatg tgttcattac    300

cttctgcgca ttataccaca a                                              321
```

<210> SEQ ID NO 66
<211> LENGTH: 400
<212> TYPE: DNA
<213> ORGANISM: Homo sapiens
<220> FEATURE:
<221> NAME/KEY: misc_feature
<222> LOCATION: (125)..(125)
<223> OTHER INFORMATION: n = g, c, a, or t

<400> SEQUENCE: 66

```
gaattgatta ccagctttac ttcccgatca cacaggacag agaacagctg atgttccctt     60

tccactttgt tgaccggctg ggaaagcacg acgtgacctg cacagtctca gggggcggga    120

ggtcngcgca ggctggagca atacgactgg caatggcaaa agccttgtgc agctttgtca    180
```

```
ccgaggacga ggtcgagtgg atgagacaag ctggactact tactactgat ccacgtgtga    240

gggaacggaa gaagccaggc caagagggag cccgcagaaa gtttacgtgg aagaaacgct    300

aagggtttgc tcccaggaaa ggagaggaag agctatatat atgtgccgac atgtggcaga    360

cacacagtaa ataatggctg accagcatga gggcagtact                          400


<210> SEQ ID NO 67
<211> LENGTH: 522
<212> TYPE: DNA
<213> ORGANISM: Homo sapiens

<400> SEQUENCE: 67

ggctttaagt tgtttcctat gtaaggtaat ctttcttttt tagtattatc taagaaggat     60

ggtagattat gtcattttgg aaactattgt gtcccttgta ttttaaatat ttcaggaaaa    120

tgcctacgat tgttacaaag atgtgtgttt tacttataac ataagctctg attctccagt    180

ggccactggg ccttctctgt gctctgtatt caactgcagt atgaattaca gaatgctgtg    240

catgttcgtt agtaccaata ccatgtgtat gtggtagaag ttgtaaccag tttctggatc    300

tgtatggtac tataaaatac ttattttata attctgtaac cgtatggcag tgttatgcca    360

aaaatgtata aagagcaata gtttttgttg cttactgctg tattttaaaa tattgtttct    420

aaaataatag agttagagtt ccttttgagt aattattttt aagaactatt gccaaatata    480

catcctgtaa aactaataaa agccactcca tcttagataa ca                       522


<210> SEQ ID NO 68
<211> LENGTH: 483
<212> TYPE: DNA
<213> ORGANISM: Homo sapiens
<220> FEATURE:
<221> NAME/KEY: misc_feature
<222> LOCATION: (408)..(408)
<223> OTHER INFORMATION: n = g, c, a, or t

<400> SEQUENCE: 68

tttttggcc gtgtggtcat ctaccacctg cgggtgcttg gggagaaggt gtgagacctc      60

taggggctgt ctcctccagg aagccctccg ggaagcacag caaagtccct cattctgcac    120

agaaggttta ttggttcctc ttgggaaggg tcccctccca ccacctgtcc agaagctgcc    180

tttgaagtca gttctgggtt tccccagctc tggctgacca ttttgttccc tgagtgtctg    240

agtccccggc aggcggcctt cactcagggt cagcgggcac caggttgctc tggaagagct    300

tgaggatgtg gttctcgatc acctgttgca ctgagatggg gcagggaaaa ggtgggctgt    360

gagcttgaat cgggagtggg gtggaggcac aggccaacct gcgctctncc cttaggggac    420

aaacagggac ccttgcagag acctgcatta cagagcaaag ctgggagaac cgaggactca    480

ccc                                                                  483


<210> SEQ ID NO 69
<211> LENGTH: 194
<212> TYPE: DNA
<213> ORGANISM: Homo sapiens

<400> SEQUENCE: 69

ggaagaagtg ttgtcggagt cagaggcaga gaaccaacaa gctggtgctg ccgctttagc     60

tccagagata gtcattaaag tggaaaaact tgaccctgag ctagactcct aatctagctt    120

gccattattg tgtgtgtaat tatggccaaa aggacatagg agatggacta agatgtcttg    180

gaccaccttt gtgt                                                      194
```

<210> SEQ ID NO 70
<211> LENGTH: 413
<212> TYPE: DNA
<213> ORGANISM: Homo sapiens

<400> SEQUENCE: 70
atggagaagc acacatggct cccctgtttg aaaaagggcc tgaataatac tctgcttctg 60
cctcatgaca tcagatgcta ctgttttggt ttttttcttt gagccccaat tcaccatttc 120
aggatgtgga tgggggcggg gttgggggta aaaacagcta taaaaagcaa ctgcagatgc 180
tgactgactg cagtgggcag ggtatgtagc tgctccaaga tgacttgcat cataccccaa 240
ttactgctgg catcttagtt gagagtataa tctgcttggt tgccttttta tgggaataaa 300
gagaataaaa ggtattttaa tagaataaag aaaaatttga aaatataatg gaaggtattt 360
aaagagccac ccacatagct tcaccaaccc ttctcacaca tcaactcata aat 413

<210> SEQ ID NO 71
<211> LENGTH: 355
<212> TYPE: DNA
<213> ORGANISM: Homo sapiens

<400> SEQUENCE: 71
agaaagaggt ctctacacaa gcccgtgatt cttcatggca agggataaca tcagaaatgt 60
ttcattttct gctattagtt tccattcctt tccccatcca ggcataaaga gaaacaaaag 120
acaatgatgg tattctctgt gtcctcagct ttggcacttt tgttgatgtt gctaaggagc 180
agtgaccttg ctaaaaagac tgaataatcc acccactgaa tagctaacct ggggaggaaa 240
tgaaaatttc ctttgtggat ctccccaaat ccattgttgt caccaggccc tcccagaacc 300
tcctcagttc cttcacagtg caaccctgtg tacttggccc gcaacccaat agtat 355

<210> SEQ ID NO 72
<211> LENGTH: 458
<212> TYPE: DNA
<213> ORGANISM: Homo sapiens

<400> SEQUENCE: 72
ctgctgctgt cacccaaagg ggaggtggcc agagccctct tgccactgga taaacaggcc 60
cttggtgaca tcccccaggc tccccatgac tctcctccag tctctccaac tccaaaaacc 120
cctccctgcc aagccagact tgccaagctg gatgaagatg agctgtaact ggtgaaaacc 180
atgggggtgg tgctgactca gccgcctatt ccccaaggag cttcagggca gtccttctgg 240
cactgctcca gaattcctcc ttcttggtgt gtctggaggg tgggcaaggc tgggagggat 300
atcaacttgg aggagaacac ctagacccaa ggactttttt ctgcccaagg aacacagttt 360
ccttcagctc ccatccctat gcatgcatca tggtcccccc aaaaggagga tatgtgggtg 420
ggtgggaggg ctggggcagg ggccagatag aaattatt 458

<210> SEQ ID NO 73
<211> LENGTH: 425
<212> TYPE: DNA
<213> ORGANISM: Homo sapiens
<220> FEATURE:
<221> NAME/KEY: misc_feature
<222> LOCATION: (161)..(321)
<223> OTHER INFORMATION: n = g, c, a, or t

<400> SEQUENCE: 73
gctccccaga cgatgttcca ggaggcgggt gtgccagaag gggccacgtc ttgcaaacca 60
ccgcgctgtc ctctttgaga aggagtctta ctcaggactg gggcctgtgc acacattgtc 120
gcctcttttc agcacttaga gattccttcc tttgtctagt ngctgaagcc agggctgaag 180
ttggcctcca aatctgggcc gtctcagagn gcngcgcagc ctggagtttt ccatctgtgg 240
ccaagaccca gtttttggga ggaggccctc atgggtcaag ccagcctgta ccaggatggg 300
gggagggggt tcccaacnta ngccccagcc acccagactc ccccaccccc actccctttt 360
ccactgctct gacctcgggc actgttgaaa tatagttttt attgcatttc tgccgtttta 420
caaaa 425

<210> SEQ ID NO 74
<211> LENGTH: 426
<212> TYPE: DNA
<213> ORGANISM: Homo sapiens
<220> FEATURE:
<221> NAME/KEY: misc_feature
<222> LOCATION: (74)..(74)
<223> OTHER INFORMATION: n = g, c, a, or t

<400> SEQUENCE: 74
gcaccaccca gcttgggtat ctggtgaatt ctgtggtctg catgtccatg tttttgacat 60
tctgggaagg gtgngcccag gctgtgattt gccatctact gctgcaggct atggatggta 120
ttcagaaggg aggggagatg ctgtgtgcgt gttctgaagg gtttcccact aaatggagag 180
actgactctc tccataagta tttgattttt actttatctc ctcgttgact tcacagtgta 240
agtgcagttt gtctctactg ggtgatgcat gcagataaat gtttatgtga acataagaag 300
tctgcatgtg tgggtgaact ctccacatca tgtcatttat tgtccatcat tacgtatctg 360
tggtgtctag cacattcctc taccttattt tctgtcattg tacctacttc tacctgaaca 420
cgtatt 426

<210> SEQ ID NO 75
<211> LENGTH: 536
<212> TYPE: DNA
<213> ORGANISM: Homo sapiens
<220> FEATURE:
<221> NAME/KEY: misc_feature
<222> LOCATION: (317)..(317)
<223> OTHER INFORMATION: n = g, c, a, or t

<400> SEQUENCE: 75
ggtattctgc agtgactatg ggaaagcctt gaatgttcta tcggttttta agggacttga 60
gaattaattc tggagagaat gccccattga acatcatcaa tattggagag ctttctgttt 120
ttctacattt gttaggaaac ttgtgagcat tcacactaca gagaaacttg aaatataaag 180
aagaagagaa agccttcagt gatgcctctg tgttagggaa aatatggaac ttctccctgg 240
atgcaaaacc tatgagtata ttaatattgg aaaatttttc agtgattctt ctctttcttg 300
tatatgagag aacttanatg gagaaacccc taggaatgta atcagtgtta ggatgcctca 360
gcctgaactc ttcactgagt ggccacaatt ttcactggga acaaaaagta taatcactgt 420
tttgagtgtg ggatatcctt tatcagtgtc tcatctgtag attggactgc tggctcatta 480 attttttag tcttttttc ttttaatata aacatttgtg tatagctgtt ccctaa 536

<210> SEQ ID NO 76
<211> LENGTH: 416
<212> TYPE: DNA
<213> ORGANISM: Homo sapiens
<220> FEATURE:
<221> NAME/KEY: misc_feature
<222> LOCATION: (48)..(338)
<223> OTHER INFORMATION: n = g, c, a, or t

<400> SEQUENCE: 76
agctttcctt tttgactgtc ttattttact taacagaatg ttttgaanat ttgtccttat 60
tgtagtactt ttcaagattt ccttattttt aaggctgaat gctatcccag tgattgtacg 120
tgccctgttt gctgaatcta ctcatcctta agggtacatt tgcttccagg taacatgttt 180
gtgagtaata ctacaatgtg catatatcta ttccatgttc tgctttgtct gtttgggata 240
tttttcatac actgattcag taccatgtgt attcccttgc ttttgttgtc tcatccgttg 300
atgntacgtc ccccaaatta ttgccacgac cagttgtnat gaagcttcac ccttctgtat 360
tgtgctagga attttacagc tataggtttt acattatagt cttcattcat ttttta 416

<210> SEQ ID NO 77
<211> LENGTH: 528
<212> TYPE: DNA
<213> ORGANISM: Homo sapiens
<220> FEATURE:
<221> NAME/KEY: misc_feature
<222> LOCATION: (26)..(153)
<223> OTHER INFORMATION: n = g, c, a, or t

<400> SEQUENCE: 77
gaaatgggca aaatagctca acaggntttt ntgcaaagaa gaaatacaaa tgnccaagan 60
gcacatttaa aaatttncag nnctattnac tcatcaggaa aatgcaaatc aaaaccncaa 120
gacacccaat gtctacaatc aaaaagataa tanctagtat tgatgaggat gtggagaaat 180
tgaaattctc ataacatgct ggtaggaatg taaaatgggg cagccacttt ggaaaaagtc 240
tggtagttct tcaaatggtt aaatgtagag ttacgatatg atccagcaat tcctctccca 300
ggtatatacc caagataaat gaaaacttat atccacataa aaacctgtgc acaaatgtcc 360
atagcagcgt tattcataat agcctaaaag tggaaacaat cccagttcca gaatgaggaa 420
ggggagaaac taatgtgtat tagctattgt gtgctaagca ttcaactaga ttatttacaa 480
accttgtatc atctcaactc tttaaagact gtattgcaat gttttgaa 528

<210> SEQ ID NO 78
<211> LENGTH: 237
<212> TYPE: DNA
<213> ORGANISM: Homo sapiens

<400> SEQUENCE: 78
agggcattaa tccccttcat gagggatatt ctctcatgac ttaatcacct gccaaagacc 60
ccacctctta atactacatc agtgatgggt tcaatgtatc aattgggtgg gagggggcac 120
attcagacca tagcatctag tcattctggt tttattaaga tttattagac ctgaggcatg 180
aaaaatagca tactggatgg gacttcagca tcgatgagtt gccttagtaa tactgtt 237

<210> SEQ ID NO 79
<211> LENGTH: 451
<212> TYPE: DNA
<213> ORGANISM: Homo sapiens
<220> FEATURE:
<221> NAME/KEY: misc_feature
<222> LOCATION: (45)..(125)
<223> OTHER INFORMATION: n = g, c, a, or t

<400> SEQUENCE: 79
ataccttgct caaagagacc aacatttgga ctgtatctga aaaantnaan angccncgag 60
gnatanatnc aaantnttct cacnggaacn gccncattcn catnttgngn tgnnacattt 120

-continued

```
ctgnnaggag cttgaggagt tttgggttta cagagccctt ttggtagaac ttaccaagaa    180

gctgacttac tgtgtaaagg cagaattaat ccctctcatg gaagttactg gagttttaga    240

gggtcgagca aaacagttat acagtgcagg ttacaaaagt ctaatgcact tagctaatgc    300

aaatcctgaa gtgctcgtaa ggacaattga tcatttatca agacgccaag ccaagcaaat    360

tgtttcatca gcaaagatgc tgttgcatga aaaagcagaa gccctgcaag aagaggtaga    420

agagttacta agattgcctt ctgatttccc t                                   451


<210> SEQ ID NO 80
<211> LENGTH: 526
<212> TYPE: DNA
<213> ORGANISM: Homo sapiens
<220> FEATURE:
<221> NAME/KEY: misc_feature
<222> LOCATION: (29)..(96)
<223> OTHER INFORMATION: n = g, c, a, or t

<400> SEQUENCE: 80

gacttgtaag ggtgccttaa atcctgaant actngtactn ctngtattna ctaaacccna     60

tgttagtttn acgccnaaga ttcntgtggt ggtttnacat attctttttc ccctttgtta    120

aggtggggag gccacagctt atgtgaatga ctttctcagg agttataaag tgatacaggt    180

aaagctaaga aaagaacaga ttttgataac ttttgtttta actgtccagt gttagggatt    240

gtggctacag tggtctaatt tttaaaaact cttttttttg ctttgttttt taacagactt    300

atcagcaggt tgcaggtgaa catggccttg aggtaaatct gtcccttgct gaatacagtt    360

tcagtagatt gtttatagta gtttcaggaa ttgagatttt ttacaaaaat acaaaagttt    420

tgcttggttc tgttctagat gttttcttct aaataaatga gaaagatgtt tcaacaaagg    480

ctctttatgc tgaataattg tgatgcttga agttgctaat ctgctt                   526


<210> SEQ ID NO 81
<211> LENGTH: 441
<212> TYPE: DNA
<213> ORGANISM: Homo sapiens

<400> SEQUENCE: 81

gtctccgaag aggaagtccc tgactagcta tataactttg ggcgagttac ctctcacttc     60

tttgtgcccc agtgttctcc ttgggaaact ggatttaggt tagatgacct tttaaggctc    120

cttgtatgat attttgtgat ctgtacatgg cagagtatag attaggagcc aaattttcca    180

acctagtgct atggttcaga atacatagca ccccaagcgt ctggctggag ccgaggatgg    240

gtcctccagt ttttggcaca gatgttccgg agcccaggaa gcatcccata accaaccttc    300

agccccaccg ccaccccccag cgtattccag agccgcttcc aaaccacagc ctatcctctg    360

ctccatttca ctcttgccct cacagacttt cagcctccat gctctgagac aactgtgggt    420

aggtacatct ctgttggtgg a                                              441


<210> SEQ ID NO 82
<211> LENGTH: 430
<212> TYPE: DNA
<213> ORGANISM: Homo sapiens
<220> FEATURE:
<221> NAME/KEY: misc_feature
<222> LOCATION: (354)..(354)
<223> OTHER INFORMATION: n = g, c, a, or t

<400> SEQUENCE: 82

ctgccctcgc tgctggaagg caaggggccg ttctcgcctt ggttttctag gttgtgttgc     60
```

ggcaggagct gactgcccct aggcctagat ctctgcacaa cttcgctcag ggacacctgc 120
ctctgtgcat gtctcatggt gtgaatgtgt ttcctgctca caggtaccgt tttgtgtcat 180
gcagttactg gaatgtacaa aagcagctgt gatctttgtg agagctgcac agagcaggag 240
tctgagagct gcacagagca ggagtcttta tttggttcac ttctggtctg cagcaaccac 300
ttgctactaa aagatggaaa agatgtacaa aaatgtcaca gccctttaga aagngacatt 360
atcagaaatg tatgaccttc agtcctccct ccctctccta tgccccccacc agaccaggcg 420 gcgagaagga 430

<210> SEQ ID NO 83
<211> LENGTH: 528
<212> TYPE: DNA
<213> ORGANISM: Homo sapiens

<400> SEQUENCE: 83
cacagtgagt tgcaggttca ccccagcgtc agtggcgggc gggaagtggg gatgacacaa 60
ggacctgagt gtccaagggg gcttcatgga gccctcatgt gaagtcccca gcatggaccc 120
tgacacatcg taggtcctca acaaatgtca ctccctgttg tcactctgtt tagtactaag 180
aataatgata taaaactggg acagtaagga aaacacaaac tgttgggacc tatatctgaa 240
tctattagtc tgcctaatag aaaagccacc atcaggattt tggagattac aagctcactt 300
tagattagcc atactggagt cagccctgga ggctcccaga gatcagaaca atcccagcgc 360
ttgacaggat ggctgggaaa caatacatat gaatgccgga aaatgcagaa ctaatctagg 420
aaaaagtgta agaagaaaat aaacatcatc tgtcattcta tctatcagag ataactgctg 480
tcaatatttt ggtttccttc caatattttt tctattcact ctgtgcat 528

<210> SEQ ID NO 84
<211> LENGTH: 470
<212> TYPE: DNA
<213> ORGANISM: Homo sapiens

<400> SEQUENCE: 84
cctagctcct caagtgtgct tttttaatat atagttgata tattattgaa ggtactacaa 60
aatagaaatc tctggagtgc agaagttaag aaaataacct tcatactgaa aatatatcct 120
taaaaaaaca acaacaaaaa cctctataca aatgtagtac agcatacaaa tttttaaaag 180
atggaatgaa ggcacgaacc attgcaagtc ttttggaaat gtatgaacgt aggcatgcta 240
agttgaaaat agtcttaaaa aactagtgaa aacttcatgt atataaaata attcagaaat 300
aaatctgcta acattcttca ctttcaggtt gcatgtgtga atccaacatg ttccttcttc 360
ataaatagtc aagcgttcct tcagtggtgt ttgtgtggtc tgtcttcgtg ctggtcacca 420
gcctcagtat gtctggtaga cgtcggggat ggggacctga atggcagcag 470

<210> SEQ ID NO 85
<211> LENGTH: 530
<212> TYPE: DNA
<213> ORGANISM: Homo sapiens
<220> FEATURE:
<221> NAME/KEY: misc_feature
<222> LOCATION: (49)..(121)
<223> OTHER INFORMATION: n = g, c, a, or t

<400> SEQUENCE: 85
taagcacagt agcattccac cattgggcta tgacctgagg agaatcaang tagcnttntn 60
aggcctngtg gacatcgtgg atatnaagga atgctctcgt aggagggtac aagaacccca 120
ncatgattcc aatagagaag gcccaggggc ccatcctgct cattgttggt caggatgacc 180
ataactggag aagtgagttg tatgcccaaa cagtctctga acggttacag gcccatggaa 240
aggaaaaacc ccagatcatc tgttaccctg ggactgggca ttacatcgag cctccttact 300
tccccctgtg cccagcttcc cttcacagat tactgaacaa acatgttata tggggtgggg 360
agcccagggc tcattctaag gcccaggaag atgcctggaa gcaaattcta gccttcttct 420
gcaaacacct gggaggtacc cagaaaacag ctgtccctaa attgtaatgc atttgtctgt 480
tgttgacatg agagattcaa gatcagattc tagtgttcag taaccctatg 530

<210> SEQ ID NO 86
<211> LENGTH: 466
<212> TYPE: DNA
<213> ORGANISM: Homo sapiens
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (53)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t

<400> SEQUENCE: 86
gcctcgggag ccccgaatag cagctgggag aaggggcgag gactngagcc tcnnnnnccn 60
ctgccggccg ggctagagat acgggcgtgc cccccattgt gcgcctcccg cccnccggtc 120
ccctcaccct gcggccacnt ggggcgtggg gcggtgctcc tgcccgtgca cgtagccgct 180
gcgagcggag gcctgctcac ctggtgcctg ctactcactc ccccgggccg gtgggcgaag 240
gacacccgca ggaactcggc agaggagaaa ttcagacggc tcccgagggt aggaaaagac 300
cccggcccac cgtggaatct gaaacacccg accactctgc catcccatgt ttcaccagtc 360
agacccccag ggcagggcag gggaagcaga atgcaaactg gggcaccgtt tccctgaagc 420
gtgttggccg cgtttgtcgt agtgctagag gtgcataccc ttggac 466

<210> SEQ ID NO 87
<211> LENGTH: 362
<212> TYPE: DNA
<213> ORGANISM: Homo sapiens

<400> SEQUENCE: 87
tagtgcaagc aacatgccat ttcaaatccg tagacttgtt tctttgatac tcttgctgta 60
ggtcgccgtg aggggtaggg aagcatatat actgtaggga gaagtatcaa aatcatttaa 120
ggtctttttt ccaaactagt gttcccctcc cacatcccaa taactcttgg aagtctggtg 180
ctccctctag gtgaaaatca tttgctggct tatggagtca ctgttgctga gtcccatccc 240
ccagttacag tgcagtggaa aacaggttta gaatctagaa cttgtttgta tgttgtcact 300
tggttatgtt ccaagtaggt tagaaccatg gaaaagagat tgcaaatggt agtttcttct 360
ag 362

<210> SEQ ID NO 88
<211> LENGTH: 394
<212> TYPE: DNA
<213> ORGANISM: Homo sapiens

<400> SEQUENCE: 88
gtggttgtat gtgtctgatg gcttatgtaa acatagaaga agtcttcaga tggctaaaat 60
aaacatgcgc gtgttaccaa aggatatgtt tacacaaacc atttgctcag cctctgaaat 120
aatgaataaa tgaagatttt actaaaataa ttgggaggat ttttgtgttt ctgcggatgc 180
cataattgaa tggcaccaaa gagactttta tcagctattt tccgtgttac atgtgttagc 240
agttcctttc tgtgggttga atacttcatt ctgtagttac tttacacatg tttttctaag 300
aaattgtcgt ttattactgc aattctagag agttgcttga tttctcaaga gaaatttagc 360
agccagtaaa ggttatttgg atctggttgg tcag 394

<210> SEQ ID NO 89
<211> LENGTH: 395
<212> TYPE: DNA
<213> ORGANISM: Homo sapiens
<220> FEATURE:
<221> NAME/KEY: misc_feature
<222> LOCATION: (105)..(123)
<223> OTHER INFORMATION: n = g, c, a, or t

<400> SEQUENCE: 89
gttctcatga gatctggcac ttcacccctc actctctctt gctcctgctt tggccatgtg 60
gagtgctcac tccccttttg ccttctgcca tggctgtaag tttcntgagg cgtccccaga 120
agncccatca gataccagtg ccatgcttcc tgtacagccc atggaactgt gagccaacta 180
aacctctttt atttataaat taccgagtct caggcacttt ttatagcaat gcaacaatgg 240
actaatacat atactttagc ataaaaacat ttaaaagagt ctgaaactgg agtagttaac 300
tcagtaaaaa taacttggca ataaaacaca gaaaaacaat ctatttgatc atgtagtgat 360
tcctaatgta aatcctagta caactgtcaa ctgat 395

<210> SEQ ID NO 90
<211> LENGTH: 342
<212> TYPE: DNA
<213> ORGANISM: Homo sapiens

<400> SEQUENCE: 90
cttgctgtga gccttttggg tttgtttcct agctccaaat cttaacttgg tgtcaagttt 60
cctggctggg agacaagctt ttaccgactt cctctgcttg ccagcaaagt catctgctaa 120
ctggatattg gcagcttctc tgctgtcttg cagctgcttc cggagtgggt tccacaggga 180
ttcccgtgtg ttcttggttc agcttgcaga gggactttca cactccctgg agaccgtttc 240
ctcccattct gtctggagtt ttcggcctac cccaagacaa tgagatattc ctgacctttc 300
cacctatttc cctccaaccc caccttccga aatacatttg ct 342

<210> SEQ ID NO 91
<211> LENGTH: 386
<212> TYPE: DNA
<213> ORGANISM: Homo sapiens
<220> FEATURE:
<221> NAME/KEY: misc_feature
<222> LOCATION: (26)..(198)
<223> OTHER INFORMATION: n = g, c, a, or t

<400> SEQUENCE: 91

-continued gtcagggacc gagacaatag tggctntggg tgtagcaggt cgggagaccc cagcccatcc 60
ggcctccctg ccccgccacc tcccggggca ntggaggacg ccggccacga caggctcctc 120
tgcttccaga tgactcctga ggactacgaa aagcttggct ttcccggtgc ccgggacctg 180
gccaacatgt tccgtttnta tgccctgaga cccgaccgtg acatcgagct gaccctgaga 240
ctcaacccca aggccctgac gctggaccag tggctggaac agcacaaagg ggacttcaac 300
ctgctgtgac ctgcccgcct cgcggcccct tgtggggatc gggggcacca gaggggcaga 360
ggcaccaaca tctgaataaa gccatt 386

<210> SEQ ID NO 92
<211> LENGTH: 531
<212> TYPE: DNA
<213> ORGANISM: Homo sapiens

<400> SEQUENCE: 92
atctacatta tcttcttttt actattctag aagattcact ttataaaatg tgcatcttaa 60
ggagacatac tgatatttct caatctgtga gtaatggact aattgctatt aaatttggga 120
gctttacata tgccacaaca gaaaaagtca gaagaagcat ctacagttgt ttagatgcac 180
agttttatga tgatgaaact gtaacagtag ttcttaaaga cactgtagga cgtgaaggaa 240
gagatagact cttggtccag ctgcctttgt ctttagtata taacagtgaa gattctgcag 300
aatatcagtt cactgggact tattctacaa ggctagatga acagtgtagt gctattccca 360
cccgtaccat gcatttcgag aagcactgga gattactgga aagtatgaaa gcacagtatg 420
ttgctgggaa tggttttcga aaagtgtcct gtgtgttaag ctcaaatctt cgtcatgtga 480
gagtatttga aatggacata gatgatgaat gggagctcga tgagtcttca g 531

<210> SEQ ID NO 93
<211> LENGTH: 431
<212> TYPE: DNA
<213> ORGANISM: Homo sapiens
<220> FEATURE:
<221> NAME/KEY: misc_feature
<222> LOCATION: (27)..(101)
<223> OTHER INFORMATION: n = g, c, a, or t

<400> SEQUENCE: 93
gagttgatgg tgttgctggg ttataancag cttcaaagag aaggcatttt gaatgaaggt 60
ggaaacataa tggccaggag aacaagcaaa ggactaggaa ncagtgaact tcatcttggc 120
ctcaagttcc tgaggtgcat atgaataaac agtctctaac ccagagggtt tcaagaaaag 180
cagagtcctc aaaatccaaa ggtagagttt ccccacattg atattatact aattacacgt 240
ataacagtac tttggaaaag cacaggtctc tggtcacctc taaaaggcaa ggttggtaag 300
gaggtcaggg tgtcacctgt tggtagtctt aactaaatgg tctcttcaag ggatctaagg 360
atggaaaggg gatatataat ggttggatta aaggctcatc attgattagc aaattgtccc 420
ttttgtttct t 431

<210> SEQ ID NO 94
<211> LENGTH: 453
<212> TYPE: DNA
<213> ORGANISM: Homo sapiens

<400> SEQUENCE: 94
aaaccagcct ttggagaggg cctcatggca agaaactaag ggtggcctct agccagtagt 60
cagcaagaaa acagatcctt gttctagtag tgtgccagga actgaagatt gccaacaacc 120

```
ttgttatttt ggaagtgaat cctggttcag tggagcccta gctgagacct tagctctggc    180

taacaccttg attgcagtct tttgagacca ggaaacagaa agaagccagc taatctgtgc    240

ttggactcct gacccacaga acctgtgaga taataaatgt gtcttgttct taacacacca    300

gatttgtggt aatattgtta cacagtgtag aaaactaaca aactaggcct caaaataaat    360

ctataaacag ttttgcaggt acactgtaga acacacaata aaaagtagcc acagaaagag    420

acatgagtga ataccagcag gagcttctat tta                                 453


<210> SEQ ID NO 95
<211> LENGTH: 480
<212> TYPE: DNA
<213> ORGANISM: Homo sapiens
<220> FEATURE:
<221> NAME/KEY: misc_feature
<222> LOCATION: (83)..(163)
<223> OTHER INFORMATION: n = g, c, a, or t

<400> SEQUENCE: 95

tgtgtgtcta agcaattctg gcccctggct cccaccaccc taccctctcc acaaaataat     60

agacattagg ggaggtaagg gancagaaga ggtctcttng cagatattat atttttaaaa    120

antggttcta tgntaataag cagcagctaa ggagacagaa agncagtaga tgaagagagt    180

gccaatatct tccatgggga aaaatgaatg aactgaaaga gaatattatt tttctagaat    240

acagaaagct gtcctctcac agatcagctg gaattccaag gtggattatg gacttcttct    300

aactcccatt gatagtgctt cttaccaggt gaagggaagg gctacttttt cctaaaggag    360

aaaaaagctt tcagacaaag ctcgtaccaa cccctgaact gcaaatttgc tcaagtgacc    420

gtgcatactt atattcctaa tttaaatgat tatttatgtc aaacgctcat tgtgaaactt    480


<210> SEQ ID NO 96
<211> LENGTH: 475
<212> TYPE: DNA
<213> ORGANISM: Homo sapiens
<220> FEATURE:
<221> NAME/KEY: misc_feature
<222> LOCATION: (133)..(365)
<223> OTHER INFORMATION: n = g, c, a, or t

<400> SEQUENCE: 96

ttgggcacca cttccatcag gaaaacagtg tgcaagatgg agaaactaag gacaaacccc     60

agagaaactg gacaaaccca gcagaagaaa ggaagaactg caactcagaa atcacataac    120

caccaagcag gtntggacca cacatgctaa atgtgcatcc actatggcga gtcccaggcc    180

tttaacagca gggactaagg agggcagagg ctgacaccaa cccccttca tactgtagca     240

ctacatccct ctcagatacc agtttaacac gaagtctccc tgtttgactc ctgtgagttg    300

tgtattgaac tanaaagtgn ttnctgagtt naaaataaaa gcgcnntnnc nnnnnnanaa    360

nnnanattgt gtatcttgac ttctcaatga tagcaagtta cattttgcag ttttcttcct    420

atacccacaa atgaaactat tcagacttaa atatcttcct gtgtgcctaa acgtt         475


<210> SEQ ID NO 97
<211> LENGTH: 552
<212> TYPE: DNA
<213> ORGANISM: Homo sapiens
<220> FEATURE:
<221> NAME/KEY: misc_feature
<222> LOCATION: (243)..(509)
<223> OTHER INFORMATION: n = g, c, a, or t

<400> SEQUENCE: 97
```

```
taagaaatgt cgaaggaggc cgggcgcggt ggttcatgcc tgtaatccca gcactttggg     60

aggccgaggc gggcggatca cgaggtcagg agatcgagac catcctggct aacacggaga    120

aaccccgtct ctactaaaaa tacaaaaaat tagccgggcg tgtggcgggc acctgtagtc    180

ccagctactt gggaggctga ggcaggagaa tggcgtgaac ccgggaggcg gagcttgcag    240

tgngccanga tcgcgccact gcaccccagc ctgggagaca gagcgagact ccgtctcaaa    300

aaaaaaaaaa annngacaaa ggaaattctt ctagttcctt taaggatttc tctagcacag    360

gatcagagag gatcttggtt attggtgact ggtgagattc tgttgggtgt ttggaagctt    420

caaatgcatg gagccacccc ttaaaaatgt ctcactggag gcaggcacgg tggcttatgc    480

ctgtaatccc ngcattttag gaggccgang caggtggatg gcttgagtat atatacttcg    540

cgagcaccgt gg                                                        552
```

```
<210> SEQ ID NO 98
<211> LENGTH: 295
<212> TYPE: DNA
<213> ORGANISM: Homo sapiens

<400> SEQUENCE: 98

atgagaacat ggtcttggcc ggagcaattt ctgggctggt gggacccttg tccacaattg     60

tagtttcata tatgtgcatc ctctgtgcta tccttcagat ccaatcaagg gaagttcaga    120

ggaaagcctt ccgcacctgc ttctcccacc tctgtgtgat tggactcgtt tatggcacag    180

ccattatcat gtatgttgga cccagatatg ggaaccccaa ggagcagaag aaatatctcc    240

tgctgtttca cagcctcttt aatcccatgc tcaatcccct tatctgtagt cttag         295
```

```
<210> SEQ ID NO 99
<211> LENGTH: 344
<212> TYPE: DNA
<213> ORGANISM: Homo sapiens
<220> FEATURE:
<221> NAME/KEY: misc_feature
<222> LOCATION: (56)..(262)
<223> OTHER INFORMATION: n = g, c, a, or t

<400> SEQUENCE: 99

ctgtgttgtt ttgctggtgg ccacgaatcc gaaaggccca tgctgcagcg tgcccntgct     60

ttgagtttgg ttgatatgcn ttaataagaa cattagtttt cntgggagaa tttggtagca    120

cccgttcttc ccttcactgt gtgggggaaa tagtgttgat tgaaaggaag aggactccga    180

gattggattg gagcaagaaa gtgtgggtat cgtgtgttgt gactgtgtct tctccggggt    240

gctgcttcac tggaggtctc cnttcagggt ctggccctca tgcctggccc caggtgctcg    300

tgtgcacgtg agcggctctt cctgctgact gactacagct aatt                     344
```

```
<210> SEQ ID NO 100
<211> LENGTH: 381
<212> TYPE: DNA
<213> ORGANISM: Homo sapiens

<400> SEQUENCE: 100

caaagattcc ctcgaatcct cgtgctccat ctgaatcgat tttctgcctc ccgaggctcc     60

atcaaaaaaa gttcagtagg tgtagacttt ccactgcagc gactgagcct aggggacttt    120

gccagtgaca aagccggcag cgtccactat ggccactaca cagccctgtg ccggtgccag    180

actggttggc atgtctacaa tgactctcgt gtctcccctg tcagtgaaaa ccaggtggca    240

tccagcgagg gttacgtgct gttctaccaa ctgatgcagg agccaccccg gtgcctgtga    300
```

cacctctaag ctctggcacc tgtgaagccc tttaaacacc cttaagcccc aggctccccg 360
tttacctcag agacgtctat t 381

<210> SEQ ID NO 101
<211> LENGTH: 501
<212> TYPE: DNA
<213> ORGANISM: Homo sapiens
<220> FEATURE:
<221> NAME/KEY: misc_feature
<222> LOCATION: (171)..(371)
<223> OTHER INFORMATION: n = g, c, a, or t

<400> SEQUENCE: 101
cccgaagagc acccagcata tagctctcat ttgttgattc tgttagatca tgatcaatgt 60
taagcctaaa aacaaggtgg ccacatcagt ggtttgtaac ccatgtttat tctaatcagt 120
caatctgggg ctatatataa tagtagttga atgtttatag tactaccctt nggaaaattc 180
ccatatattc ncncccagca tggatataaa tacnggaaag atttcccatt gagtacttct 240
ctttagcact ccagntaaca ctagacaaat aagcacctaa atgccgagtg tttgtcagtt 300
ttaaaattag aaaagaaggc aagttgtttt cttgtctacc tgtttaataa attttttatt 360
gnccaagtan ntatgttcat ttgatttaat acgttgaaat gtagtttaaa atatatattc 420
aaataactaa caagtgaagg aataatttat ttagaaacgt agaaataatg gtactgtaag 480
cagttgcttt agagtctttt a 501

<210> SEQ ID NO 102
<211> LENGTH: 269
<212> TYPE: DNA
<213> ORGANISM: Homo sapiens

<400> SEQUENCE: 102
cctctcttaa agcggcacca acgtgagaga gacaggcaga cagacagaaa gccagaggct 60
tagggaaact ctggaaccca gacaagaatc ttttcgctgg gaaagactca gatatccttg 120
tttgcacagg actggtggaa aatctcccat gcgaccctcg gggcccagag ccatctgggt 180
ctgatgttct gttccattgt acatcgaaga gatatatatg cacatatagt atctatattc 240
atacatatta tactcttgtg tgtagtgca 269

<210> SEQ ID NO 103
<211> LENGTH: 449
<212> TYPE: DNA
<213> ORGANISM: Homo sapiens
<220> FEATURE:
<221> NAME/KEY: misc_feature
<222> LOCATION: (278)..(278)
<223> OTHER INFORMATION: n = g, c, a, or t

<400> SEQUENCE: 103
tcatcaagcc tttcgttttc aaaccaccat ttgtcagcct tgaggtagag agacatatag 60
atttgaaaat actttcttaa gagatcatgt aactatataa ctctgaattt aaaaattgag 120
gggggaggga taatttcaac ccactgcctc ttaccagaaa cattttttta aatctgtaac 180
tgctttagtg ttaacagggt gcaaggtggt ttttgtcccg tattgttctt aaaaggttct 240
catttattgt gattgtattg tactgtatga gaacaaantc ataaattgcc ttgtattgtt 300
tataatagac cataccacgt actacttcag tttttatgtt ccaagttttt cagtgatgca 360
tgttaacagt taggtcctaa aattctgtgg tgctaattct cccataccca atggtgcttt 420
tgtggatgct aactgcacac atgctgaac 449

<210> SEQ ID NO 104
<211> LENGTH: 468
<212> TYPE: DNA
<213> ORGANISM: Homo sapiens
<220> FEATURE:
<221> NAME/KEY: misc_feature
<222> LOCATION: (362)..(362)
<223> OTHER INFORMATION: n = g, c, a, or t

<400> SEQUENCE: 104
cctatccctg gccaaggaag tatgcaaatt gtattgtggt ttttgaagtt taggtgatct 60
cttccttcta tccctagcca aggaagttca tcctgactcc ccaacaagca tatcaaaagg 120
agtgtttcgt cacctttttc ctcttaccct ttacatcctt ttagcaataa agtgttcaga 180
acaaactggt tttcctttac tgtgctttgc aaaacttatt catgttttat tgggtgactt 240
tgtatttaca ctttcctcag atagtctgtt gtcagatgac tttgaccaat gattgggagg 300
aaccaaatac agaggatttt atcctatgcc taatctatat tgtctacaga gtaaatcagg 360
tntgaatttg tgaacagtaa tgaaacaatt ttccaactaa tcagaagaat tgtttgttaa 420
gtaaccttaa ttactcagtt tttggtgaat tgtttgcggc ttaacttg 468

<210> SEQ ID NO 105
<211> LENGTH: 377
<212> TYPE: DNA
<213> ORGANISM: Homo sapiens

<400> SEQUENCE: 105
gaaggagagc tgttctgcat ccataaaaac cagttaaaag ggatttcata aggtctgaaa 60
ttgagaactt tcccaagaat actgcatctt gttctcttgt gcaatataca gacgtgtgaa 120
tattcctaac agtaaccaaa tgggtgcact ctctgtgaaa acgcatcttt caaagagttt 180
tttaaacaaa ggagactcct gggcctttag aaataattgc cacaaactgc aaaaacaatc 240
tccaacctcc cacttctgta attctcatct gttgtcttac tagaaaattt atttctctgg 300
taataatgtt ataattgata tccctgtctt ctcaagatgt aaaatacttg taaaaacttc 360
tctgtccatc agaaaat 377

<210> SEQ ID NO 106
<211> LENGTH: 398
<212> TYPE: DNA
<213> ORGANISM: Homo sapiens
<220> FEATURE:
<221> NAME/KEY: misc_feature
<222> LOCATION: (94)..(113)
<223> OTHER INFORMATION: n = g, c, a, or t

<400> SEQUENCE: 106
tagaaagata attccgtctc tcctttggca gtaggcatgt ccctgtgagg gaggagatca 60
gcaggatttt tccaagcacc tgtcaaaacc ctgntgatca aaacagaaca tancaataac 120
aaagaatggc caaaaccagc tcggaatagg aattaaaatg catttgcata agatactccc 180
accagggcca tgacagttta caaatgatcc cacggcaata acccaggaat tatcttatat 240
ggttccagga acttcctgtt cctagtttat gaataacctg cctcttattt agcatataat 300
tagcagtggg tataaatata gctagccagc aatcctggag tgctattcta cctgtggggt 360
agccctgctc tgtctgtgga gcagccattt tgctgtac 398

<210> SEQ ID NO 107
<211> LENGTH: 307

<212> TYPE: DNA
<213> ORGANISM: Homo sapiens

<400> SEQUENCE: 107
gtagagatgg gctgtcttgc cttagagaca ttaaggtctg ttataaagct ataataacga 60
agacagcctg gtattagggt gccagtgtag ttacagacaa agagaccaat ggaacaggat 120
aaaaagccca taaataatct catgcatata tgcacacttg acttacaatg gaaggagtat 180
tgcagatcag tggggagaga ctgaactaat caataaatca tgcagttaca agatcataca 240
tgtggagaaa caaaatgaaa ccagatcctg aagtacacaa aaaatcggtt ccaggtatat 300
tgaatat 307

<210> SEQ ID NO 108
<211> LENGTH: 352
<212> TYPE: DNA
<213> ORGANISM: Homo sapiens
<220> FEATURE:
<221> NAME/KEY: misc_feature
<222> LOCATION: (35)..(318)
<223> OTHER INFORMATION: n = g, c, a, or t

<400> SEQUENCE: 108
attacttgac caattttcat agcaaactga ttggnttcac ttatcccccc actgaactgt 60
taagacctgg cgagatcctt tttatagttc tttaaacttc caggactttc tgcttatctt 120
caggaaggac agtggacctt caggggagag gagaaggagg aaatttgcat atttaaaatg 180
tgtgatctga gccaaacgct cttcagctaa cttgatctcg catcattttc ccagcttcct 240
ttgagaattc agaatcaaaa ttcaggcatc accatctagt gaccacaggg tcctgcaccc 300
cagcccaaac ctggggancc cttagggata atgccctttc tcatttgtct tt 352

<210> SEQ ID NO 109
<211> LENGTH: 455
<212> TYPE: DNA
<213> ORGANISM: Homo sapiens
<220> FEATURE:
<221> NAME/KEY: misc_feature
<222> LOCATION: (327)..(343)
<223> OTHER INFORMATION: n = g, c, a, or t

<400> SEQUENCE: 109
attctgactg tatcactgaa aggctgtgta gctgtgtgac cgtaagcaag tcacttaact 60
ccagattctc agtgctgtca tctataaaca gggatgaatg aatatacacc tcagagttgt 120
taagaatcca atgagaaaat cacgggtaac ccttatataa atggttgtga aacatttcaa 180
agatacaagc atccttggcc tttgcagccc agaatcatcc ctccacattt ttcctacaat 240
ccaaccacat caagaaatga taactgctca gaaagtttat caatatttac caaaactcat 300
ggatttaaaa taaacattaa gtttctncaa taaaaaannn nnnaattcta tgccatttgt 360
actcccttga tcttcaccct atttggcaat atcaactttt ttttttgag atggagtctc 420 actttgtcac ccaggctgca ttgcacgtgg tgcaa 455

<210> SEQ ID NO 110
<211> LENGTH: 369
<212> TYPE: DNA
<213> ORGANISM: Homo sapiens

<400> SEQUENCE: 110
gtcattgctg gtcaatgaag catactaaca gaccaatctg agcagtaatt gtccttgcat 60
aagcaagatt ttttttttt ttgatggtaa tgagtgattt caaaaatacg tttaggctgg 120

-continued

```
gtatggtggt tcttgcctgt aatcccagca actttgggag gccaaggtag gaggatcact    180

cgaggccagg agttcatgac cgtcctggtc aacagagtaa gacctcgtct ctgcaaaaca    240

aaataaaata aaataaaata aaaaacttaa aaaatcatgc acctatagtc ccaactgctc    300

aagaagctga ggtgagattg cttgaggcca ggagttagag gctgcagtgt gtgattgccc    360

actgcattc                                                            369
```

```
<210> SEQ ID NO 111
<211> LENGTH: 345
<212> TYPE: DNA
<213> ORGANISM: Homo sapiens
<220> FEATURE:
<221> NAME/KEY: misc_feature
<222> LOCATION: (262)..(262)
<223> OTHER INFORMATION: n = g, c, a, or t

<400> SEQUENCE: 111

ttcttgaccc attacaatct cttctacggg caaagctgag ggactgttga catttaggga     60

tgtggccata gaattctctc tggaggagtg gcaacacctg gacattgcac agcagaattt    120

atatagaaat gtgatgttag agaactacag aaacctggcc ttcctgggta ttgctgtctc    180

taagccagac ctgatcacct gtctggaaca agggaaagag ccctggaata tgaagcgaca    240

tgagatggtg gatgaacccc cnggattgga tttttcatta ctgtgaagaa aaacactgga    300

attttgataa ggagttcttt aaatctacag gtcactttgg ataat                    345
```

```
<210> SEQ ID NO 112
<211> LENGTH: 270
<212> TYPE: DNA
<213> ORGANISM: Homo sapiens
<220> FEATURE:
<221> NAME/KEY: misc_feature
<222> LOCATION: (36)..(36)
<223> OTHER INFORMATION: n = g, c, a, or t

<400> SEQUENCE: 112

ggatttagtt gccatgtatc ttcagtttca attttncttt gtcttttcat aacattgact     60

ttttttaaga gaacagctgg tggttttata gaattccatc aatttgggtt tgtcagatta    120

ttggcttatg attagattca gttatgaatt ttggcaagga tattgcagaa gttatgatag    180

gttcttctta gtgcaactta tcacgataca catgatgtct gtttgtccca ttattggtga    240

tgttaacttc cgtaacttgc tccattgaaa                                     270
```

```
<210> SEQ ID NO 113
<211> LENGTH: 384
<212> TYPE: DNA
<213> ORGANISM: Homo sapiens

<400> SEQUENCE: 113

agtattgaaa ttcctcgagc cgctgctttt ctcactccat aattctggcc agaatttggt     60

acttaaaata ttttgtctaa aatattacaa tagctactta agtcatctcc ctgactccac    120

tctgttgtct ttcagggcgt cgtccacact gtagccaaag tgatcttata aaaacataat    180

tctaatcatg gcactcttct gcttaaaaat gttttaatgg ctttccgtta ggttaaaatt    240

taaaagtcct ttgtagcctg tgagactcta catgagttga ctccctagct tcatctttga    300

gcatcttatt tctttactta ttataccatc agttagagtt gattgttata taatccacag    360

aagtgaattc tgtccgattt aagc                                           384
```

-continued

<210> SEQ ID NO 114
<211> LENGTH: 531
<212> TYPE: DNA
<213> ORGANISM: Homo sapiens
<220> FEATURE:
<221> NAME/KEY: misc_feature
<222> LOCATION: (84)..(168)
<223> OTHER INFORMATION: n = g, c, a, or t

<400> SEQUENCE: 114
ttccctcccc agtcttagag actgatcact ggggcagagt gacattttcc cacaatgctg 60
gctcattatt ttcctcctgg aatngcaaat ccaagggaca agtggtacag cctgncaccn 120
atccagaagg ggagggaatc ccaccagagg tgccctgaaa caaagaanac aagtaacttc 180
aaaaccacat cctaaaatct ggacctgtga caggacagat ggaactctgg attgtttgat 240
tctatcagca gaacagagga aggaaatgtt ttaaaacgag attatgttat tttccccagt 300
tattatgaag ccttcctgaa atgaacttta aatatcggcc accactttca tgaggctgaa 360
tgggattcag caattaggag cgttgcaggg aagtgtggca gggcagaggt gggacaaatt 420
gcagatccct gtggggtccc ttggttaggt gacaattagt ctataaaaca cagctgtgtg 480
tgttagggag ggagtggtgt ctttaaaaag ctctgtgccc aataggaaca t 531

<210> SEQ ID NO 115
<211> LENGTH: 451
<212> TYPE: DNA
<213> ORGANISM: Homo sapiens
<220> FEATURE:
<221> NAME/KEY: misc_feature
<222> LOCATION: (125)..(368)
<223> OTHER INFORMATION: n = g, c, a, or t

<400> SEQUENCE: 115
aaccctgggt ctaggcgagc cacagggtga ggtcaaggtg agcattctgg gaacaatatt 60
tgggctcaga gggtgggttg gccaccttct gagccccacc cccgccagac ctggtgaaga 120
ggatnnnnnn nnnnnnnnnn nnnnnnnnnn nnnnnnnnnn nnnnngttgg aagaaggact 180
ggtaggttcc cctccaagcc agtcacctgt aagagtcctg tcctctgcca gactttttnn 240
nnnnnnnnnn nnnnnnnnnn nnnnnnnnnn agccctcntn nacctgaatc cagtgctcaa 300
ctgtgccccg gcaacaagac ctgggctgag gtctccctgg tagaacnnnn nnnnnnnnnn 360
nnnnnnnnat cccagtgcag tcaacagcct ggcctatagt cctgggacat gtatcttctt 420
ctttgcctta aatctgatac aagaggtcaa t 451

<210> SEQ ID NO 116
<211> LENGTH: 308
<212> TYPE: DNA
<213> ORGANISM: Homo sapiens
<220> FEATURE:
<221> NAME/KEY: misc_feature
<222> LOCATION: (170)..(283)
<223> OTHER INFORMATION: n = g, c, a, or t

<400> SEQUENCE: 116
cactgtacga gtgaggcctg tgagagctgt gtcctgcacc gctcatgctc gcccggcttt 60
ggggtcaagc agattgctac aggggtttct gataccatct gcgagccctg cccagtcggc 120
ttcttctcca atgtgtcatc tgctttcgaa aaatgtcacc cttggacaan nnnnnnnnnn 180
nnnnnnnnnn nnnnnnnnnn nnnnggcaca aacaagactg atgttgtctg tggtccccag 240
gntcggctga gagccctggt ggtgatcccc atcatcttcg ggntcctgtt tgccatcctc 300
ttggtgct 308

-continued

<210> SEQ ID NO 117
<211> LENGTH: 417
<212> TYPE: DNA
<213> ORGANISM: Homo sapiens
<220> FEATURE:
<221> NAME/KEY: misc_feature
<222> LOCATION: (62)..(392)
<223> OTHER INFORMATION: n = g, c, a, or t

<400> SEQUENCE: 117

```
ccatctgaag caagagtcca gcgttctgcc gtgtctgtcc cccaccatgc cccctacagg     60

cnnnnnnnnn nnnnnntttt ttttttttc tgtcnnnaan nnaannnnnn cntgtgggcc    120

gcccacaaca tatccttccc tcactacctg tgtgaccaag gttggcttct gttgaccttt    180

aaaaaagaaa ccctcaactc aaattgctat aattagacac ttgcttctgt cttgcntcct    240

gtctgcagct gtgaatagtc atttgactgt gactgttgcc cttagccagc cagatgcgcc    300

tgtgaaccaa agcttcgtgc acatgtgttc ccctaaaggt tggggagcct cgctgtgtct    360

tgctgttccc aggcaccacc acagcagntg nngccatact cttgtggtct ctgtgcg       417
```

<210> SEQ ID NO 118
<211> LENGTH: 495
<212> TYPE: DNA
<213> ORGANISM: Homo sapiens
<220> FEATURE:
<221> NAME/KEY: misc_feature
<222> LOCATION: (345)..(433)
<223> OTHER INFORMATION: n = g, c, a, or t

<400> SEQUENCE: 118

```
tttctgtcag gaaaacaatg ttggcctgtg ggccgcccac aacatatcct tccctcacta     60

cctgtgtgac caaggttggc ttctgttgac ctttaaaaaa gaaaccctca actcaaattg    120

ctataattag acacttgctt ctgtcttgcc tcctgtctgc agctgtgaat agtcatttga    180

ctgtgactgt tgcccttagc cagccagatg cgcctgtgaa ccaaagcttc gtgcacatgt    240

gttcccctaa aggttgggga gcctcgctgt gtcttgctgt tcccaggcac caccacagca    300

ggtgctgcca tactcttgtg gtctctgtgc gcccccccc ccccnnnacc cgtctgccaa    360

gcatgggtat gaatcgtgca cacagccatg cttcaaggcc ggggcagggg agcctgtgct    420

gatgccatcc agngcactgg gctgtgcctg gaaggcgagc cttgattgtc tgaacacata    480

aagcaaactg tccag                                                     495
```

GENE EXPRESSION PROFILES BEING PREDICTIVE FOR THE RESPONSE OF TUMORS TO PHARMACEUTICALLY EFFECTIVE COMPOUNDS

This application is a section 371 U.S. National phase application of international application no. PCT/EP2006/003421, filed Apr. 13, 2006, which claims the benefit of priority to EP application no. 05008088, filed Apr. 13, 2005 and U.S. Provisional application No. 60/670,863, filed Apr. 13, 2005.

The present invention relates to a method for providing a gene expression profile being predictive for the specific response of an individual tumor to a pharmaceutically effective compound, the use thereof, a microarray wherein the nucleotide sequences attached to the substrate consist of nucleotide sequences corresponding to the predictive genes of said gene expression profile, and a diagnostic kit containing said microarray.

Gene expression profiles reflect the relative expression level of transcription units by determining the amount of mRNA expressed. Changes in the expression levels of genes up- or down-regulated in cancerous cells can be determined when comparing the gene expression profile of highly and moderately responsive tumor tissue with the gene expression profile of resistant tumor tissue.

The so-called microarray analysis is a useful method for a highly efficient analysis of gene expression profiles. A microarray is an ordered array of genes immobilized on a planar substrate that allows the specific binding of labeled nucleic acids. Microarray technologies which can be used for analyzing gene expression profiles involve depositing nucleic acids on a solid platform in a set pattern, and hybridizing a solution of complementary nucleic acids to the nucleic acid targets. Microarray technology has been applied increasingly in this field due to its capability to illustrate the cancerous changes in the cellular behavior on a genomic level.

One of the main problems when identifying genes which predict the treatment-response of an individual tumor is the lack of a sufficient large number of different tumors being characterized for both their chemosensitivity and mRNA expression. Cell lines and cell line derived xenografts do not have enough predictive capabilities for a clinical use for evaluating genes in question. In investigating tumors only a few pharmaceutically effective compounds can be evaluated in a single tumor model and today most tumor types are treated with combination chemotherapy.

In the prior art methods for obtaining gene expression profiles of tumor material are established for one individual tumor type and are not transferable to other tumor types. Further, most of the methods known in the prior art use a two sided t-test to choose the genes differentially expressed in only two classification groups for the responsiveness of a tumor to the treatment with a pharmaceutically effective compound, i.e. sensitive and resistant. The main drawback of this method is the fact, that this procedure has a high risk of getting a large number of "false positive" genes which are differentially expressed in the different groups only by chance.

Thus, the technical problem underlying the present invention is to provide a new method for predicting the responsiveness of an individual tumor to a pharmaceutically effective compound.

The solution to the above technical problem is achieved by the embodiments characterized in the claims.

In particular, the present invention relates to a method for providing a gene expression profile being predictive for the specific response of an individual tumor to a pharmaceutically effective compound, comprising the steps of (a) xenotransplanting human tumor material of at least five different tumors into at least one suitable test animal, preferably a nude mouse, (b) determining the gene expression profiles of the resulting tumor xenografts, (c) treating said at least one test animal with a pharmaceutically effective compound, (d) evaluating the responsiveness of the tumor xenografts to the pharmaceutically effective compound, (e) identifying the gene expression profile of each of the tested tumor xenografts, and (f) determining the predictive genes in the gene expression profiles by comparing the gene expression profiles of the responsive tumors, the no-change tumors and the progressive tumors.

According to the present invention, the human tumor material being xenotransplanted into at least one suitable test animal, preferably a nude mouse, can be any human tumor material, e.g. derived from bladder, breast, colon, CNS, head and neck, liver, gallbladder, lung (small cell and non small cell), kidney, ovarian, pancreas, pleura, prostate, stomach, testicle, and uterus tumors, sarcomas, melanomas, and lymphomas. In a preferred embodiment of the present invention tumor material derived from different tumor types is transplanted into at least one nude mouse in step (a) of the above method, so that the predictive genes determined in step (f) of the above method are found in gene expression profiles of different tumor types.

In a preferred embodiment of the present invention each different tumor is xenotransplanted into one suitable test animal. For example, human tumor material of at least 15, more preferably at least 30, most preferably from 30 to 50 different tumors are each xenotransplanted into a different test animal, thereby resulting in at least 15, more preferably at least 30, most preferably from 30 to 50 different xenotransplanted test animals, preferably nude mice.

In a preferred embodiment of the present invention the human tumor material being xenotransplanted into the at least one test animal is derived from the tumor types shown in Table 2.

The term "xenografts" as used herein means patient-derived human tumor xenografts which have never been transformed into a cell line and have always been passaged directly into and through test animals, preferably nude mice. They have proven to have a high capability of predicting chemosensitivity to anti-cancer agents regarding the clinical situation of patients. For this reason they are a preferred choice for acquiring chemosensitivity data and gene expression profiles for the corresponding tumor samples.

The term "gene expression profile" as used herein refers to the relative expression of a plurality of mRNA transcripts or post-transcriptional level including protein amounts and post-translational modifications. A gene expression profile of a human tumor xenograft or a human tumor tissue reflects the amount of each mRNA transcript and/or post-transcriptional level in the starting sample. In a preferred embodiment of the present invention the gene expression profiles of the tumor xenografts is obtained using e.g. microarray techniques, PCR, Northern-analysis, etc.

The evaluation of the responsiveness of the tumor xenografts to the pharmaceutically effective compound has been carried out by determining the T/C (therapy/control) values of each tumor. The T/C value of each tumor can be determined by comparing the size of a tumor treated with a pharmaceutically effective compound (therapy) with the size of the untreated tumor (control). After all measurements at various time points are carried out the minimal value representing the best compound effect is taken for evaluation. If for example a tumor treated with a pharmaceutically effective compound has 20% of the size of an untreated tumor then the respective T/C value of the tumor treated with a pharmaceutically effective compound is 20% which equals to a tumor growth inhibition property of said pharmaceutically effective compound of 80%.

In preferred embodiments of the present invention a tumor xenograft is considered to be responsive when its T/C (therapy/control) value is e.g. less than 25%, a tumor xenograft is considered to be no-change when its T/C value is e.g. 25% or more and e.g. 42% or less, and a tumor xenograft is considered to be progressive when its T/C (therapy/control) value is e.g. more than 42%. In contrast to the prior art the present invention uses three groups which is much closer to the clinical situation than only using two.

In order to determine the predictive genes at least two of the groups selected from the group consisting of responsive, no-change, and progressive tumors, have to comprise more than one tumor as a minimum prerequisite for carrying out the Anova-test. Thus, the minimum prerequisites for determining the predictive genes are for example two responsive tumors, two no-change tumors, and one progressive tumor, or two responsive tumors, one no-change tumor, and two progressive tumors, or one responsive tumor, two no-change tumors, and two progressive tumors.

The health conditions of the animals used for xenotransplantation in the method according to the present invention is significantly impaired due to tumor growth. Accordingly, the life span of the test animals used for xenotransplantation in the method of the present invention is significantly shortened when compared to test animals not used in the method of the present invention. Therefore, the test animals either are sacrified early due to large tumor burden of the xenotransplanted tumor material or are killed after the completion of the method according to the present invention.

In a preferred embodiment of the present invention step (f) of the above method comprises a step of filtering out the relevant genes before the determination of the predictive genes.

In a further preferred embodiment of the above method step (f) comprises the steps of (i) dividing the complete set of gene expression profiles of the tumor xenografts into sub-sets, each of the sub-sets missing one of the gene expression profiles,
(ii) determining the predictive genes in each sub-set, and
(iii) obtaining the gene expression profile being predictive for the specific response of an individual tumor to the pharmaceutically effective compound by setting up the intersection of the predictive genes of all sub-sets.

In this embodiment the step of determining the predictive genes comprises a leave-one-out cross-validation. In k-fold cross-validation, the data is divided into k subsets of (approximately) equal size. The net is trained k times, each time leaving out one of the subsets from training, but using only the omitted subset to compute whatever error criterion is of interest. If k equals the sample size, this is called "leave-one-out" cross-validation.

Determining a list of predictive genes by taking the intersection of the n-gene-lists (each containing the 300 most specific genes), the risk of false positives is minimized due to the fact that "a gene by chance" would have to be a "false positive by chance" in any of the n-gene-lists, being much more improbable than using the procedures of the prior art. The "leave-out-method" of the present invention to get the predictive genes will also lead to a list of predictive genes, not biased by the tumor later left out in the cross-validation method since each gene which is only predictive because of a single tumor in the training-set will be discarded by using the intersection of the n-gene-lists.

In addition, combining an Anova test with the Fisher's Exact Test in the process of setting up the n-gene-lists is a promising way to get the 300 most specific genes for every time another tumor is left out.

It should be noted that cross-validation is quite different from the "split-sample" or "hold-out" method that is commonly used. In the split-sample method, only a single subset (the validation set) is used to estimate the generalization error, instead of k different subsets; i.e., there is no "crossing".

The distinction between cross-validation and split-sample validation is extremely important because cross-validation is markedly superior for small data sets; this fact is demonstrated dramatically by Goutte (1997) in a reply to Zhu and Rohwer (1996). For an insightful discussion of the limitations of cross-validation choice among several learning methods, see Stone (1977).

In a more preferred embodiment of the present invention the expression profile of 300 genes is determined for each sub-set when determining the predictive genes in each sub-set.

In another preferred embodiment of the present invention the gene expression profile is validated by a leave-one-out cross-validation.

The pharmaceutically effective compound according to the present invention can be any pharmaceutically effective compound known in the art and/or commercially available for the treatment and/or prevention of cancerous diseases. This includes pharmaceutically effective compounds containing agents effective for preventing tumor growth and/or metastasis or for reducing tumor size. Examples of such agents are angiogenesis inhibitors, including inhibitors of endothelial cell proliferation, e.g. Angiostatin K1-3, Avastin, Endostatin, Fumagillin, and Minocycline EGFR inhibitors, e.g. Cetuximab, and inhibitors of the biosynthesis of TNF-α, e.g. Thalidomide. Further examples of such agents are DNA intercalators/cross-linkers, e.g. Bleomycin, Chlorambucil, Melphalan and Oxaliplatin, DNA synthesis inhibitors, e.g. Aminopterin, 5-Fluoro-5'-deoxyuridine, 5-Fluorouracil, Gemcitabin, Ganciclovir, and Hydroxyurea, Capecitabin, DNA-RNA transcription regulators, topoisomerase II inhibitors, e.g. Actinomycin D, Daunorubicin, Doxorubicin, and Idarubicin, enzyme inhibitors, e.g. Curcumin, Etoposide, and Trichostatin A, agents causing demethylation of the DNA, e.g. 5-Aza-2'-deoxycytidine and 5-Azacytidine, agents having an antiproliferative effect, e.g. Cholecalciferol, microtubule inhibitors, e.g. Colchicine, Docetaxel, Nocodazole, Paclitaxel, Vinblastine, Vincristine, Vindesine, and Vinorelbin, and apoptosis causing agents, e.g. Troglitazone and Thapsigargin. In a preferred embodiment of the present invention the pharmaceutically effective compound is Avastin, a VEGF inhibitor.

In a more preferred embodiment of the present invention, the pharmaceutically effective compound is Avastin and the human tumor material being xenotransplanted into the test animals is derived from colon, non small cell lung, breast and/or renal tumors.

In a particularly preferred embodiment of the present invention the pharmaceutically effective compound is Avastin and the predictive genes of the gene expression profile obtained by the above method consists of genes characterized by SEQ. ID. No. 1 to SEQ. ID. No. 118.

In another preferred embodiment of the present invention the present invention the pharmaceutically effective compound is Avastin and the predictive genes of the gene expression profile obtained by the above method consists of genes characterized by the sequences shown in Table 3.

It is a further object of the present invention to provide a use of a gene expression profile obtained by the above method in the manufacture of a medicament carrying out an individual, tumor-specific diagnosis or treatment of a cancerous disease.

Another object of the present invention is the provision of a method for predicting the responsiveness of an individual tumor to a treatment with a pharmaceutically effective compound comprising the steps of (a) providing a gene expression profile obtained by the above method,
(b) determining the gene expression profile of the tumor to be treated, and
(c) comparing the gene expression profile of step (a) with the gene expression profile of step (b).

Using the above method it is possible to predict the prospect of success of a treatment of a patient suffering from a cancerous disease. Therefore, the above method can be used to avoid unnecessary treatment with chemotherapeutics which are a great physical and psychological burden on a tumor patient. Thus, the above method is useful for optimizing the individual treatment of a cancerous disease and avoiding the costs and serious side-effects of an ineffective chemotherapy.

In a preferred embodiment of the present invention the gene expression profiles of the tumor to be treated is obtained using microarray techniques.

The present invention also relates to the use of Avastin for a gene expression profile-dependent treatment of a cancerous disease. Avastin may e.g. be used in the treatment of a patient having a tumor, wherein the dosage of Avastin has been lowered or increased depending on the gene expression profile of said tumor when compared to the dosage which would have been used in the treatment of said patient without obtaining the gene expression profile of said tumor. In a preferred embodiment of the present invention, the gene expression profile-dependent treatment of a cancerous disease is a combination therapy comprising the use of at least one other pharmaceutically effective compound. In a more preferred embodiment of the present invention the decision whether Avastin is to be used in said combination therapy is dependent on the gene expression profile of the tumor to be treated. In a most preferred embodiment of the present invention the decision whether Avastin is to be used in said combination therapy is dependent on a gene expression profile consisting of the genes listed above.

The present invention also relates to a microarray, wherein the nucleotide sequences attached to the substrate consist of nucleotide sequences corresponding to the predictive genes of a gene expression profile obtained by the method for providing a gene expression profile being predictive for the specific response of an individual tumor to a pharmaceutically effective compound of the present invention.

The term "microarray" as used herein means any arrangement of biomolecules, such as nucleic acids, antibodies, preferably oligonucleotides in addressable locations on a substrate resulting in a so-called "biochip". The substrate may be any substrate suitable for use in a microarray known in the art, like e.g. membranes, glass, plastic, silicon wafers, and metal alloys. The information obtained when using microarray techniques can also be obtained by other methods known in the art for determining gene expression profiles, e.g. PCR, Northern-analysis, etc.

It is a further object of the present invention to provide a diagnostic kit containing the above microarray.

The figure shows:

Figure 1:
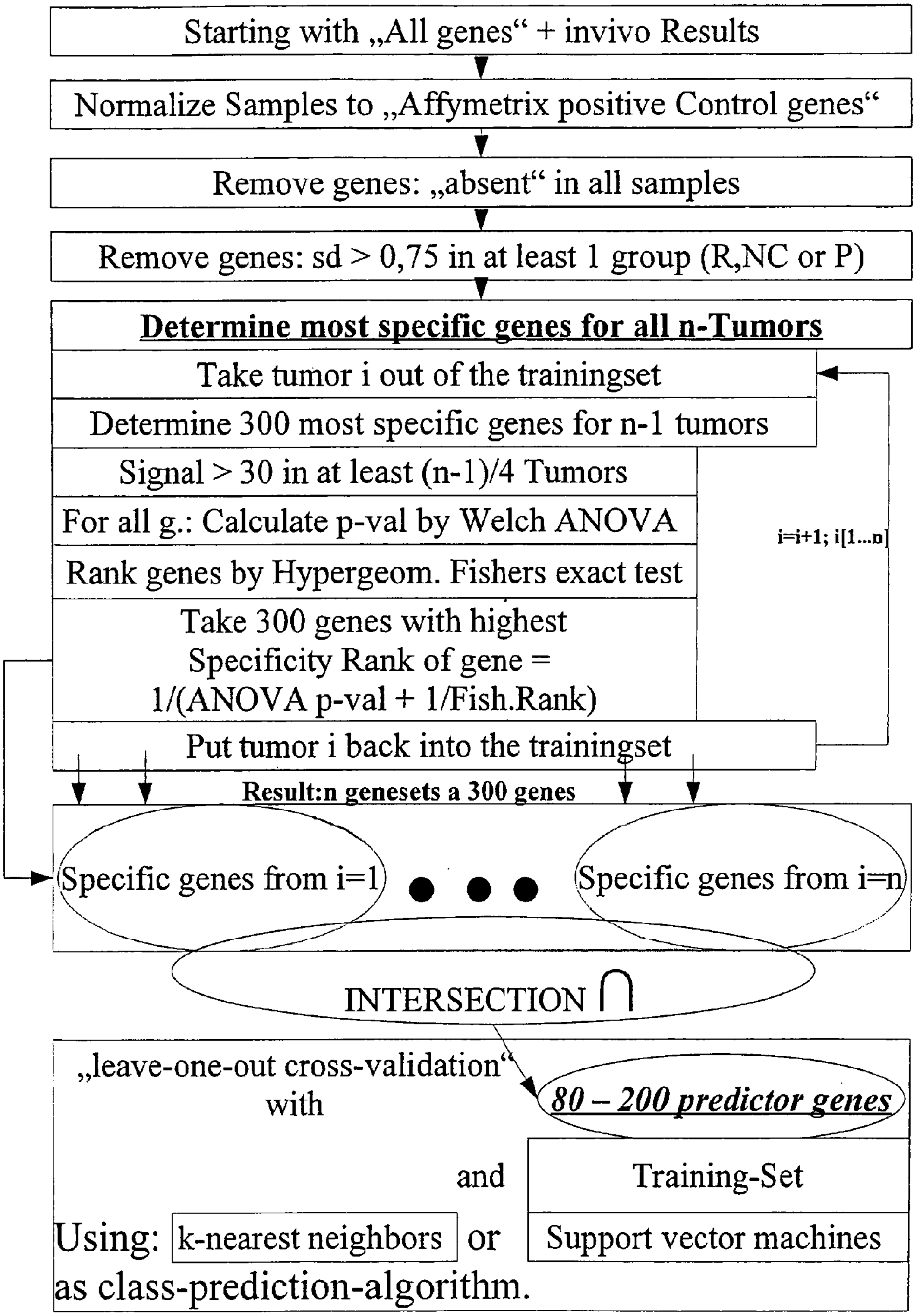
FIG. 1 shows a flowchart which gives an example of a preferred embodiment how the method for providing a gene expression profile being predictive for the specific response of an individual tumor to a pharmaceutically effective compound according to the present invention may be carried out. sd: standard deviation.

The present invention will now be further illustrated in the following examples without being limited thereto.

EXAMPLES

Example 1

The activity of Avastin has been tested against a set of 46 of patient derived tumor xenografts in nude mice derived from different tumor types preferably known to have the chance of being responsive to Avastin e.g. colon, non small cell lung, renal, or breast cancers. The gene expression profiles for the same tumors have been obtained by using the Affymetrix gene-expression Arrays HG-U133A/B and HG-U 133 Plus 2.0. These gene expression arrays determine the expression of about 34,000 genes.

For identifying genes, being predictive for the specific response of an individual tumor to a specific compound, the following steps are carried out, starting with a list of all gene expressions determined by the arrays:

(1) Every gene expression that has a value of lower than 0.01 was set to 0.01 to make natural log transformation for further statistical analysis possible.
(2) Every gene expression on a single chip was normalized to the median of the "not absent" genes being described by Affymetrix as "positive control genes" to make an inter-chip comparison possible and eliminate non-biological variances.
(3) All genes with an "absent" status in all tumor samples were removed from the list.
(4) All genes with a standard deviation of greater or equal 0.75 in at least one of the classification-groups (R, NC, P) were removed because they are not supposed to be predictive for the groups.

After these "quality filtering" steps the main determination of predictive genes is carried out:

(1) The training-set of the 46 tumor samples is divided into 46 sub-training-sets, each of these sub-training-sets missing one, different tumor.
(2) A list of 300 genes with the highest classification group specificity is determined for each sub-training-set.

Each gene in this list has to fulfill the following requirements:

- having a raw signal of at least 30 in at least (46−1)/4 which equals about 11 tumor samples, and therefore being expressed in at least ¼ of all tumors above a critical level of background.
- having a "specificity rank" of ≤300 with the specificity rank defined by:
- specificity rank=1/(p-val+1/Fish.Rank) with
- p-val determined by a Welch ANOVA test across the classification-groups
- Fish.Rank determined by the Hypergeometric Fisher's Exact Test.

The procedure carried out for all 46 sub-training-sets, results in 46 lists of 300 genes respectively. By setting up a gene-list containing the intersection of all these 300 gene containing lists, the result is a set of genes which were specific in all sub-training-sets and is not dependent on a single tumor sample. This step minimizes the risk of "false positive" genes, which otherwise could have been wrongly identified as being specific/predictive.

The final outcome is a list of 118 gene expression in 46 tumors (Table 1, horizontal: different tumors tested, vertical: Affymetrix genes) which is predictive for the response of these tumors to Avastin. The tumor types used determining said gene profile are shown in Table 2 and the sequences of the predictive genes are shown in Table 3. The gene signature is validated by a "leave-one-out cross-validation" using e.g. either a "k-nearest neighbours" or a "support vector machine" classification algorithm.

Figure 2:
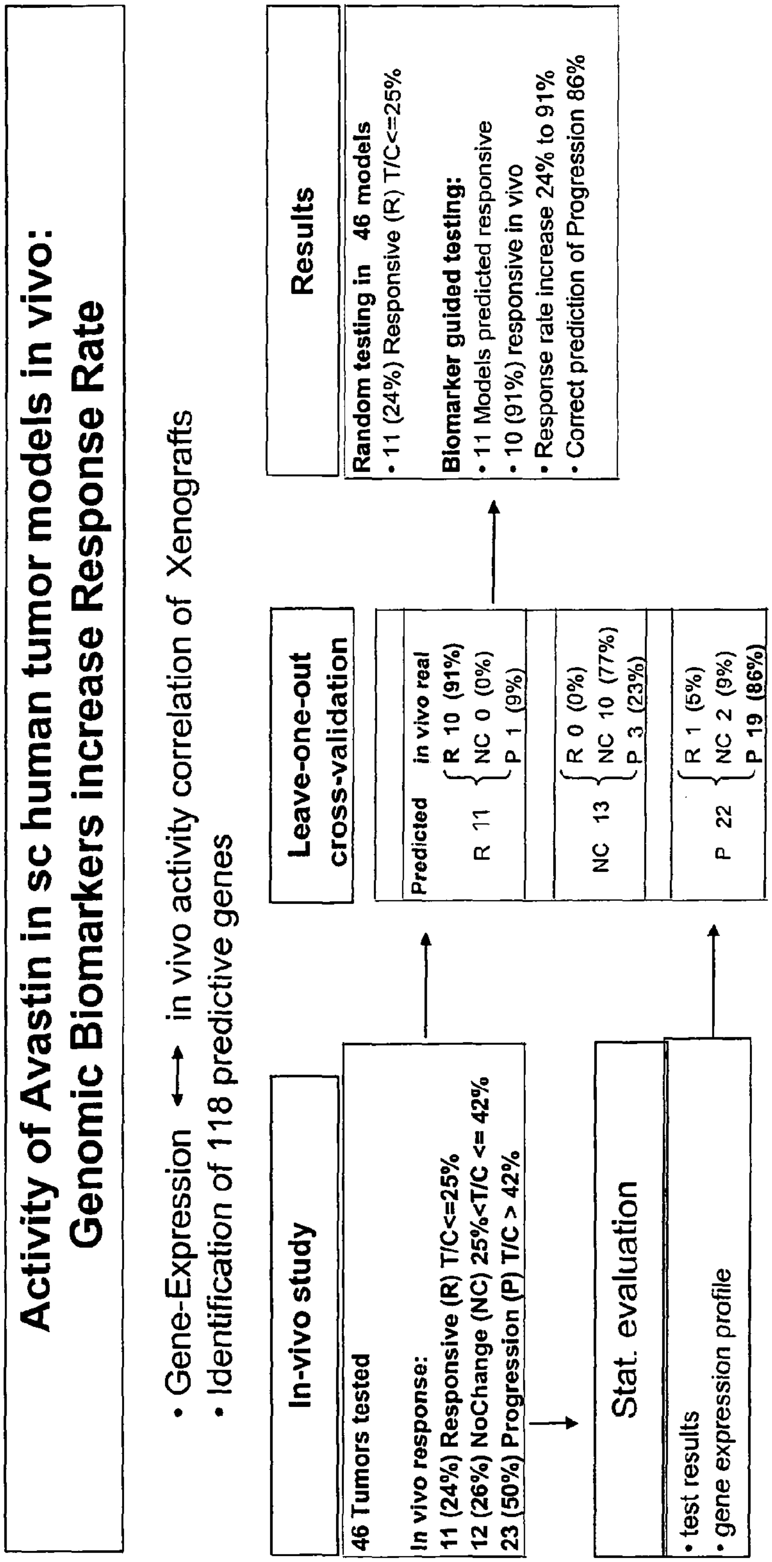
FIG. 2 shows an overview of a preferred embodiment how the method for providing a gene expression profile being predictive for the specific response of an individual tumor to Avastin as described in Example 1 may be obtained.

After validation, the gene expression profile can be used for further prospective validation or to predict tumor samples with unknown chemosensitivity. Using e.g. a "support vector machine" of order 1 for a "leave-one-out cross-validation" showed that the detected genes have a very good ability to discriminate the tumors into the three classification groups and predict tumor response to Avastin (FIG. 2).

Methods

It should be noticed that k-nearest neighbours and support vector machines are available in the prior art.

A. Welch Anova (Parametric)

Let i index over the G groups formed by distinct levels of the comparison parameter.

Let Xik be the expression values, with k running over the replicates for each situation, interpreted according to the current interpretation (ratio, log of ratio, fold change).

Let:

Ni=the number of non-missing data values for each group, $$\overline{X}_i = 1/N_i \sum_{k-1}^{N_i} X_{ik}$$

be the group means, and $$SS_i = \sum_{k-1}^{N_i} (X_{ik} - \overline{X}_i)^2$$

be the within-group sum of squares.

In all calculations, missing values (No Data) or (NaN) are left out of the sums, not propagated. If any of the Ni are zero, drop that parameter level from the analysis, and readjust G accordingly. If G is not at least 2, exit (p-value=1).

First, it has to be checked that each group has Ni greater than or equal to 2 and SSi greater than 0. If not, remove it from consideration and recompute G. If G is not at least 2, exit (p-value=1). (This reflects the more stringent requirements of not assuming the variances equal—if the variance estimate is pooled, replicates are only needed for at least one group, if variances are separately estimated then replicates are needed for each group.) Then compute:

$$w_i = N_i\left(\frac{N_i - 1}{SS_i}\right)$$

the group weights $$W = \sum_{i-1}^{G} w_i$$

the sum of weights $$\tilde{X} = \frac{\sum_{i-1}^{G} w_i \overline{X}_i}{W}$$

the weighted mean $BSS=\Sigma w_i(\overline{X}_i-\tilde{X})^2$ the between-groups sum of squares $d_1=G-1$ the numerator degrees of freedom $BMS=BSS/d_1$ the between groups mean square $$Z = \frac{1}{G^2-1}\sum_{i=1}^{G}\left(1 = \frac{w_i}{W}\right)^2 \Big/ (N_i = 1)$$

$$d_2 = \frac{1}{3Z}$$

the denominator degrees of freedom if $d_2$ is not greater than zero, then exit (p-value=1).

WMS=1+2(G−2)Z the within-group. mean square

W=BMS/WMS the test statistic

The (approximate) p-value is calculated by looking up W in the upper tail probability of an F distribution with d1 and d2 degrees of freedom. Note that d2 will not, in general, be an integer.

B. Fisher's Exact Test:

Fisher's Exact Test looks for an association between expression level and class membership. Each gene is tested for its ability to discriminate between the classes. Genes with the lowest p-values are kept for the subsequent calculations.

In this method, all the measurements for a given gene are ordered according to their normalized expression levels. For each class (parameter value), the predictor places a mark in the list where the relative abundance of the class on one side of the mark is the highest in comparison to the other side of the mark. The genes that are most accurately segregated by these markers are considered to be the most predictive. A list of the most predictive genes is made for each class and an equal number of genes (lowest p-value using Fisher's Exact Test) are taken from each list.

TABLE 1

| Systematic Name | CXF_264, Avastin_p NC normalized | CXF_975, Avastin_p NC normalized | LXFA_297, Avastin_p NC normalized | LXFA_923, Avastin_p NC normalized | LXFE_409, Avastin_p NC normalized | LXFL_430, Avastin_p NC normalized | MAXF_1322, Avastin_p NC normalized | MAXF_1384, Avastin_p NC normalized | MAXF_401, Avastin_p NC normalized | MAXF_583, Avastin_p NC normalized |
|---|---|---|---|---|---|---|---|---|---|---|
| 200076_s_at | 0.241 | 0.199 | 0.253 | 0.159 | 0.169 | 0.19 | 0.169 | 0.193 | 0.175 | 0.236 |
| 200631_s_at | 0.698 | 0.794 | 0.426 | 0.48 | 0.701 | 0.285 | 1.46 | 0.416 | 1.151 | 0.662 |
| 201722_s_at | 0.0751 | 0.0723 | 0.102 | 0.197 | 0.0484 | 0.0508 | 0.0817 | 0.0681 | 0.101 | 0.0659 |
| 201919_at | 0.223 | 0.242 | 0.265 | 0.261 | 0.244 | 0.184 | 0.195 | 0.273 | 0.242 | 0.353 |
| 202333_s_at | 0.0582 | 0.0986 | 0.11 | 0.106 | 0.0479 | 0.0527 | 0.107 | 0.113 | 0.0493 | 0.0931 |
| 202758_s_at | 0.0953 | 0.0864 | 0.0666 | 0.0295 | 0.101 | 0.103 | 0.0532 | 0.161 | 0.0683 | 0.105 |
| 203092_at | 0.0634 | 0.0387 | 0.0392 | 0.01 | 0.0549 | 0.0703 | 0.0884 | 0.0426 | 0.0422 | 0.0821 |
| 203846_at | 0.0428 | 0.0586 | 0.0497 | 0.0426 | 0.0458 | 0.0351 | 0.0704 | 0.0662 | 0.0626 | 0.0748 |
| 205042_at | 0.0707 | 0.198 | 0.0601 | 0.0437 | 0.0641 | 0.039 | 0.01 | 0.0433 | 0.0542 | 0.0759 |
| 205046_at | 0.0873 | 0.0218 | 0.034 | 0.0273 | 0.0488 | 0.041 | 0.0605 | 0.0452 | 0.0746 | 0.0492 |
| 205105_at | 0.0537 | 0.117 | 0.0693 | 0.0541 | 0.0305 | 0.01 | 0.0432 | 0.0369 | 0.01 | 0.0256 |
| 205481_at | 0.01 | 0.01 | 0.01 | 0.01 | 0.0248 | 0.01 | 0.0558 | 0.0255 | 0.0443 | 0.0596 |
| 206003_at | 0.0311 | 0.01 | 0.01 | 0.01 | 0.0423 | 0.01 | 0.01 | 0.01 | 0.0239 | 0.01 |
| 208369_s_at | 0.0444 | 0.0288 | 0.0353 | 0.0372 | 0.0571 | 0.0312 | 0.0784 | 0.0426 | 0.0225 | 0.045 |
| 208848_at | 0.0517 | 0.0678 | 0.0562 | 0.0683 | 0.078 | 0.0488 | 0.0458 | 0.0592 | 0.0218 | 0.0424 |
| 208951_at | 0.0759 | 0.0819 | 0.0431 | 0.0869 | 0.0946 | 0.0839 | 0.0764 | 0.101 | 0.0788 | 0.186 |
| 209161_at | 0.122 | 0.097 | 0.0784 | 0.0574 | 0.114 | 0.0898 | 0.205 | 0.0916 | 0.27 | 0.101 |
| 209758_s_at | 0.01 | 0.01 | 0.0222 | 0.0246 | 0.01 | 0.01 | 0.01 | 0.01 | 0.01 | 0.01 |
| 211974_x_at | 0.235 | 0.249 | 0.278 | 0.297 | 0.216 | 0.236 | 0.325 | 0.256 | 0.373 | 0.243 |
| 211976_at | 0.063 | 0.162 | 0.0588 | 0.167 | 0.13 | 0.162 | 0.0784 | 0.0363 | 0.157 | 0.105 |
| 212394_at | 0.0242 | 0.01 | 0.01 | 0.0241 | 0.01 | 0.0215 | 0.01 | 0.01 | 0.01 | 0.01 |
| 213677_s_at | 0.0848 | 0.107 | 0.0849 | 0.116 | 0.14 | 0.0918 | 0.163 | 0.183 | 0.167 | 0.179 |
| 214086_s_at | 0.0792 | 0.0362 | 0.0876 | 0.0782 | 0.0736 | 0.0859 | 0.0751 | 0.171 | 0.109 | 0.21 |
| 214585_s_at | 0.0913 | 0.133 | 0.247 | 0.178 | 0.189 | 0.135 | 0.161 | 0.115 | 0.196 | 0.17 |
| 214672_at | 0.044 | 0.0448 | 0.0771 | 0.0481 | 0.0893 | 0.0703 | 0.0751 | 0.0675 | 0.0845 | 0.0973 |
| 214844_s_at | 0.01 | 0.01 | 0.0967 | 0.01 | 0.0231 | 0.0293 | 0.391 | 0.118 | 0.0366 | 0.0371 |
| 217797_at | 0.207 | 0.554 | 0.947 | 0.458 | 0.422 | 0.355 | 0.595 | 0.458 | 0.726 | 0.241 |
| 217895_at | 0.0917 | 0.135 | 0.0954 | 0.113 | 0.124 | 0.123 | 0.095 | 0.122 | 0.0823 | 0.137 |
| 218625_at | 0.0574 | 0.222 | 0.0222 | 0.01 | 0.01 | 0.0332 | 0.118 | 0.01 | 0.0683 | 0.0439 |
| 218768_at | 0.253 | 0.155 | 0.169 | 0.223 | 0.304 | 0.289 | 0.174 | 0.148 | 0.371 | 0.545 |
| 218818_at | 0.01 | 0.01 | 0.0287 | 0.01 | 0.01 | 0.01 | 0.0226 | 0.0248 | 0.01 | 0.01 |
| 218998_at | 0.0957 | 0.156 | 0.0745 | 0.059 | 0.0937 | 0.0605 | 0.15 | 0.0757 | 0.0992 | 0.207 |
| 219595_at | 0.0319 | 0.0326 | 0.0484 | 0.0317 | 0.0532 | 0.0527 | 0.0332 | 0.0344 | 0.0324 | 0.0957 |
| 219906_at | 0.0372 | 0.0509 | 0.0366 | 0.0339 | 0.0309 | 0.0351 | 0.0292 | 0.0331 | 0.0514 | 0.0633 |
| 221214_s_at | 0.0469 | 0.0362 | 0.0209 | 0.0241 | 0.0427 | 0.0293 | 0.0485 | 0.0255 | 0.0471 | 0.0434 |
| 221249_s_at | 0.038 | 0.0774 | 0.0849 | 0.064 | 0.261 | 0.0781 | 0.0578 | 0.0993 | 0.0317 | 0.0717 |
| 222587_s_at | 0.0831 | 0.0866 | 0.143 | 0.062 | 0.0315 | 0.0293 | 0.0233 | 0.0244 | 0.0305 | 0.01 |
| 222612_at | 0.0212 | 0.0881 | 0.042 | 0.101 | 0.0722 | 0.0976 | 0.0934 | 0.0952 | 0.0722 | 0.156 |
| 222775_s_at | 0.0993 | 0.104 | 0.106 | 0.121 | 0.0848 | 0.137 | 0.0989 | 0.0893 | 0.175 | 0.103 |
| 222807_at | 0.0254 | 0.0697 | 0.0395 | 0.0784 | 0.0951 | 0.0781 | 0.0975 | 0.0685 | 0.101 | 0.122 |
| 222906_at | 0.154 | 0.131 | 0.17 | 0.126 | 0.246 | 0.169 | 0.211 | 0.217 | 0.249 | 0.133 |
| 223175_s_at | 0.0882 | 0.0637 | 0.0642 | 0.0767 | 0.111 | 0.0846 | 0.0687 | 0.0673 | 0.13 | 0.0861 |
| 223197_s_at | 0.194 | 0.194 | 0.0913 | 0.22 | 0.117 | 0.111 | 0.187 | 0.149 | 0.127 | 0.17 |
| 223206_s_at | 0.264 | 0.22 | 0.178 | 0.127 | 0.198 | 0.163 | 0.187 | 0.171 | 0.109 | 0.169 |
| 223448_x_at | 0.373 | 0.247 | 0.183 | 0.193 | 0.214 | 0.416 | 0.184 | 0.209 | 0.214 | 0.349 |
| 223470_at | 0.0942 | 0.182 | 0.18 | 0.145 | 0.0853 | 0.0911 | 0.169 | 0.327 | 0.181 | 0.225 |

TABLE 1-continued

| | | | | | | | | | | |
|---|---|---|---|---|---|---|---|---|---|---|
| 223518_at | 0.0823 | 0.0816 | 0.0938 | 0.105 | 0.115 | 0.14 | 0.0934 | 0.11 | 0.0844 | 0.112 |
| 223528_s_at | 0.109 | 0.109 | 0.197 | 0.251 | 0.157 | 0.296 | 0.159 | 0.233 | 0.176 | 0.239 |
| 223570_at | 0.0526 | 0.0329 | 0.0518 | 0.0457 | 0.134 | 0.0976 | 0.0947 | 0.109 | 0.0722 | 0.122 |
| 224473_x_at | 0.1 | 0.1 | 0.133 | 0.107 | 0.159 | 0.202 | 0.0769 | 0.128 | 0.16 | 0.132 |
| 224721_at | 0.135 | 0.0996 | 0.151 | 0.151 | 0.0962 | 0.322 | 0.122 | 0.19 | 0.156 | 0.228 |
| 225025_at | 0.0942 | 0.0916 | 0.114 | 0.0936 | 0.0796 | 0.15 | 0.0769 | 0.0777 | 0.127 | 0.0738 |
| 225097_at | 0.0509 | 0.101 | 0.111 | 0.0502 | 0.0825 | 0.0813 | 0.325 | 0.366 | 0.0742 | 0.209 |
| 225506_at | 0.193 | 0.0966 | 0.153 | 0.118 | 0.132 | 0.12 | 0.13 | 0.0986 | 0.215 | 0.118 |
| 225554_s_at | 0.246 | 0.272 | 0.43 | 0.297 | 0.407 | 0.475 | 0.254 | 0.263 | 0.419 | 0.436 |
| 225584_at | 0.0517 | 0.0548 | 0.0617 | 0.0671 | 0.0613 | 0.0456 | 0.0536 | 0.0383 | 0.0539 | 0.0634 |
| 225841_at | 0.266 | 0.2 | 0.563 | 0.245 | 0.325 | 0.244 | 0.133 | 0.209 | 0.103 | 0.295 |
| 225947_at | 0.516 | 0.434 | 0.434 | 0.453 | 0.563 | 0.394 | 0.389 | 0.256 | 0.371 | 0.517 |
| 226124_at | 0.138 | 0.132 | 0.202 | 0.129 | 0.0739 | 0.124 | 0.115 | 0.157 | 0.13 | 0.205 |
| 226139_at | 0.0577 | 0.0692 | 0.0592 | 0.0632 | 0.0567 | 0.0651 | 0.0577 | 0.0847 | 0.0824 | 0.0634 |
| 226308_at | 0.0509 | 0.0229 | 0.0222 | 0.01 | 0.0928 | 0.0423 | 0.0604 | 0.0348 | 0.0478 | 0.0918 |
| 226428_at | 0.154 | 0.107 | 0.123 | 0.0575 | 0.245 | 0.133 | 0.132 | 0.169 | 0.176 | 0.276 |
| 226616_s_at | 0.479 | 0.389 | 0.432 | 0.608 | 0.419 | 0.452 | 0.312 | 0.202 | 0.369 | 0.397 |
| 226651_at | 0.0679 | 0.0324 | 0.0247 | 0.122 | 0.0309 | 0.0911 | 0.144 | 0.173 | 0.151 | 0.127 |
| 226693_at | 0.115 | 0.0901 | 0.131 | 0.142 | 0.121 | 0.0813 | 0.0879 | 0.216 | 0.127 | 0.158 |
| 226749_at | 0.173 | 0.193 | 0.432 | 0.251 | 0.204 | 0.29 | 0.162 | 0.194 | 0.377 | 0.29 |
| 226810_at | 0.117 | 0.148 | 0.0913 | 0.0688 | 1.081 | 0.0618 | 1.545 | 0.634 | 0.934 | 1.86 |
| 226839_at | 0.129 | 0.144 | 0.104 | 0.0665 | 0.171 | 0.133 | 0.147 | 0.152 | 0.149 | 0.144 |
| 226917_s_at | 0.288 | 0.367 | 0.333 | 0.385 | 0.197 | 0.673 | 0.441 | 0.375 | 0.419 | 0.306 |
| 227181_at | 0.0509 | 0.0488 | 0.0617 | 0.0632 | 0.0573 | 0.0878 | 0.135 | 0.087 | 0.15 | 0.195 |
| 227412_at | 0.078 | 0.0582 | 0.0889 | 0.0293 | 0.0704 | 0.0521 | 0.0426 | 0.0928 | 0.0956 | 0.123 |
| 227427_at | 0.0365 | 0.0219 | 0.0296 | 0.0242 | 0.0366 | 0.0748 | 0.0302 | 0.029 | 0.131 | 0.0322 |
| 227472_at | 0.0322 | 0.0363 | 0.0518 | 0.0344 | 0.0292 | 0.0423 | 0.01 | 0.0244 | 0.0376 | 0.0322 |
| 227603_at | 0.084 | 0.365 | 0.16 | 0.0885 | 0.145 | 0.277 | 0.305 | 0.194 | 0.167 | 0.426 |
| 227810_at | 0.148 | 0.22 | 0.141 | 0.151 | 0.175 | 0.0878 | 0.15 | 0.0859 | 0.135 | 0.212 |
| 227921_at | 0.268 | 0.308 | 0.118 | 0.066 | 0.238 | 0.208 | 0.288 | 0.393 | 0.672 | 0.541 |
| 228286_at | 0.0509 | 0.0587 | 0.0592 | 0.0541 | 0.059 | 0.0553 | 0.0687 | 0.0569 | 0.0793 | 0.0871 |
| 228650_at | 0.102 | 0.134 | 0.146 | 0.104 | 0.114 | 0.221 | 0.0961 | 0.178 | 0.19 | 0.168 |
| 228736_at | 0.0458 | 0.0488 | 0.01 | 0.0265 | 0.01 | 0.0228 | 0.0275 | 0.0232 | 0.0264 | 0.01 |
| 228930_at | 0.0993 | 0.191 | 0.079 | 0.216 | 0.142 | 0.153 | 0.113 | 0.124 | 0.117 | 0.11 |
| 229001_at | 0.0763 | 0.0483 | 0.0518 | 0.01 | 0.0567 | 0.0488 | 0.0426 | 0.175 | 0.0885 | 0.19 |
| 229035_s_at | 0.111 | 0.172 | 0.126 | 0.121 | 0.0773 | 0.114 | 0.146 | 0.121 | 0.162 | 0.135 |
| 229384_at | 0.101 | 0.115 | 0.0839 | 0.0806 | 0.0744 | 0.0846 | 0.173 | 0.0708 | 0.114 | 0.151 |
| 229421_s_at | 0.01 | 0.01 | 0.042 | 0.01 | 0.01 | 0.0228 | 0.0261 | 0.01 | 0.01 | 0.01 |
| 229534_at | 0.0789 | 0.0244 | 0.136 | 0.0722 | 0.0344 | 0.0553 | 0.0247 | 0.0209 | 0.0437 | 0.0303 |
| 229570_at | 0.039 | 0.0448 | 0.0543 | 0.0288 | 0.0304 | 0.01 | 0.0288 | 0.0534 | 0.0874 | 0.0303 |
| 230048_at | 0.01 | 0.01 | 0.01 | 0.01 | 0.0223 | 0.0228 | 0.0302 | 0.01 | 0.01 | 0.01 |
| 230791_at | 0.118 | 0.144 | 0.01 | 0.0316 | 0.404 | 0.0456 | 2.72 | 1.519 | 0.215 | 0.775 |
| 230922_x_at | 0.0314 | 0.0388 | 0.037 | 0.0276 | 0.0412 | 0.039 | 0.0522 | 0.0336 | 0.0417 | 0.0454 |
| 230983_at | 0.0288 | 0.0314 | 0.0272 | 0.0276 | 0.0229 | 0.0325 | 0.0302 | 0.0313 | 0.01 | 0.0275 |
| 231271_x_at | 0.197 | 0.196 | 0.22 | 0.203 | 0.287 | 0.238 | 0.255 | 0.328 | 0.24 | 0.287 |
| 232524_x_at | 0.221 | 0.316 | 0.353 | 0.289 | 0.162 | 0.446 | 0.283 | 0.308 | 0.341 | 0.173 |
| 232527_at | 0.01 | 0.0672 | 0.0666 | 0.0592 | 0.0647 | 0.0586 | 0.114 | 0.0812 | 0.0996 | 0.0748 |
| 233214_at | 0.146 | 0.194 | 0.114 | 0.109 | 0.114 | 0.107 | 0.119 | 0.153 | 0.165 | 0.0559 |
| 233302_at | 0.0246 | 0.0677 | 0.0222 | 0.0209 | 0.083 | 0.0358 | 0.01 | 0.123 | 0.01 | 0.0511 |
| 233429_at | 0.01 | 0.0334 | 0.0321 | 0.0383 | 0.0309 | 0.0325 | 0.0247 | 0.0278 | 0.0386 | 0.0303 |
| 233440_at | 0.0373 | 0.0418 | 0.0296 | 0.0361 | 0.0613 | 0.0488 | 0.0522 | 0.0685 | 0.0458 | 0.0322 |
| 233493_at | 0.0212 | 0.0264 | 0.0247 | 0.01 | 0.01 | 0.01 | 0.0233 | 0.0267 | 0.0244 | 0.01 |
| 233599_at | 0.01 | 0.01 | 0.01 | 0.01 | 0.01 | 0.01 | 0.01 | 0.01 | 0.01 | 0.01 |

TABLE 1-continued

| | | | | | | | | | | |
|---|---|---|---|---|---|---|---|---|---|---|
| 234735_s_at | 0.114 | 0.104 | 0.188 | 0.0795 | 0.145 | 0.111 | 0.092 | 0.171 | 0.198 | 0.114 |
| 235363_at | 0.0619 | 0.0682 | 0.0247 | 0.044 | 0.138 | 0.0846 | 0.194 | 0.0777 | 0.13 | 0.206 |
| 235467_s_at | 0.01 | 0.0279 | 0.042 | 0.0265 | 0.0767 | 0.0325 | 0.0453 | 0.029 | 0.0407 | 0.0426 |
| 235634_at | 0.0339 | 0.0353 | 0.0444 | 0.0412 | 0.0401 | 0.0748 | 0.0343 | 0.0453 | 0.0386 | 0.0322 |
| 236312_at | 0.0696 | 0.0568 | 0.01 | 0.0231 | 0.0452 | 0.0325 | 0.0934 | 0.029 | 0.0712 | 0.0303 |
| 236875_at | 0.01 | 0.01 | 0.0222 | 0.01 | 0.0212 | 0.0228 | 0.022 | 0.01 | 0.0224 | 0.01 |
| 237023_at | 0.0322 | 0.0548 | 0.0395 | 0.0502 | 0.0401 | 0.0488 | 0.0481 | 0.0441 | 0.0702 | 0.0398 |
| 239496_at | 0.01 | 0.0358 | 0.0222 | 0.0564 | 0.0355 | 0.0456 | 0.081 | 0.0801 | 0.0681 | 0.127 |
| 240130_at | 0.01 | 0.01 | 0.0346 | 0.0231 | 0.0206 | 0.0293 | 0.022 | 0.0209 | 0.0224 | 0.01 |
| 241395_at | 0.0424 | 0.0468 | 0.0346 | 0.0355 | 0.0281 | 0.0553 | 0.0549 | 0.0302 | 0.0376 | 0.0483 |
| 242171_at | 0.0254 | 0.01 | 0.01 | 0.01 | 0.0435 | 0.0358 | 0.081 | 0.0383 | 0.0427 | 0.0549 |
| 242602_x_at | 0.0543 | 0.0617 | 0.0592 | 0.0519 | 0.0687 | 0.0618 | 0.0728 | 0.0313 | 0.0824 | 0.0682 |
| 242606_at | 0.0509 | 0.0363 | 0.037 | 0.0333 | 0.01 | 0.026 | 0.01 | 0.022 | 0.01 | 0.01 |
| 243003_at | 0.0611 | 0.113 | 0.0617 | 0.156 | 0.131 | 0.12 | 0.141 | 0.168 | 0.108 | 0.224 |
| 243185_at | 0.0229 | 0.0428 | 0.01 | 0.0242 | 0.01 | 0.039 | 0.01 | 0.01 | 0.01 | 0.01 |
| 31826_at | 0.0715 | 0.0701 | 0.115 | 0.0634 | 0.0767 | 0.0625 | 0.146 | 0.0866 | 0.0795 | 0.0895 |
| 35150_at | 0.0388 | 0.0461 | 0.0653 | 0.0601 | 0.0898 | 0.0527 | 0.0458 | 0.0261 | 0.0303 | 0.0398 |
| 64474_g_at | 0.0816 | 0.0602 | 0.0274 | 0.0317 | 0.058 | 0.0332 | 0.0299 | 0.0795 | 0.0239 | 0.046 |
| 91617_at | 0.0436 | 0.0387 | 0.01 | 0.0388 | 0.0471 | 0.0898 | 0.0472 | 0.0433 | 0.0422 | 0.0576 |

| Systematic Name | MAXF_MX1, Avastin_p NC normalized | RXF_1393, Avastin_p NC normalized | CXF_1044, Avastin_p P normalized | CXF_1753, Avastin_p P normalized | CXF_1784, Avastin_p P normalized | CXF_280, Avastin_p P normalized | CXF_609, Avastin_p P normalized | CXF_676, Avastin_p P normalized | CXF_94LX, Avastin_p P normalized | LXFA_1012, Avastin_p P normalized |
|---|---|---|---|---|---|---|---|---|---|---|
| 200076_s_at | 0.179 | 0.212 | 0.0712 | 0.132 | 0.104 | 0.177 | 0.153 | 0.0847 | 0.142 | 0.102 |
| 200631_s_at | 0.664 | 0.227 | 0.573 | 0.753 | 0.571 | 0.954 | 0.495 | 0.611 | 0.727 | 0.653 |
| 201722_s_at | 0.0975 | 0.076 | 0.18 | 0.216 | 0.147 | 0.15 | 0.349 | 0.169 | 0.16 | 0.301 |
| 201919_at | 0.222 | 0.404 | 0.25 | 0.303 | 0.214 | 0.213 | 0.203 | 0.234 | 0.261 | 0.213 |
| 202333_s_at | 0.0499 | 0.105 | 0.319 | 0.138 | 0.293 | 0.0834 | 0.126 | 0.371 | 0.0787 | 0.333 |
| 202758_s_at | 0.0983 | 0.0962 | 0.0582 | 0.0463 | 0.0672 | 0.055 | 0.0406 | 0.0635 | 0.0416 | 0.0428 |
| 203092_at | 0.0735 | 0.0414 | 0.0462 | 0.0385 | 0.0318 | 0.0461 | 0.0215 | 0.01 | 0.0362 | 0.0358 |
| 203846_at | 0.044 | 0.0523 | 0.0442 | 0.0687 | 0.0448 | 0.0688 | 0.0315 | 0.0375 | 0.0597 | 0.0508 |
| 205042_at | 0.01 | 0.0743 | 0.248 | 0.322 | 0.124 | 0.098 | 0.0832 | 0.327 | 0.01 | 0.117 |
| 205046_at | 0.0822 | 0.054 | 0.01 | 0.0336 | 0.0385 | 0.0357 | 0.01 | 0.0317 | 0.0647 | 0.0497 |
| 205105_at | 0.0279 | 0.0785 | 0.0874 | 0.0981 | 0.0594 | 0.0469 | 0.0695 | 0.18 | 0.0801 | 0.0598 |
| 205481_at | 0.01 | 0.0397 | 0.01 | 0.01 | 0.01 | 0.01 | 0.01 | 0.01 | 0.01 | 0.01 |
| 206003_at | 0.01 | 0.0422 | 0.01 | 0.01 | 0.0346 | 0.0254 | 0.01 | 0.0318 | 0.024 | 0.139 |
| 208369_s_at | 0.0574 | 0.0641 | 0.0238 | 0.0336 | 0.0291 | 0.01 | 0.0272 | 0.01 | 0.0258 | 0.01 |
| 208848_at | 0.0425 | 0.113 | 0.0398 | 0.0764 | 0.165 | 0.0277 | 0.0413 | 0.0586 | 0.0547 | 0.0554 |
| 208951_at | 0.116 | 0.105 | 0.0391 | 0.0708 | 0.0508 | 0.035 | 0.0289 | 0.0672 | 0.052 | 0.14 |
| 209161_at | 0.081 | 0.043 | 0.0754 | 0.0939 | 0.138 | 0.137 | 0.0591 | 0.0698 | 0.0968 | 0.128 |
| 209758_s_at | 0.01 | 0.0338 | 0.0258 | 0.0231 | 0.01 | 0.01 | 0.01 | 0.01 | 0.01 | 0.0265 |
| 211974_x_at | 0.131 | 0.44 | 0.0987 | 0.407 | 0.149 | 0.14 | 0.171 | 0.179 | 0.204 | 0.114 |
| 211976_at | 0.0967 | 0.12 | 0.0933 | 0.144 | 0.132 | 0.129 | 0.106 | 0.155 | 0.199 | 0.177 |
| 212394_at | 0.01 | 0.0287 | 0.01 | 0.0224 | 0.01 | 0.01 | 0.01 | 0.0202 | 0.01 | 0.01 |
| 213677_s_at | 0.0936 | 0.17 | 0.113 | 0.0967 | 0.171 | 0.0596 | 0.0382 | 0.0698 | 0.108 | 0.0926 |
| 214086_s_at | 0.0688 | 0.0903 | 0.0466 | 0.101 | 0.0671 | 0.0496 | 0.0346 | 0.0374 | 0.0611 | 0.172 |
| 214585_s_at | 0.092 | 0.231 | 0.143 | 0.245 | 0.181 | 0.0969 | 0.123 | 0.221 | 0.117 | 0.177 |
| 214672_at | 0.0786 | 0.0911 | 0.0483 | 0.0729 | 0.0532 | 0.0415 | 0.0661 | 0.0587 | 0.062 | 0.0453 |
| 214844_s_at | 0.202 | 0.149 | 0.01 | 0.01 | 0.01 | 0.01 | 0.01 | 0.01 | 0.0262 | 0.022 |
| 217797_at | 0.38 | 0.341 | 0.279 | 0.237 | 0.42 | 0.477 | 0.328 | 0.457 | 0.371 | 0.594 |
| 217895_at | 0.0877 | 0.104 | 0.152 | 0.197 | 0.191 | 0.12 | 0.053 | 0.112 | 0.131 | 0.111 |
| 218625_at | 0.121 | 0.0945 | 0.01 | 0.0904 | 0.01 | 0.01 | 0.01 | 0.01 | 0.01 | 0.01 |

TABLE 1-continued

| | | | | | | | | | | |
|---|---|---|---|---|---|---|---|---|---|---|
| 218768_at | 0.169 | 0.349 | 0.18 | 0.297 | 0.214 | 0.249 | 0.138 | 0.181 | 0.201 | 0.187 |
| 218818_at | 0.0204 | 0.01 | 0.0218 | 0.01 | 0.0207 | 0.01 | 0.01 | 0.021 | 0.01 | 0.01 |
| 218998_at | 0.0464 | 0.129 | 0.0973 | 0.0974 | 0.13 | 0.12 | 0.0936 | 0.0976 | 0.0737 | 0.115 |
| 219595_at | 0.0248 | 0.13 | 0.0417 | 0.0624 | 0.0387 | 0.0361 | 0.0292 | 0.0381 | 0.0299 | 0.0412 |
| 219906_at | 0.0358 | 0.0295 | 0.01 | 0.0582 | 0.01 | 0.01 | 0.0453 | 0.01 | 0.0357 | 0.01 |
| 221214_s_at | 0.0311 | 0.0321 | 0.0626 | 0.0715 | 0.0524 | 0.131 | 0.0336 | 0.0774 | 0.0321 | 0.0659 |
| 221249_s_at | 0.0311 | 0.0397 | 0.0573 | 0.0876 | 0.0463 | 0.03 | 0.0208 | 0.0464 | 0.0204 | 0.052 |
| 222587_s_at | 0.0269 | 0.0587 | 0.107 | 0.1 | 0.125 | 0.038 | 0.0679 | 0.171 | 0.0964 | 0.116 |
| 222612_at | 0.0665 | 0.0543 | 0.0248 | 0.0626 | 0.0284 | 0.01 | 0.041 | 0.0314 | 0.0716 | 0.0343 |
| 222775_s_at | 0.146 | 0.0925 | 0.0692 | 0.185 | 0.0603 | 0.116 | 0.103 | 0.0604 | 0.164 | 0.0764 |
| 222807_at | 0.0616 | 0.0822 | 0.0245 | 0.0496 | 0.0358 | 0.01 | 0.0314 | 0.033 | 0.0482 | 0.0396 |
| 222906_at | 0.178 | 0.129 | 0.0505 | 0.117 | 0.0891 | 0.1 | 0.0865 | 0.0572 | 0.343 | 0.0547 |
| 223175_s_at | 0.0856 | 0.0866 | 0.05 | 0.0637 | 0.0469 | 0.0814 | 0.0474 | 0.0446 | 0.0533 | 0.0682 |
| 223197_s_at | 0.188 | 0.22 | 0.0553 | 0.11 | 0.0878 | 0.103 | 0.115 | 0.0591 | 0.163 | 0.0748 |
| 223206_s_at | 0.168 | 0.156 | 0.0562 | 0.0921 | 0.103 | 0.109 | 0.122 | 0.108 | 0.128 | 0.0757 |
| 223448_x_at | 0.447 | 0.185 | 0.0814 | 0.197 | 0.0749 | 0.308 | 0.176 | 0.0615 | 0.33 | 0.0915 |
| 223470_at | 0.206 | 0.113 | 0.0653 | 0.0992 | 0.0876 | 0.0993 | 0.0474 | 0.128 | 0.143 | 0.108 |
| 223518_at | 0.0998 | 0.113 | 0.0372 | 0.113 | 0.0284 | 0.0803 | 0.0455 | 0.0278 | 0.0628 | 0.0247 |
| 223528_s_at | 0.29 | 0.358 | 0.0481 | 0.22 | 0.0266 | 0.133 | 0.22 | 0.0454 | 0.0621 | 0.0745 |
| 223570_at | 0.0722 | 0.0778 | 0.01 | 0.0212 | 0.0375 | 0.0814 | 0.01 | 0.01 | 0.0285 | 0.0613 |
| 224473_x_at | 0.126 | 0.11 | 0.037 | 0.0519 | 0.0587 | 0.0888 | 0.082 | 0.042 | 0.0694 | 0.0434 |
| 224721_at | 0.0835 | 0.181 | 0.104 | 0.13 | 0.144 | 0.0676 | 0.0769 | 0.0837 | 0.121 | 0.103 |
| 225025_at | 0.199 | 0.0939 | 0.0289 | 0.0437 | 0.0268 | 0.0655 | 0.0948 | 0.0461 | 0.0606 | 0.0512 |
| 225097_at | 0.075 | 0.506 | 0.0851 | 0.15 | 0.01 | 0.01 | 0.0512 | 0.01 | 0.17 | 0.0776 |
| 225506_at | 0.201 | 0.114 | 0.0457 | 0.146 | 0.0392 | 0.146 | 0.0673 | 0.0426 | 0.117 | 0.0228 |
| 225554_s_at | 0.289 | 0.339 | 0.112 | 0.313 | 0.109 | 0.448 | 0.209 | 0.0623 | 0.239 | 0.164 |
| 225584_at | 0.041 | 0.0572 | 0.0471 | 0.0531 | 0.0577 | 0.0201 | 0.0461 | 0.044 | 0.046 | 0.034 |
| 225841_at | 0.417 | 0.0382 | 0.0787 | 0.0744 | 0.13 | 0.0951 | 0.111 | 0.0803 | 0.127 | 0.0226 |
| 225947_at | 0.346 | 0.339 | 0.0669 | 0.351 | 0.108 | 0.348 | 0.214 | 0.0714 | 0.379 | 0.151 |
| 226124_at | 0.206 | 0.208 | 0.0385 | 0.117 | 0.0358 | 0.0613 | 0.0929 | 0.0274 | 0.113 | 0.0497 |
| 226139_at | 0.0792 | 0.0294 | 0.01 | 0.0425 | 0.01 | 0.0497 | 0.0493 | 0.01 | 0.0248 | 0.0249 |
| 226308_at | 0.0396 | 0.0205 | 0.01 | 0.0201 | 0.01 | 0.0317 | 0.01 | 0.01 | 0.01 | 0.0206 |
| 226428_at | 0.228 | 0.116 | 0.0543 | 0.102 | 0.0392 | 0.185 | 0.0813 | 0.0436 | 0.0921 | 0.0272 |
| 226616_s_at | 0.304 | 0.324 | 0.164 | 0.269 | 0.0942 | 0.224 | 0.154 | 0.114 | 0.346 | 0.192 |
| 226651_at | 0.075 | 0.112 | 0.0223 | 0.0685 | 0.0618 | 0.0581 | 0.01 | 0.0204 | 0.0818 | 0.03 |
| 226693_at | 0.16 | 0.364 | 0.0476 | 0.111 | 0.0384 | 0.0793 | 0.0788 | 0.0837 | 0.11 | 0.0752 |
| 226749_at | 0.195 | 0.17 | 0.0976 | 0.263 | 0.137 | 0.17 | 0.0941 | 0.0783 | 0.181 | 0.0885 |
| 226810_at | 0.606 | 0.451 | 0.0218 | 0.0531 | 0.0407 | 0.038 | 0.025 | 0.01 | 0.01 | 0.143 |
| 226839_at | 0.201 | 0.131 | 0.0535 | 0.0602 | 0.0555 | 0.114 | 0.0781 | 0.054 | 0.095 | 0.0543 |
| 226917_s_at | 0.217 | 0.49 | 0.0674 | 0.349 | 0.123 | 0.144 | 0.123 | 0.101 | 0.373 | 0.138 |
| 227181_at | 0.0545 | 0.355 | 0.01 | 0.059 | 0.01 | 0.0877 | 0.0423 | 0.01 | 0.107 | 0.0281 |
| 227412_at | 0.0934 | 0.0881 | 0.0231 | 0.0602 | 0.01 | 0.0465 | 0.111 | 0.022 | 0.104 | 0.021 |
| 227427_at | 0.0764 | 0.0763 | 0.01 | 0.01 | 0.01 | 0.0275 | 0.01 | 0.01 | 0.01 | 0.01 |
| 227472_at | 0.0333 | 0.0338 | 0.01 | 0.0295 | 0.01 | 0.0222 | 0.01 | 0.01 | 0.0227 | 0.01 |
| 227603_at | 0.155 | 0.216 | 0.0252 | 0.117 | 0.0282 | 0.111 | 0.0897 | 0.0486 | 0.0782 | 0.0436 |
| 227810_at | 0.103 | 0.0528 | 0.0732 | 0.166 | 0.0777 | 0.074 | 0.113 | 0.0838 | 0.17 | 0.143 |
| 227921_at | 0.299 | 0.414 | 0.0267 | 0.184 | 0.188 | 0.159 | 0.103 | 0.0515 | 0.207 | 0.111 |
| 228286_at | 0.0842 | 0.0998 | 0.0385 | 0.0767 | 0.0617 | 0.0232 | 0.0224 | 0.0392 | 0.138 | 0.0577 |
| 228650_at | 0.0651 | 0.134 | 0.0824 | 0.0767 | 0.05 | 0.074 | 0.0269 | 0.0401 | 0.18 | 0.0793 |
| 228736_at | 0.0297 | 0.0543 | 0.01 | 0.0224 | 0.01 | 0.01 | 0.0282 | 0.01 | 0.0263 | 0.0216 |
| 228930_at | 0.117 | 0.122 | 0.0303 | 0.0779 | 0.0298 | 0.0655 | 0.0865 | 0.0212 | 0.129 | 0.069 |
| 229001_at | 0.111 | 0.0954 | 0.01 | 0.0755 | 0.01 | 0.01 | 0.113 | 0.0359 | 0.057 | 0.01 |
| 229035_s_at | 0.0807 | 0.135 | 0.01 | 0.116 | 0.037 | 0.0919 | 0.073 | 0.0335 | 0.172 | 0.0539 |

TABLE 1-continued

| | | | | | | | | | | |
|---|---|---|---|---|---|---|---|---|---|---|
| 229384_at | 0.087 | 0.156 | 0.0219 | 0.116 | 0.0293 | 0.0676 | 0.101 | 0.0409 | 0.11 | 0.0229 |
| 229421_s_at | 0.01 | 0.01 | 0.01 | 0.0331 | 0.01 | 0.0285 | 0.01 | 0.01 | 0.0212 | 0.01 |
| 229534_at | 0.0736 | 0.0455 | 0.026 | 0.0295 | 0.0222 | 0.0338 | 0.01 | 0.01 | 0.0278 | 0.0396 |
| 229570_at | 0.0439 | 0.0426 | 0.01 | 0.01 | 0.01 | 0.0243 | 0.01 | 0.01 | 0.0431 | 0.01 |
| 230048_at | 0.01 | 0.01 | 0.0212 | 0.0236 | 0.01 | 0.0275 | 0.0423 | 0.0322 | 0.0263 | 0.0211 |
| 230791_at | 0.313 | 0.294 | 0.01 | 0.0862 | 0.0245 | 0.0486 | 0.124 | 0.0428 | 0.0716 | 0.0743 |
| 230922_x_at | 0.01 | 0.0866 | 0.0208 | 0.0519 | 0.034 | 0.0476 | 0.01 | 0.0241 | 0.0351 | 0.0309 |
| 230983_at | 0.0219 | 0.0249 | 0.01 | 0.01 | 0.01 | 0.0444 | 0.01 | 0.01 | 0.0409 | 0.01 |
| 231271_x_at | 0.158 | 0.415 | 0.0486 | 0.264 | 0.0925 | 0.0856 | 0.125 | 0.0874 | 0.184 | 0.0659 |
| 232524_x_at | 0.232 | 0.217 | 0.059 | 0.184 | 0.12 | 0.0909 | 0.101 | 0.0974 | 0.226 | 0.126 |
| 232527_at | 0.142 | 0.0895 | 0.0253 | 0.0685 | 0.01 | 0.0317 | 0.0762 | 0.0224 | 0.111 | 0.0239 |
| 233214_at | 0.0877 | 0.123 | 0.0493 | 0.0992 | 0.0597 | 0.0623 | 0.0813 | 0.0338 | 0.0921 | 0.0429 |
| 233302_at | 0.0899 | 0.0352 | 0.01 | 0.0909 | 0.01 | 0.0402 | 0.01 | 0.0208 | 0.103 | 0.01 |
| 233429_at | 0.0241 | 0.069 | 0.01 | 0.0271 | 0.01 | 0.01 | 0.0205 | 0.01 | 0.0256 | 0.01 |
| 233440_at | 0.01 | 0.0661 | 0.01 | 0.0543 | 0.01 | 0.0243 | 0.01 | 0.01 | 0.01 | 0.0238 |
| 233493_at | 0.01 | 0.0396 | 0.01 | 0.01 | 0.01 | 0.01 | 0.0211 | 0.01 | 0.01 | 0.01 |
| 233599_at | 0.01 | 0.01 | 0.01 | 0.01 | 0.01 | 0.01 | 0.01 | 0.01 | 0.01 | 0.01 |
| 234735_s_at | 0.171 | 0.0939 | 0.01 | 0.01 | 0.037 | 0.0782 | 0.089 | 0.0486 | 0.0979 | 0.0394 |
| 235363_at | 0.0828 | 0.0675 | 0.0249 | 0.0449 | 0.0374 | 0.056 | 0.01 | 0.0311 | 0.076 | 0.0349 |
| 235467_s_at | 0.0538 | 0.0294 | 0.01 | 0.0224 | 0.01 | 0.0243 | 0.01 | 0.01 | 0.01 | 0.01 |
| 235634_at | 0.0311 | 0.091 | 0.01 | 0.0248 | 0.01 | 0.0232 | 0.0256 | 0.01 | 0.0256 | 0.01 |
| 236312_at | 0.0453 | 0.0382 | 0.0202 | 0.0449 | 0.0428 | 0.01 | 0.0288 | 0.0366 | 0.0913 | 0.01 |
| 236875_at | 0.0233 | 0.01 | 0.01 | 0.01 | 0.01 | 0.01 | 0.01 | 0.01 | 0.01 | 0.01 |
| 237023_at | 0.0403 | 0.0499 | 0.0242 | 0.0389 | 0.0233 | 0.038 | 0.0333 | 0.01 | 0.0365 | 0.01 |
| 239496_at | 0.0318 | 0.0499 | 0.01 | 0.0283 | 0.01 | 0.0285 | 0.01 | 0.01 | 0.0212 | 0.01 |
| 240130_at | 0.01 | 0.0235 | 0.01 | 0.01 | 0.01 | 0.0275 | 0.01 | 0.01 | 0.01 | 0.01 |
| 241395_at | 0.0283 | 0.01 | 0.01 | 0.0283 | 0.01 | 0.01 | 0.0365 | 0.01 | 0.0818 | 0.01 |
| 242171_at | 0.0389 | 0.0338 | 0.01 | 0.0212 | 0.01 | 0.01 | 0.0224 | 0.01 | 0.01 | 0.01 |
| 242602_x_at | 0.0736 | 0.0793 | 0.0312 | 0.0496 | 0.0344 | 0.0528 | 0.05 | 0.0344 | 0.038 | 0.0231 |
| 242606_at | 0.01 | 0.01 | 0.01 | 0.0331 | 0.01 | 0.0232 | 0.01 | 0.01 | 0.0658 | 0.01 |
| 243003_at | 0.0927 | 0.144 | 0.01 | 0.0968 | 0.024 | 0.0539 | 0.0224 | 0.01 | 0.0891 | 0.0286 |
| 243185_at | 0.01 | 0.0352 | 0.01 | 0.0354 | 0.01 | 0.01 | 0.0218 | 0.01 | 0.01 | 0.01 |
| 31826_at | 0.0566 | 0.106 | 0.0658 | 0.0757 | 0.0545 | 0.0892 | 0.0651 | 0.0817 | 0.071 | 0.0535 |
| 35150_at | 0.0204 | 0.107 | 0.045 | 0.0519 | 0.0379 | 0.0503 | 0.0648 | 0.0526 | 0.0416 | 0.0305 |
| 64474_g_at | 0.0594 | 0.0414 | 0.0618 | 0.0449 | 0.0423 | 0.0427 | 0.0245 | 0.0269 | 0.0393 | 0.0399 |
| 91617_at | 0.0448 | 0.065 | 0.0399 | 0.0357 | 0.0306 | 0.0354 | 0.0201 | 0.0274 | 0.0561 | 0.0511 |

| Systematic Name | LXFA_289, Avastin_p P normalized | LXFA_526, Avastin_p P normalized | LXFA_586, Avastin_p P normalized | LXFA_629, Avastin_p P normalized | LXFA_644, Avastin_p P normalized | LXFA_737, Avastin_p P normalized | LXFA_PC14, Avastin_p P normalized | LXFE_211, Avastin_p P normalized | LXFL_529, Avastin_p P normalized | MAXF_1162, Avastin_p P normalized |
|---|---|---|---|---|---|---|---|---|---|---|
| 200076_s_at | 0.219 | 0.294 | 0.149 | 0.142 | 0.0549 | 0.0548 | 0.137 | 0.125 | 0.15 | 0.0923 |
| 200631_s_at | 0.637 | 0.791 | 0.42 | 0.456 | 0.414 | 0.62 | 0.843 | 1.317 | 0.56 | 0.626 |
| 201722_s_at | 0.161 | 0.102 | 0.153 | 0.152 | 0.48 | 0.171 | 0.233 | 0.146 | 0.114 | 0.134 |
| 201919_at | 0.189 | 0.152 | 0.19 | 0.204 | 0.114 | 0.243 | 0.187 | 0.143 | 0.222 | 0.254 |
| 202333_s_at | 0.197 | 0.11 | 0.2 | 0.0559 | 0.297 | 0.135 | 0.314 | 0.135 | 0.131 | 0.0825 |
| 202758_s_at | 0.0568 | 0.0607 | 0.01 | 0.01 | 0.0653 | 0.01 | 0.11 | 0.0696 | 0.0401 | 0.01 |
| 203092_at | 0.0277 | 0.0228 | 0.01 | 0.01 | 0.0228 | 0.01 | 0.043 | 0.04 | 0.0419 | 0.0228 |
| 203846_at | 0.0502 | 0.0654 | 0.0639 | 0.0928 | 0.0594 | 0.0523 | 0.103 | 0.145 | 0.0577 | 0.0393 |
| 205042_at | 0.296 | 0.12 | 0.0433 | 0.105 | 0.0992 | 0.322 | 0.0489 | 0.0253 | 0.123 | 0.0487 |
| 205046_at | 0.04 | 0.0501 | 0.0274 | 0.0223 | 0.061 | 0.0522 | 0.0492 | 0.0662 | 0.0387 | 0.0361 |
| 205105_at | 0.135 | 0.0392 | 0.0422 | 0.0304 | 0.059 | 0.0532 | 0.0622 | 0.151 | 0.0525 | 0.022 |
| 205481_at | 0.0226 | 0.01 | 0.01 | 0.01 | 0.01 | 0.01 | 0.01 | 0.01 | 0.0273 | 0.022 |

TABLE 1-continued

| | | | | | | | | | | |
|---|---|---|---|---|---|---|---|---|---|---|
| 206003_at | 0.01 | 0.0317 | 0.0239 | 0.0284 | 0.0364 | 0.0722 | 0.0225 | 0.01 | 0.01 | 0.01 |
| 208369_s_at | 0.024 | 0.0296 | 0.01 | 0.01 | 0.0274 | 0.0227 | 0.0313 | 0.0339 | 0.01 | 0.0236 |
| 208848_at | 0.0408 | 0.0971 | 0.0901 | 0.0365 | 0.0391 | 0.0495 | 0.0612 | 0.208 | 0.0648 | 0.0692 |
| 208951_at | 0.0473 | 0.0324 | 0.121 | 0.0397 | 0.127 | 0.0612 | 0.0688 | 0.0818 | 0.0533 | 0.0479 |
| 209161_at | 0.116 | 0.203 | 0.103 | 0.113 | 0.0867 | 0.0939 | 0.161 | 0.25 | 0.119 | 0.0786 |
| 209758_s_at | 0.099 | 0.401 | 0.244 | 0.0276 | 0.0283 | 0.0247 | 0.239 | 0.01 | 0.01 | 0.0919 |
| 211974_x_at | 0.23 | 0.208 | 0.177 | 0.163 | 0.14 | 0.139 | 0.141 | 0.212 | 0.294 | 0.277 |
| 211976_at | 0.197 | 0.0821 | 0.0479 | 0.062 | 0.0609 | 0.0868 | 0.0858 | 0.123 | 0.101 | 0.101 |
| 212394_at | 0.01 | 0.0327 | 0.01 | 0.01 | 0.0209 | 0.01 | 0.0312 | 0.01 | 0.0273 | 0.01 |
| 213677_s_at | 0.0648 | 0.0883 | 0.0821 | 0.077 | 0.169 | 0.117 | 0.0648 | 0.0421 | 0.0818 | 0.0589 |
| 214086_s_at | 0.0546 | 0.0382 | 0.0525 | 0.0491 | 0.0638 | 0.09 | 0.0453 | 0.0754 | 0.046 | 0.033 |
| 214585_s_at | 0.182 | 0.148 | 0.132 | 0.206 | 0.208 | 0.18 | 0.165 | 0.172 | 0.117 | 0.166 |
| 214672_at | 0.0495 | 0.0429 | 0.0331 | 0.0572 | 0.0511 | 0.0534 | 0.0663 | 0.108 | 0.0448 | 0.0542 |
| 214844_s_at | 0.01 | 0.01 | 0.01 | 0.01 | 0.01 | 0.0301 | 0.01 | 0.01 | 0.0217 | 0.0228 |
| 217797_at | 0.791 | 0.214 | 0.375 | 0.225 | 0.915 | 0.429 | 0.282 | 0.331 | 0.299 | 0.31 |
| 217895_at | 0.0801 | 0.0692 | 0.0525 | 0.102 | 0.0645 | 0.0829 | 0.104 | 0.117 | 0.118 | 0.105 |
| 218625_at | 0.01 | 0.01 | 0.0433 | 0.01 | 0.01 | 0.01 | 0.01 | 0.237 | 0.01 | 0.01 |
| 218768_at | 0.245 | 0.18 | 0.173 | 0.238 | 0.175 | 0.165 | 0.214 | 0.222 | 0.213 | 0.123 |
| 218818_at | 0.01 | 0.01 | 0.0228 | 0.0247 | 0.0238 | 0.0291 | 0.0325 | 0.0311 | 0.01 | 0.0251 |
| 218998_at | 0.124 | 0.128 | 0.115 | 0.11 | 0.0416 | 0.0487 | 0.124 | 0.0983 | 0.0894 | 0.0432 |
| 219595_at | 0.0408 | 0.0314 | 0.0388 | 0.0357 | 0.02 | 0.0457 | 0.0634 | 0.0522 | 0.0407 | 0.0369 |
| 219906_at | 0.0335 | 0.01 | 0.0308 | 0.0247 | 0.01 | 0.01 | 0.01 | 0.0363 | 0.046 | 0.0283 |
| 221214_s_at | 0.0524 | 0.0702 | 0.01 | 0.0361 | 0.0287 | 0.0562 | 0.118 | 0.0644 | 0.022 | 0.0566 |
| 221249_s_at | 0.0255 | 0.0286 | 0.0365 | 0.01 | 0.0217 | 0.0435 | 0.021 | 0.0577 | 0.0542 | 0.01 |
| 222587_s_at | 0.152 | 0.116 | 0.0658 | 0.132 | 0.132 | 0.069 | 0.103 | 0.0412 | 0.0398 | 0.0373 |
| 222612_at | 0.0506 | 0.0359 | 0.0279 | 0.0476 | 0.0312 | 0.0317 | 0.0246 | 0.0443 | 0.0628 | 0.0607 |
| 222775_s_at | 0.106 | 0.0837 | 0.0918 | 0.0717 | 0.0513 | 0.0773 | 0.0399 | 0.0734 | 0.0852 | 0.0835 |
| 222807_at | 0.0594 | 0.0341 | 0.0499 | 0.0456 | 0.0286 | 0.0337 | 0.0419 | 0.0398 | 0.0359 | 0.0451 |
| 222906_at | 1.034 | 0.0527 | 0.271 | 0.0938 | 0.114 | 0.0301 | 0.0346 | 0.127 | 0.225 | 0.139 |
| 223175_s_at | 0.091 | 0.0607 | 0.0479 | 0.0664 | 0.0407 | 0.0547 | 0.0359 | 0.0519 | 0.0449 | 0.102 |
| 223197_s_at | 0.125 | 0.169 | 0.154 | 0.126 | 0.0618 | 0.0621 | 0.056 | 0.148 | 0.149 | 0.117 |
| 223206_s_at | 0.143 | 0.109 | 0.01 | 0.133 | 0.0472 | 0.0894 | 0.117 | 0.144 | 0.1 | 0.148 |
| 223448_x_at | 0.091 | 0.144 | 0.13 | 0.158 | 0.0614 | 0.0561 | 0.0906 | 0.159 | 0.169 | 0.216 |
| 223470_at | 0.107 | 0.0611 | 0.0938 | 0.0871 | 0.139 | 0.111 | 0.0616 | 0.373 | 0.0516 | 0.118 |
| 223518_at | 0.0695 | 0.109 | 0.0698 | 0.0757 | 0.0433 | 0.0357 | 0.0206 | 0.0774 | 0.11 | 0.0487 |
| 223528_s_at | 0.0809 | 0.0616 | 0.0639 | 0.149 | 0.0544 | 0.121 | 0.0476 | 0.0465 | 0.104 | 0.154 |
| 223570_at | 0.0544 | 0.0235 | 0.0359 | 0.0369 | 0.01 | 0.0459 | 0.0368 | 0.0528 | 0.0348 | 0.0607 |
| 224473_x_at | 0.0948 | 0.0372 | 0.0958 | 0.0905 | 0.043 | 0.0598 | 0.0444 | 0.0769 | 0.11 | 0.154 |
| 224721_at | 0.14 | 0.147 | 0.0738 | 0.145 | 0.0724 | 0.101 | 0.045 | 0.0479 | 0.0937 | 0.0613 |
| 225025_at | 0.147 | 0.0616 | 0.13 | 0.114 | 0.0227 | 0.0538 | 0.0412 | 0.119 | 0.0684 | 0.103 |
| 225097_at | 0.0278 | 0.0492 | 0.0279 | 0.053 | 0.0663 | 0.0537 | 0.0338 | 0.505 | 0.0432 | 0.118 |
| 225506_at | 0.115 | 0.0829 | 0.0798 | 0.0858 | 0.078 | 0.0486 | 0.0271 | 0.0783 | 0.078 | 0.113 |
| 225554_s_at | 0.311 | 0.193 | 0.164 | 0.417 | 0.107 | 0.165 | 0.0862 | 0.301 | 0.14 | 0.32 |
| 225584_at | 0.0518 | 0.102 | 0.0539 | 0.0349 | 0.0386 | 0.0489 | 0.0643 | 0.0599 | 0.0667 | 0.0361 |
| 225841_at | 0.166 | 0.114 | 0.158 | 0.205 | 0.139 | 0.128 | 0.0755 | 0.189 | 0.153 | 0.159 |
| 225947_at | 0.513 | 0.535 | 0.467 | 0.469 | 0.119 | 0.101 | 0.103 | 0.167 | 0.237 | 0.238 |
| 226124_at | 0.105 | 0.0665 | 0.0738 | 0.065 | 0.0574 | 0.0338 | 0.0335 | 0.127 | 0.142 | 0.104 |
| 226139_at | 0.163 | 0.0275 | 0.0698 | 0.059 | 0.0285 | 0.0215 | 0.01 | 0.0438 | 0.0426 | 0.0715 |
| 226308_at | 0.0266 | 0.0235 | 0.01 | 0.01 | 0.01 | 0.01 | 0.0226 | 0.0389 | 0.01 | 0.0258 |
| 226428_at | 0.119 | 0.157 | 0.0718 | 0.0818 | 0.0471 | 0.0505 | 0.038 | 0.0769 | 0.0555 | 0.0811 |
| 226616_s_at | 0.269 | 0.343 | 0.637 | 0.0938 | 0.137 | 0.188 | 0.0991 | 0.489 | 0.313 | 0.298 |
| 226651_at | 0.0594 | 0.0425 | 0.0658 | 0.107 | 0.0718 | 0.0297 | 0.0392 | 0.181 | 0.165 | 0.3 |
| 226693_at | 0.143 | 0.0341 | 0.0838 | 0.0938 | 0.0636 | 0.0494 | 0.045 | 0.0792 | 0.0802 | 0.0805 |

TABLE 1-continued

| | | | | | | | | | | |
|---|---|---|---|---|---|---|---|---|---|---|
| 226749_at | 0.161 | 0.149 | 0.152 | 0.153 | 0.0633 | 0.15 | 0.0607 | 0.201 | 0.174 | 0.147 |
| 226810_at | 0.0455 | 0.167 | 0.0439 | 0.0241 | 0.0221 | 0.0688 | 0.112 | 0.0573 | 0.0538 | 0.157 |
| 226839_at | 0.148 | 0.126 | 0.0639 | 0.0617 | 0.0275 | 0.0564 | 0.0584 | 0.0935 | 0.0634 | 0.0974 |
| 226917_s_at | 0.269 | 0.149 | 0.251 | 0.202 | 0.126 | 0.135 | 0.126 | 0.161 | 0.234 | 0.231 |
| 227181_at | 0.0468 | 0.051 | 0.0339 | 0.0543 | 0.0283 | 0.028 | 0.0211 | 0.148 | 0.156 | 0.132 |
| 227412_at | 0.01 | 0.0275 | 0.02 | 0.0302 | 0.01 | 0.01 | 0.01 | 0.0255 | 0.0303 | 0.0445 |
| 227427_at | 0.0228 | 0.01 | 0.0319 | 0.0308 | 0.01 | 0.01 | 0.01 | 0.01 | 0.0252 | 0.0715 |
| 227472_at | 0.0291 | 0.0266 | 0.01 | 0.0201 | 0.01 | 0.01 | 0.01 | 0.01 | 0.01 | 0.01 |
| 227603_at | 0.142 | 0.0301 | 0.104 | 0.225 | 0.01 | 0.11 | 0.049 | 0.123 | 0.123 | 0.354 |
| 227810_at | 0.109 | 0.0244 | 0.0798 | 0.0851 | 0.0748 | 0.0647 | 0.0975 | 0.0769 | 0.14 | 0.0727 |
| 227921_at | 0.139 | 0.134 | 0.257 | 0.114 | 0.0305 | 0.163 | 0.0244 | 0.211 | 0.0308 | 0.189 |
| 228286_at | 0.0695 | 0.0478 | 0.0479 | 0.0677 | 0.0451 | 0.0417 | 0.0314 | 0.0501 | 0.0297 | 0.0505 |
| 228650_at | 0.0923 | 0.0554 | 0.156 | 0.0308 | 0.0549 | 0.0485 | 0.0644 | 0.177 | 0.172 | 0.0631 |
| 228736_at | 0.01 | 0.0213 | 0.01 | 0.01 | 0.01 | 0.01 | 0.01 | 0.0206 | 0.023 | 0.01 |
| 228930_at | 0.086 | 0.093 | 0.0599 | 0.0818 | 0.0235 | 0.0409 | 0.0359 | 0.0778 | 0.136 | 0.0986 |
| 229001_at | 0.0303 | 0.0399 | 0.01 | 0.0282 | 0.01 | 0.01 | 0.01 | 0.0304 | 0.01 | 0.0385 |
| 229035_s_at | 0.107 | 0.0961 | 0.0479 | 0.103 | 0.01 | 0.0727 | 0.0292 | 0.0573 | 0.129 | 0.0823 |
| 229384_at | 0.163 | 0.0744 | 0.0539 | 0.065 | 0.01 | 0.0224 | 0.0286 | 0.0617 | 0.0852 | 0.0571 |
| 229421_s_at | 0.0341 | 0.01 | 0.0519 | 0.01 | 0.01 | 0.01 | 0.01 | 0.01 | 0.01 | 0.01 |
| 229534_at | 0.0936 | 0.0319 | 0.0798 | 0.109 | 0.0252 | 0.193 | 0.0314 | 0.0273 | 0.01 | 0.0355 |
| 229570_at | 0.0443 | 0.01 | 0.01 | 0.01 | 0.01 | 0.01 | 0.01 | 0.01 | 0.0224 | 0.0337 |
| 230048_at | 0.01 | 0.218 | 0.01 | 0.01 | 0.01 | 0.01 | 0.0322 | 0.01 | 0.0505 | 0.01 |
| 230791_at | 0.0632 | 0.0811 | 0.01 | 0.0489 | 0.0987 | 0.0331 | 0.01 | 0.0322 | 0.105 | 0.242 |
| 230922_x_at | 0.0266 | 0.0687 | 0.0399 | 0.0221 | 0.0247 | 0.0295 | 0.0265 | 0.025 | 0.01 | 0.01 |
| 230983_at | 0.0594 | 0.01 | 0.0339 | 0.0228 | 0.01 | 0.01 | 0.01 | 0.0268 | 0.0325 | 0.021 |
| 231271_x_at | 0.234 | 0.212 | 0.01 | 0.134 | 0.0714 | 0.109 | 0.0798 | 0.244 | 0.164 | 0.239 |
| 232524_x_at | 0.13 | 0.0771 | 0.263 | 0.174 | 0.11 | 0.14 | 0.115 | 0.128 | 0.138 | 0.226 |
| 232527_at | 0.0455 | 0.0669 | 0.0339 | 0.0429 | 0.0236 | 0.0507 | 0.01 | 0.089 | 0.0937 | 0.0487 |
| 233214_at | 0.191 | 0.0846 | 0.11 | 0.0858 | 0.0318 | 0.0911 | 0.0204 | 0.0756 | 0.0651 | 0.0673 |
| 233302_at | 0.0202 | 0.01 | 0.01 | 0.01 | 0.01 | 0.01 | 0.01 | 0.01 | 0.01 | 0.01 |
| 233429_at | 0.0303 | 0.01 | 0.01 | 0.01 | 0.01 | 0.01 | 0.01 | 0.01 | 0.01 | 0.0337 |
| 233440_at | 0.0556 | 0.01 | 0.0259 | 0.0308 | 0.01 | 0.01 | 0.01 | 0.01 | 0.0247 | 0.01 |
| 233493_at | 0.01 | 0.0253 | 0.01 | 0.01 | 0.01 | 0.01 | 0.01 | 0.01 | 0.01 | 0.01 |
| 233599_at | 0.01 | 0.01 | 0.01 | 0.0248 | 0.01 | 0.01 | 0.01 | 0.0716 | 0.01 | 0.01 |
| 234735_s_at | 0.11 | 0.0408 | 0.0559 | 0.0697 | 0.0652 | 0.036 | 0.0348 | 0.0742 | 0.0566 | 0.163 |
| 235363_at | 0.01 | 0.0594 | 0.0599 | 0.0268 | 0.0386 | 0.01 | 0.0451 | 0.0819 | 0.01 | 0.0282 |
| 235467_s_at | 0.01 | 0.0332 | 0.0279 | 0.0288 | 0.01 | 0.01 | 0.01 | 0.0268 | 0.01 | 0.01 |
| 235634_at | 0.0544 | 0.0275 | 0.0259 | 0.0248 | 0.01 | 0.0209 | 0.01 | 0.0389 | 0.0561 | 0.0294 |
| 236312_at | 0.01 | 0.01 | 0.0219 | 0.01 | 0.01 | 0.0228 | 0.01 | 0.0859 | 0.0365 | 0.01 |
| 236875_at | 0.0354 | 0.01 | 0.01 | 0.01 | 0.01 | 0.01 | 0.01 | 0.01 | 0.01 | 0.01 |
| 237023_at | 0.01 | 0.0292 | 0.0299 | 0.0402 | 0.01 | 0.0233 | 0.01 | 0.0268 | 0.01 | 0.0331 |
| 239496_at | 0.01 | 0.01 | 0.02 | 0.01 | 0.01 | 0.0209 | 0.01 | 0.0206 | 0.0247 | 0.0481 |
| 240130_at | 0.01 | 0.01 | 0.01 | 0.01 | 0.01 | 0.01 | 0.01 | 0.0201 | 0.01 | 0.01 |
| 241395_at | 0.0367 | 0.0337 | 0.0319 | 0.01 | 0.01 | 0.01 | 0.01 | 0.01 | 0.0286 | 0.0258 |
| 242171_at | 0.024 | 0.0222 | 0.01 | 0.0201 | 0.01 | 0.0207 | 0.01 | 0.0291 | 0.01 | 0.0288 |
| 242602_x_at | 0.0316 | 0.0372 | 0.0539 | 0.065 | 0.0272 | 0.0292 | 0.0289 | 0.0376 | 0.0381 | 0.0469 |
| 242606_at | 0.01 | 0.0368 | 0.01 | 0.01 | 0.01 | 0.01 | 0.01 | 0.0201 | 0.0337 | 0.0228 |
| 243003_at | 0.0885 | 0.01 | 0.0639 | 0.0637 | 0.01 | 0.0302 | 0.01 | 0.105 | 0.188 | 0.1 |
| 243185_at | 0.0518 | 0.01 | 0.01 | 0.0268 | 0.01 | 0.01 | 0.01 | 0.01 | 0.01 | 0.01 |
| 31826_at | 0.121 | 0.14 | 0.108 | 0.106 | 0.0565 | 0.0693 | 0.123 | 0.107 | 0.0993 | 0.0833 |
| 35150_at | 0.0844 | 0.0385 | 0.0433 | 0.0397 | 0.0532 | 0.0467 | 0.0746 | 0.0561 | 0.0782 | 0.0644 |

TABLE 1-continued

| | | | | | | | | | | |
|---|---|---|---|---|---|---|---|---|---|---|
| 64474_g_at | 0.0429 | 0.0494 | 0.0285 | 0.0353 | 0.0492 | 0.0789 | 0.0593 | 0.0256 | 0.0475 | 0.01 |
| 91617_at | 0.0604 | 0.0211 | 0.01 | 0.0377 | 0.0472 | 0.0771 | 0.0352 | 0.0333 | 0.034 | 0.0464 |

| Systematic Name | MAXF_449, Avastin_p P normalized | MAXF_MCF7, Avastin_p P normalized | RXF_1220, Avastin_p P normalized | RXF_631, Avastin_p P normalized | RXF_944LX, Avastin_p P normalized | CXF_1103, Avastin_p R normalized | CXF_158, Avastin_p R normalized | CXF_1729, Avastin_p R normalized | LXFA_592, Avastin_p R normalized | LXFA_677, Avastin_p R normalized |
|---|---|---|---|---|---|---|---|---|---|---|
| 200076_s_at | 0.199 | 0.142 | 0.211 | 0.223 | 0.18 | 0.175 | 0.152 | 0.146 | 0.151 | 0.128 |
| 200631_s_at | 0.665 | 0.514 | 0.698 | 0.332 | 1.057 | 0.846 | 0.894 | 0.931 | 1.04 | 0.862 |
| 201722_s_at | 0.133 | 0.0458 | 0.141 | 0.0912 | 0.0974 | 0.214 | 0.103 | 0.132 | 0.0719 | 0.0631 |
| 201919_at | 0.281 | 0.176 | 0.239 | 0.322 | 0.461 | 0.283 | 0.333 | 0.305 | 0.448 | 0.296 |
| 202333_s_at | 0.078 | 0.141 | 0.131 | 0.243 | 0.149 | 0.0606 | 0.0889 | 0.12 | 0.114 | 0.133 |
| 202758_s_at | 0.066 | 0.053 | 0.0602 | 0.0586 | 0.0617 | 0.083 | 0.0718 | 0.0506 | 0.0602 | 0.0212 |
| 203092_at | 0.0522 | 0.023 | 0.055 | 0.0259 | 0.0335 | 0.0925 | 0.0351 | 0.0577 | 0.0886 | 0.01 |
| 203846_at | 0.01 | 0.0495 | 0.0499 | 0.01 | 0.0736 | 0.0585 | 0.0658 | 0.0806 | 0.0736 | 0.0763 |
| 205042_at | 0.145 | 0.01 | 0.122 | 0.0867 | 0.0822 | 0.0372 | 0.0239 | 0.01 | 0.0318 | 0.0252 |
| 205046_at | 0.0296 | 0.0288 | 0.0791 | 0.0417 | 0.079 | 0.067 | 0.0368 | 0.0798 | 0.0435 | 0.0482 |
| 205105_at | 0.01 | 0.0547 | 0.0653 | 0.167 | 0.0487 | 0.13 | 0.0919 | 0.0965 | 0.0619 | 0.111 |
| 205481_at | 0.0407 | 0.01 | 0.0997 | 0.0327 | 0.01 | 0.01 | 0.01 | 0.01 | 0.01 | 0.01 |
| 206003_at | 0.01 | 0.0299 | 0.01 | 0.0259 | 0.01 | 0.0383 | 0.0274 | 0.0396 | 0.0251 | 0.0321 |
| 208369_s_at | 0.0837 | 0.0368 | 0.0396 | 0.045 | 0.0303 | 0.0489 | 0.0423 | 0.0221 | 0.0619 | 0.0218 |
| 208848_at | 0.0434 | 0.0308 | 0.129 | 0.0518 | 0.0963 | 0.0702 | 0.0616 | 0.0654 | 0.0652 | 0.0832 |
| 208951_at | 0.105 | 0.122 | 0.0602 | 0.0946 | 0.0768 | 0.0745 | 0.0432 | 0.0424 | 0.01 | 0.0545 |
| 209161_at | 0.0511 | 0.107 | 0.0946 | 0.0484 | 0.142 | 0.156 | 0.106 | 0.198 | 0.159 | 0.234 |
| 209758_s_at | 0.0687 | 0.01 | 0.0224 | 0.588 | 0.0206 | 0.0223 | 0.01 | 0.01 | 0.01 | 0.01 |
| 211974_x_at | 0.176 | 0.226 | 0.342 | 0.393 | 0.253 | 0.364 | 0.275 | 0.483 | 0.406 | 0.244 |
| 211976_at | 0.123 | 0.0841 | 0.098 | 0.0777 | 0.119 | 0.117 | 0.194 | 0.198 | 0.268 | 0.132 |
| 212394_at | 0.01 | 0.01 | 0.0396 | 0.01 | 0.0303 | 0.033 | 0.0325 | 0.01 | 0.0201 | 0.01 |
| 213677_s_at | 0.1 | 0.0616 | 0.0946 | 0.08 | 0.0508 | 0.0968 | 0.103 | 0.139 | 0.151 | 0.131 |
| 214086_s_at | 0.0253 | 0.0443 | 0.0516 | 0.0349 | 0.093 | 0.0723 | 0.0504 | 0.0438 | 0.0886 | 0.0809 |
| 214585_s_at | 0.162 | 0.125 | 0.225 | 0.227 | 0.167 | 0.195 | 0.2 | 0.268 | 0.273 | 0.292 |
| 214672_at | 0.0515 | 0.0875 | 0.0413 | 0.0428 | 0.12 | 0.0936 | 0.0667 | 0.0843 | 0.0686 | 0.106 |
| 214844_s_at | 0.01 | 0.01 | 0.0344 | 0.0203 | 0.01 | 0.01 | 0.01 | 0.01 | 0.01 | 0.01 |
| 217797_at | 0.405 | 0.317 | 0.487 | 0.467 | 0.195 | 0.282 | 0.24 | 0.175 | 0.139 | 0.169 |
| 217895_at | 0.126 | 0.0504 | 0.115 | 0.0698 | 0.0595 | 0.177 | 0.162 | 0.162 | 0.166 | 0.11 |
| 218625_at | 0.01 | 0.01 | 0.01 | 0.01 | 0.13 | 0.01 | 0.0218 | 0.258 | 0.0284 | 0.01 |
| 218768_at | 0.197 | 0.214 | 0.244 | 0.17 | 0.115 | 0.307 | 0.276 | 0.237 | 0.301 | 0.18 |
| 218818_at | 0.01 | 0.01 | 0.01 | 0.0664 | 0.01 | 0.0468 | 0.0222 | 0.0263 | 0.0284 | 0.0442 |
| 218998_at | 0.0223 | 0.0478 | 0.105 | 0.0586 | 0.0963 | 0.146 | 0.151 | 0.164 | 0.174 | 0.147 |
| 219595_at | 0.0388 | 0.0423 | 0.086 | 0.0518 | 0.0487 | 0.0734 | 0.0598 | 0.0436 | 0.0937 | 0.0539 |
| 219906_at | 0.01 | 0.0363 | 0.01 | 0.01 | 0.0227 | 0.0426 | 0.0496 | 0.0407 | 0.01 | 0.0252 |
| 221214_s_at | 0.0453 | 0.0581 | 0.0567 | 0.0462 | 0.0563 | 0.149 | 0.0667 | 0.0554 | 0.0652 | 0.039 |
| 221249_s_at | 0.0534 | 0.0279 | 0.0327 | 0.0439 | 0.0249 | 0.0223 | 0.0568 | 0.0936 | 0.154 | 0.0258 |
| 222587_s_at | 0.0337 | 0.0664 | 0.234 | 0.0296 | 0.0543 | 0.0572 | 0.0581 | 0.104 | 0.118 | 0.126 |
| 222612_at | 0.0902 | 0.0658 | 0.0832 | 0.0355 | 0.0379 | 0.0286 | 0.0342 | 0.0591 | 0.0502 | 0.0222 |
| 222775_s_at | 0.0791 | 0.0622 | 0.0928 | 0.069 | 0.0666 | 0.107 | 0.0932 | 0.1 | 0.133 | 0.108 |
| 222807_at | 0.141 | 0.0514 | 0.0812 | 0.0709 | 0.0728 | 0.0338 | 0.0607 | 0.0353 | 0.0968 | 0.0611 |
| 222906_at | 0.222 | 0.0329 | 0.0948 | 0.0591 | 0.043 | 0.0416 | 0.0983 | 0.277 | 0.219 | 0.0689 |
| 223175_s_at | 0.0628 | 0.0526 | 0.104 | 0.0631 | 0.0646 | 0.101 | 0.0727 | 0.0669 | 0.0788 | 0.0678 |
| 223197_s_at | 0.106 | 0.0454 | 0.149 | 0.134 | 0.137 | 0.0884 | 0.121 | 0.249 | 0.168 | 0.202 |
| 223206_s_at | 0.208 | 0.239 | 0.18 | 0.175 | 0.161 | 0.101 | 0.112 | 0.0778 | 0.0968 | 0.136 |
| 223448_x_at | 0.396 | 0.135 | 0.195 | 0.331 | 0.358 | 0.299 | 0.262 | 0.179 | 0.229 | 0.396 |
| 223470_at | 0.144 | 0.0807 | 0.0716 | 0.0729 | 0.0605 | 0.0338 | 0.0804 | 0.135 | 0.0824 | 0.106 |

TABLE 1-continued

| | | | | | | | | | | |
|---|---|---|---|---|---|---|---|---|---|---|
| 223518_at | 0.1 | 0.0622 | 0.147 | 0.13 | 0.129 | 0.169 | 0.113 | 0.0756 | 0.129 | 0.09 |
| 223528_s_at | 0.12 | 0.142 | 0.0928 | 0.152 | 0.2 | 0.408 | 0.152 | 0.115 | 0.125 | 0.101 |
| 223570_at | 0.0646 | 0.0323 | 0.0561 | 0.0769 | 0.0441 | 0.0598 | 0.0513 | 0.0444 | 0.0394 | 0.0522 |
| 224473_x_at | 0.105 | 0.16 | 0.238 | 0.0946 | 0.127 | 0.159 | 0.0966 | 0.0751 | 0.143 | 0.0934 |
| 224721_at | 0.123 | 0.0604 | 0.139 | 0.142 | 0.139 | 0.153 | 0.0821 | 0.129 | 0.147 | 0.211 |
| 225025_at | 0.224 | 0.0586 | 0.0928 | 0.0729 | 0.0902 | 0.0988 | 0.171 | 0.0678 | 0.0287 | 0.0667 |
| 225097_at | 0.119 | 0.0323 | 0.503 | 0.13 | 0.083 | 0.203 | 0.1 | 0.119 | 0.964 | 0.17 |
| 225506_at | 0.201 | 0.149 | 0.0754 | 0.0591 | 0.0738 | 0.164 | 0.158 | 0.0911 | 0.122 | 0.11 |
| 225554_s_at | 0.242 | 0.163 | 0.354 | 0.179 | 0.179 | 0.419 | 0.307 | 0.335 | 0.441 | 0.269 |
| 225584_at | 0.0628 | 0.0442 | 0.145 | 0.122 | 0.112 | 0.0832 | 0.0513 | 0.0952 | 0.0824 | 0.0789 |
| 225841_at | 0.141 | 0.412 | 0.0484 | 0.0414 | 0.198 | 0.0338 | 0.109 | 0.138 | 0.0753 | 0.147 |
| 225947_at | 0.201 | 0.184 | 0.391 | 0.3 | 0.307 | 0.471 | 0.404 | 0.435 | 0.731 | 0.292 |
| 226124_at | 0.103 | 0.139 | 0.132 | 0.209 | 0.122 | 0.0754 | 0.0778 | 0.0856 | 0.0645 | 0.113 |
| 226139_at | 0.0768 | 0.0681 | 0.0812 | 0.0512 | 0.0379 | 0.0416 | 0.0479 | 0.0536 | 0.14 | 0.0378 |
| 226308_at | 0.0657 | 0.0263 | 0.01 | 0.01 | 0.01 | 0.0312 | 0.0231 | 0.0284 | 0.043 | 0.01 |
| 226428_at | 0.153 | 0.0801 | 0.0658 | 0.102 | 0.104 | 0.237 | 0.0966 | 0.132 | 0.0753 | 0.0311 |
| 226616_s_at | 0.236 | 0.348 | 0.323 | 0.327 | 0.228 | 0.229 | 0.174 | 0.255 | 0.24 | 0.377 |
| 226651_at | 0.0692 | 0.0777 | 0.0542 | 0.0394 | 0.0451 | 0.0442 | 0.01 | 0.0595 | 0.0394 | 0.0456 |
| 226693_at | 0.107 | 0.208 | 0.0793 | 0.199 | 0.198 | 0.117 | 0.094 | 0.0971 | 0.0968 | 0.0856 |
| 226749_at | 0.129 | 0.182 | 0.114 | 0.309 | 0.132 | 0.185 | 0.144 | 0.147 | 0.219 | 0.311 |
| 226810_at | 0.269 | 0.04 | 0.104 | 0.171 | 0.126 | 0.01 | 0.01 | 0.132 | 0.136 | 0.0356 |
| 226839_at | 0.109 | 0.112 | 0.0696 | 0.142 | 0.082 | 0.13 | 0.0744 | 0.0966 | 0.0824 | 0.0389 |
| 226917_s_at | 0.229 | 0.242 | 0.234 | 0.209 | 0.155 | 0.27 | 0.204 | 0.502 | 0.459 | 0.182 |
| 227181_at | 0.0489 | 0.0377 | 0.0445 | 0.0729 | 0.0451 | 0.052 | 0.0633 | 0.0527 | 0.0932 | 0.08 |
| 227412_at | 0.0442 | 0.105 | 0.0367 | 0.0473 | 0.0451 | 0.0936 | 0.0949 | 0.055 | 0.043 | 0.0511 |
| 227427_at | 0.0756 | 0.0562 | 0.01 | 0.01 | 0.0215 | 0.0416 | 0.0624 | 0.0211 | 0.0466 | 0.0345 |
| 227472_at | 0.0349 | 0.01 | 0.01 | 0.01 | 0.01 | 0.01 | 0.0308 | 0.01 | 0.01 | 0.01 |
| 227603_at | 0.288 | 0.095 | 0.112 | 0.122 | 0.0687 | 0.0832 | 0.0975 | 0.223 | 0.129 | 0.188 |
| 227810_at | 0.202 | 0.061 | 0.132 | 0.128 | 0.084 | 0.143 | 0.0983 | 0.167 | 0.147 | 0.152 |
| 227921_at | 0.232 | 0.15 | 0.166 | 0.0808 | 0.084 | 0.0936 | 0.372 | 0.44 | 0.0645 | 0.0222 |
| 228286_at | 0.0652 | 0.0383 | 0.0735 | 0.01 | 0.0266 | 0.0312 | 0.0496 | 0.0824 | 0.1 | 0.0689 |
| 228650_at | 0.0657 | 0.0711 | 0.172 | 0.0966 | 0.0676 | 0.13 | 0.0786 | 0.136 | 0.165 | 0.167 |
| 228736_at | 0.01 | 0.0233 | 0.01 | 0.01 | 0.0318 | 0.0286 | 0.01 | 0.0591 | 0.0538 | 0.0411 |
| 228930_at | 0.118 | 0.158 | 0.0561 | 0.0847 | 0.0625 | 0.0754 | 0.0769 | 0.141 | 0.108 | 0.138 |
| 229001_at | 0.01 | 0.127 | 0.01 | 0.01 | 0.0687 | 0.0234 | 0.0821 | 0.0444 | 0.0394 | 0.0289 |
| 229035_s_at | 0.193 | 0.0795 | 0.0793 | 0.069 | 0.0933 | 0.0728 | 0.1 | 0.145 | 0.0788 | 0.0422 |
| 229384_at | 0.114 | 0.0544 | 0.11 | 0.0572 | 0.0543 | 0.0858 | 0.119 | 0.0898 | 0.125 | 0.0823 |
| 229421_s_at | 0.01 | 0.01 | 0.01 | 0.01 | 0.01 | 0.01 | 0.01 | 0.01 | 0.0215 | 0.02 |
| 229534_at | 0.01 | 0.159 | 0.01 | 0.0414 | 0.0943 | 0.01 | 0.01 | 0.0243 | 0.0358 | 0.0989 |
| 229570_at | 0.0233 | 0.0777 | 0.01 | 0.01 | 0.01 | 0.01 | 0.059 | 0.0215 | 0.0466 | 0.0311 |
| 230048_at | 0.01 | 0.01 | 0.0329 | 0.01 | 0.01 | 0.026 | 0.0265 | 0.0343 | 0.0215 | 0.01 |
| 230791_at | 0.933 | 0.0753 | 0.0677 | 0.0532 | 0.0369 | 0.0364 | 0.0658 | 0.0536 | 0.0896 | 0.0645 |
| 230922_x_at | 0.0244 | 0.01 | 0.0367 | 0.0236 | 0.0277 | 0.0286 | 0.0436 | 0.0398 | 0.0573 | 0.0267 |
| 230983_at | 0.01 | 0.01 | 0.0522 | 0.01 | 0.0369 | 0.0338 | 0.0342 | 0.0353 | 0.0323 | 0.03 |
| 231271_x_at | 0.26 | 0.201 | 0.219 | 0.152 | 0.152 | 0.151 | 0.166 | 0.165 | 0.186 | 0.177 |
| 232524_x_at | 0.281 | 0.231 | 0.126 | 0.108 | 0.11 | 0.148 | 0.16 | 0.432 | 0.215 | 0.152 |
| 232527_at | 0.0361 | 0.1 | 0.01 | 0.0453 | 0.0451 | 0.0312 | 0.0504 | 0.0774 | 0.0323 | 0.04 |
| 233214_at | 0.0873 | 0.0885 | 0.0967 | 0.0926 | 0.0615 | 0.0598 | 0.0881 | 0.136 | 0.129 | 0.0711 |
| 233302_at | 0.0477 | 0.0466 | 0.01 | 0.01 | 0.0236 | 0.0754 | 0.0966 | 0.0696 | 0.0215 | 0.01 |
| 233429_at | 0.01 | 0.01 | 0.114 | 0.0315 | 0.0246 | 0.01 | 0.0368 | 0.01 | 0.0215 | 0.01 |
| 233440_at | 0.0471 | 0.0293 | 0.0232 | 0.0315 | 0.0277 | 0.0754 | 0.0214 | 0.0302 | 0.0573 | 0.0489 |
| 233493_at | 0.01 | 0.01 | 0.0213 | 0.01 | 0.01 | 0.0208 | 0.0325 | 0.027 | 0.0645 | 0.0222 |
| 233599_at | 0.01 | 0.01 | 0.01 | 0.01 | 0.01 | 0.01 | 0.0385 | 0.0215 | 0.0215 | 0.01 |

TABLE 1-continued

| | | | | | | | | | | |
|---|---|---|---|---|---|---|---|---|---|---|
| 234735_s_at | 0.196 | 0.102 | 0.0696 | 0.0907 | 0.0758 | 0.0442 | 0.123 | 0.0357 | 0.0609 | 0.0611 |
| 235363_at | 0.0873 | 0.052 | 0.06 | 0.0611 | 0.0523 | 0.0442 | 0.0521 | 0.0865 | 0.0681 | 0.0734 |
| 235467_s_at | 0.0605 | 0.01 | 0.01 | 0.01 | 0.0266 | 0.0468 | 0.0256 | 0.0444 | 0.01 | 0.0278 |
| 235634_at | 0.0221 | 0.0341 | 0.0793 | 0.0631 | 0.0215 | 0.0442 | 0.0333 | 0.027 | 0.0251 | 0.0333 |
| 236312_at | 0.01 | 0.01 | 0.0464 | 0.01 | 0.0728 | 0.039 | 0.0291 | 0.0417 | 0.0466 | 0.04 |
| 236875_at | 0.01 | 0.01 | 0.029 | 0.01 | 0.01 | 0.01 | 0.0419 | 0.01 | 0.01 | 0.01 |
| 237023_at | 0.0273 | 0.0329 | 0.0522 | 0.01 | 0.042 | 0.0468 | 0.0436 | 0.01 | 0.0466 | 0.0489 |
| 239496_at | 0.0343 | 0.01 | 0.01 | 0.0611 | 0.0287 | 0.0338 | 0.0231 | 0.0353 | 0.0358 | 0.0222 |
| 240130_at | 0.01 | 0.01 | 0.06 | 0.0296 | 0.01 | 0.0234 | 0.0359 | 0.0201 | 0.01 | 0.01 |
| 241395_at | 0.039 | 0.01 | 0.0271 | 0.01 | 0.01 | 0.0234 | 0.0222 | 0.044 | 0.01 | 0.01 |
| 242171_at | 0.0262 | 0.01 | 0.01 | 0.0335 | 0.0277 | 0.039 | 0.0342 | 0.0302 | 0.0394 | 0.0211 |
| 242602_x_at | 0.0506 | 0.0544 | 0.0445 | 0.0985 | 0.0543 | 0.0858 | 0.0564 | 0.0545 | 0.0502 | 0.0389 |
| 242606_at | 0.01 | 0.01 | 0.0426 | 0.0355 | 0.0523 | 0.026 | 0.0436 | 0.0243 | 0.0466 | 0.0267 |
| 243003_at | 0.0873 | 0.0909 | 0.0909 | 0.0769 | 0.0215 | 0.0832 | 0.1 | 0.145 | 0.1 | 0.108 |
| 243185_at | 0.01 | 0.0209 | 0.01 | 0.01 | 0.01 | 0.0208 | 0.0496 | 0.0467 | 0.0538 | 0.0322 |
| 31826_at | 0.0346 | 0.0944 | 0.115 | 0.0822 | 0.144 | 0.102 | 0.0966 | 0.115 | 0.14 | 0.135 |
| 35150_at | 0.0422 | 0.0297 | 0.129 | 0.106 | 0.0844 | 0.0606 | 0.0543 | 0.0608 | 0.0886 | 0.074 |
| 64474_g_at | 0.0522 | 0.0489 | 0.0636 | 0.0394 | 0.0757 | 0.0979 | 0.0752 | 0.0438 | 0.0468 | 0.0729 |
| 91617_at | 0.0411 | 0.0325 | 0.0413 | 0.0259 | 0.0552 | 0.0585 | 0.0504 | 0.045 | 0.0769 | 0.062 |

| Systematic Name | LXFE_397, Avastin_p R normalized | LXFE_646, Avastin_p R normalized | LXFL_1072, Avastin_p R normalized | MAXF_574, Avastin_p R normalized | MAXF_857, Avastin_p R normalized | RXF_393, Avastin_p R normalized |
|---|---|---|---|---|---|---|
| 200076_s_at | 0.155 | 0.0921 | 0.142 | 0.185 | 0.277 | 0.294 |
| 200631_s_at | 1.147 | 0.725 | 0.764 | 0.735 | 0.676 | 0.654 |
| 201722_s_at | 0.125 | 0.408 | 0.0518 | 0.121 | 0.0265 | 0.0761 |
| 201919_at | 0.387 | 0.392 | 0.233 | 0.314 | 0.188 | 0.356 |
| 202333_s_at | 0.103 | 0.253 | 0.125 | 0.684 | 0.0617 | 0.131 |
| 202758_s_at | 0.0632 | 0.0714 | 0.0246 | 0.138 | 0.0702 | 0.0562 |
| 203092_at | 0.0756 | 0.0472 | 0.0202 | 0.105 | 0.0899 | 0.0551 |
| 203846_at | 0.16 | 0.0786 | 0.0884 | 0.0969 | 0.0514 | 0.0902 |
| 205042_at | 0.03 | 0.0309 | 0.0567 | 0.115 | 0.0428 | 0.048 |
| 205046_at | 0.0727 | 0.0665 | 0.122 | 0.0885 | 0.11 | 0.0726 |
| 205105_at | 0.322 | 0.0613 | 0.06 | 0.137 | 0.0908 | 0.0609 |
| 205481_at | 0.01 | 0.01 | 0.01 | 0.01 | 0.01 | 0.01 |
| 206003_at | 0.0355 | 0.044 | 0.0333 | 0.0346 | 0.0283 | 0.0246 |
| 208369_s_at | 0.0436 | 0.0499 | 0.0316 | 0.103 | 0.0711 | 0.0375 |
| 208848_at | 0.244 | 0.143 | 0.0775 | 0.099 | 0.0796 | 0.0914 |
| 208951_at | 0.01 | 0.01 | 0.0491 | 0.143 | 0.0411 | 0.0597 |
| 209161_at | 0.241 | 0.121 | 0.149 | 0.272 | 0.119 | 0.11 |
| 209758_s_at | 0.01 | 0.01 | 0.01 | 0.01 | 0.01 | 0.01 |
| 211974_x_at | 0.337 | 0.168 | 0.465 | 0.228 | 0.258 | 0.26 |
| 211976_at | 0.125 | 0.125 | 0.148 | 0.134 | 0.184 | 0.114 |
| 212394_at | 0.01 | 0.01 | 0.01 | 0.036 | 0.0214 | 0.0422 |
| 213677_s_at | 0.132 | 0.103 | 0.0857 | 0.192 | 0.0702 | 0.155 |
| 214086_s_at | 0.134 | 0.146 | 0.0627 | 0.119 | 0.0788 | 0.0668 |
| 214585_s_at | 0.202 | 0.191 | 0.211 | 0.225 | 0.168 | 0.2 |
| 214672_at | 0.0895 | 0.0525 | 0.0567 | 0.0927 | 0.11 | 0.0984 |
| 214844_s_at | 0.01 | 0.01 | 0.01 | 0.0212 | 0.0223 | 0.0363 |
| 217797_at | 0.114 | 0.359 | 0.165 | 0.543 | 0.222 | 0.245 |
| 217895_at | 0.179 | 0.158 | 0.0878 | 0.227 | 0.157 | 0.0879 |
| 218625_at | 0.383 | 0.0496 | 0.01 | 0.01 | 0.01 | 0.0679 |

TABLE 1-continued

| | | | | | | |
|---|---|---|---|---|---|---|
| 218768_at | 0.33 | 0.206 | 0.282 | 0.367 | 0.259 | 0.185 |
| 218818_at | 0.0227 | 0.025 | 0.01 | 0.0317 | 0.03 | 0.048 |
| 218998_at | 0.199 | 0.0789 | 0.172 | 0.187 | 0.0762 | 0.18 |
| 219595_at | 0.0562 | 0.0414 | 0.0813 | 0.0523 | 0.0565 | 0.0527 |
| 219906_at | 0.0291 | 0.01 | 0.01 | 0.01 | 0.01 | 0.01 |
| 221214_s_at | 0.0504 | 0.083 | 0.024 | 0.0364 | 0.0308 | 0.0633 |
| 221249_s_at | 0.144 | 0.121 | 0.0813 | 0.0432 | 0.0839 | 0.01 |
| 222587_s_at | 0.0672 | 0.0588 | 0.126 | 0.208 | 0.0369 | 0.0556 |
| 222612_at | 0.0429 | 0.0252 | 0.0621 | 0.0212 | 0.029 | 0.0571 |
| 222775_s_at | 0.109 | 0.0953 | 0.0975 | 0.0795 | 0.0824 | 0.0893 |
| 222807_at | 0.155 | 0.137 | 0.045 | 0.0339 | 0.0612 | 0.0864 |
| 222906_at | 0.186 | 0.0329 | 0.0737 | 0.0339 | 0.0675 | 0.0674 |
| 223175_s_at | 0.0756 | 0.0715 | 0.0532 | 0.0583 | 0.0926 | 0.0703 |
| 223197_s_at | 0.189 | 0.0907 | 0.187 | 0.0805 | 0.164 | 0.105 |
| 223206_s_at | 0.0999 | 0.127 | 0.106 | 0.0941 | 0.243 | 0.0615 |
| 223448_x_at | 0.474 | 0.124 | 0.202 | 0.132 | 0.228 | 0.274 |
| 223470_at | 0.154 | 0.0811 | 0.0477 | 0.0924 | 0.0997 | 0.0674 |
| 223518_at | 0.0928 | 0.072 | 0.0805 | 0.0696 | 0.194 | 0.0952 |
| 223528_s_at | 0.173 | 0.112 | 0.115 | 0.0652 | 0.4 | 0.122 |
| 223570_at | 0.0539 | 0.0318 | 0.0648 | 0.0473 | 0.0589 | 0.0615 |
| 224473_x_at | 0.0787 | 0.0507 | 0.0798 | 0.0488 | 0.0934 | 0.195 |
| 224721_at | 0.145 | 0.122 | 0.121 | 0.131 | 0.0997 | 0.173 |
| 225025_at | 0.0552 | 0.0467 | 0.0559 | 0.0414 | 0.13 | 0.0659 |
| 225097_at | 0.575 | 0.12 | 0.111 | 0.0838 | 0.294 | 0.338 |
| 225506_at | 0.0875 | 0.0549 | 0.0996 | 0.0293 | 0.199 | 0.108 |
| 225554_s_at | 0.417 | 0.0841 | 0.4 | 0.122 | 0.488 | 0.164 |
| 225584_at | 0.0822 | 0.0494 | 0.0737 | 0.0799 | 0.0424 | 0.0864 |
| 225841_at | 0.0747 | 0.119 | 0.028 | 0.156 | 0.297 | 0.0322 |
| 225947_at | 0.285 | 0.235 | 0.568 | 0.365 | 0.393 | 0.258 |
| 226124_at | 0.133 | 0.0781 | 0.285 | 0.0545 | 0.108 | 0.0893 |
| 226139_at | 0.0398 | 0.01 | 0.0471 | 0.0327 | 0.044 | 0.0556 |
| 226308_at | 0.0623 | 0.0309 | 0.01 | 0.038 | 0.051 | 0.0322 |
| 226428_at | 0.123 | 0.0593 | 0.0887 | 0.0492 | 0.191 | 0.196 |
| 226616_s_at | 0.25 | 0.0476 | 0.223 | 0.121 | 0.247 | 0.209 |
| 226651_at | 0.0592 | 0.035 | 0.0498 | 0.0322 | 0.0267 | 0.01 |
| 226693_at | 0.198 | 0.0926 | 0.0996 | 0.0279 | 0.0864 | 0.105 |
| 226749_at | 0.255 | 0.103 | 0.207 | 0.0852 | 0.196 | 0.195 |
| 226810_at | 0.0597 | 0.354 | 0.252 | 0.111 | 0.0777 | 0.262 |
| 226839_at | 0.099 | 0.0628 | 0.0662 | 0.156 | 0.201 | 0.11 |
| 226917_s_at | 0.3 | 0.119 | 0.306 | 0.144 | 0.298 | 0.133 |
| 227181_at | 0.139 | 0.01 | 0.0675 | 0.0694 | 0.178 | 0.0586 |
| 227412_at | 0.0517 | 0.0245 | 0.043 | 0.0306 | 0.0777 | 0.0498 |
| 227427_at | 0.023 | 0.0238 | 0.01 | 0.01 | 0.0495 | 0.0366 |
| 227472_at | 0.023 | 0.01 | 0.0259 | 0.01 | 0.0534 | 0.0586 |
| 227603_at | 0.113 | 0.0244 | 0.111 | 0.0895 | 0.206 | 0.101 |
| 227810_at | 0.175 | 0.109 | 0.108 | 0.144 | 0.122 | 0.24 |
| 227921_at | 0.328 | 0.0815 | 0.0934 | 0.0552 | 0.188 | 0.252 |
| 228286_at | 0.105 | 0.0706 | 0.0553 | 0.0562 | 0.051 | 0.063 |
| 228650_at | 0.211 | 0.0864 | 0.117 | 0.122 | 0.115 | 0.0937 |
| 228736_at | 0.0376 | 0.043 | 0.01 | 0.0268 | 0.044 | 0.0264 |
| 228930_at | 0.099 | 0.0655 | 0.0805 | 0.0624 | 0.0801 | 0.0805 |
| 229001_at | 0.0756 | 0.0355 | 0.0409 | 0.0262 | 0.0636 | 0.01 |
| 229035_s_at | 0.0844 | 0.0263 | 0.0675 | 0.0439 | 0.168 | 0.0981 |

TABLE 1-continued

| | | | | | | |
|---|---|---|---|---|---|---|
| 229384_at | 0.0999 | 0.0389 | 0.0682 | 0.0469 | 0.111 | 0.119 |
| 229421_s_at | 0.01 | 0.01 | 0.01 | 0.01 | 0.01 | 0.01 |
| 229534_at | 0.0208 | 0.0232 | 0.01 | 0.0217 | 0.01 | 0.01 |
| 229570_at | 0.01 | 0.01 | 0.0416 | 0.01 | 0.01 | 0.01 |
| 230048_at | 0.01 | 0.0205 | 0.0218 | 0.0204 | 0.022 | 0.0293 |
| 230791_at | 0.01 | 0.01 | 0.0894 | 0.0417 | 0.0636 | 0.0688 |
| 230922_x_at | 0.034 | 0.0296 | 0.0375 | 0.0456 | 0.0408 | 0.063 |
| 230983_at | 0.0309 | 0.0255 | 0.043 | 0.134 | 0.0408 | 0.0395 |
| 231271_x_at | 0.155 | 0.108 | 0.164 | 0.0903 | 0.225 | 0.0556 |
| 232524_x_at | 0.247 | 0.104 | 0.32 | 0.16 | 0.277 | 0.108 |
| 232527_at | 0.0517 | 0.01 | 0.0477 | 0.0352 | 0.0204 | 0.022 |
| 233214_at | 0.132 | 0.03 | 0.0859 | 0.0403 | 0.0958 | 0.107 |
| 233302_at | 0.0283 | 0.0261 | 0.01 | 0.02 | 0.0432 | 0.01 |
| 233429_at | 0.01 | 0.01 | 0.01 | 0.01 | 0.01 | 0.0205 |
| 233440_at | 0.0473 | 0.01 | 0.06 | 0.01 | 0.0314 | 0.0351 |
| 233493_at | 0.0217 | 0.01 | 0.0246 | 0.01 | 0.0204 | 0.0205 |
| 233599_at | 0.023 | 0.0253 | 0.01 | 0.01 | 0.01 | 0.01 |
| 234735_s_at | 0.0981 | 0.0374 | 0.0477 | 0.0228 | 0.118 | 0.022 |
| 235363_at | 0.153 | 0.01 | 0.0982 | 0.0953 | 0.0699 | 0.0732 |
| 235467_s_at | 0.01 | 0.01 | 0.01 | 0.0218 | 0.01 | 0.0249 |
| 235634_at | 0.0283 | 0.01 | 0.0355 | 0.023 | 0.0243 | 0.0483 |
| 236312_at | 0.0751 | 0.047 | 0.0307 | 0.029 | 0.0699 | 0.0293 |
| 236875_at | 0.01 | 0.01 | 0.01 | 0.01 | 0.01 | 0.01 |
| 237023_at | 0.0482 | 0.01 | 0.0246 | 0.0257 | 0.0345 | 0.0381 |
| 239496_at | 0.01 | 0.01 | 0.0382 | 0.01 | 0.0448 | 0.0542 |
| 240130_at | 0.01 | 0.01 | 0.0232 | 0.01 | 0.0212 | 0.0264 |
| 241395_at | 0.01 | 0.01 | 0.01 | 0.01 | 0.022 | 0.0234 |
| 242171_at | 0.0371 | 0.01 | 0.0259 | 0.0202 | 0.0377 | 0.0249 |
| 242602_x_at | 0.0407 | 0.0205 | 0.0709 | 0.0684 | 0.0534 | 0.0674 |
| 242606_at | 0.0522 | 0.0293 | 0.0239 | 0.0239 | 0.0314 | 0.0337 |
| 243003_at | 0.0623 | 0.0216 | 0.117 | 0.0249 | 0.283 | 0.119 |
| 243185_at | 0.01 | 0.01 | 0.0273 | 0.01 | 0.01 | 0.0293 |
| 31826_at | 0.101 | 0.0888 | 0.0987 | 0.161 | 0.0925 | 0.142 |
| 35150_at | 0.0645 | 0.0651 | 0.0617 | 0.0868 | 0.0668 | 0.108 |
| 64474_g_at | 0.0792 | 0.156 | 0.0366 | 0.081 | 0.0625 | 0.0668 |
| 91617_at | 0.0523 | 0.119 | 0.03 | 0.0643 | 0.0668 | 0.0679 |

TABLE 2

| | |
|---|---|
| BXF | Bladder cancer |
| CEXF | Cancer of the uterine cervix |
| CNXF | Cancer of the central nervous system |
| CXF | Colon cancer |
| GXF | Gastric cancer |
| HNXF | Head and neck cancer |
| LEXF | Leukemia |
| LXFA | Non small cell lung cancer, adeno |
| LXFE | Non small cell lung cancer, epidermoid |
| LXFL | Non small cell lung cancer, large cell |
| LXFS | Small cell lung cancer, |
| LYXF | Lymphom cancer |

TABLE 2-continued

| | |
|---|---|
| MAXF | Mammary cancer |
| MEXF | Melanoma |
| OEXF | Esophageal cancer |
| OVXF | Ovarian cancer |
| PAXF | Pancreatic cancer |
| PRXF | Prostate cancer |
| PXF | Pleuramesothelioma |
| RXF | Renal cancer |
| SXF | Sarcoma |
| TXF | Testicular cancer |
| UXF | Cancer of the uterine body |
| XF | Various histologies |
| HLXF | Hodgkin lymphom |
| NLXF | Non Hodgkin lymphom |

TABLE 3

| Probe Set ID | Organism Common Name | Sequence Description | Target Sequence |
|---|---|---|---|
| 200076_s_at (SEQ. ID. No. 1) | Human | /DEF = *Homo sapiens*, hypothetical protein MGC2749, clone MGC:4376, mRNA, complete cds. /PROD = hypothetical protein MGC2749 | ccattccagctggagtcgtggggctgggcacaggggaatttttccagagctgagcc<br>tgacgtctgctctgaagaatgcttagaaggttcccagacaccagagccagatgtcc<br>cccaccaccggtcaggacctccttgaggtgcacaagcacggtctcctctgagttca<br>ccccagcccacccccgcacccactaattctgcttttcctgccccttgctccgtaaa<br>agtatcaaatactttctccttggtatctcaaggaggtttctgagataggtagaagt<br>cttgagacggaggctggccatccattcagccctgagcgtgctgagttctgtgtttc<br>tctgaatagaggtgtggaacctgaggggccagcaggcctctctgaaggcctccatg<br>gagcaaacggagccacctcgggaaagagtttaatggaatatttttgtacccgatgt<br>ttacagatgctgtt |
| 200631_s_at (SEQ. ID. No. 2) | Human | /DEF = *Homo sapiens* SET translocation (myeloid leukemia-associated) (SET), mRNA. /GEN = SET /PROD = SET translocation (myeloid leukemia-associated) | agacctggtgctctaatgccaagttatacacgggacagttgctggcatgtcttcat<br>tggctctctaaaatgtggccaagaagataggctctcagtaagaagtctgatggtga<br>gcagtaactgtccctgctttctggtataaagctctcaaatgtgaccatgtgaatct<br>gggtgggataatggactcagctctgtctgctcaatgccattgtgcagagaagcacc<br>ctaatgcataagcntaatgctgtaaaatatagtcgctgaaattaaatgccactttt<br>tcagaggtgaattaatggacagtctggtgaacttcaaaagctttttgatgtataaa<br>acttgataaatggaactattccatcaataggcaaaagtgtaacaacctatctagat<br>ggatagtatgtaatttctgcacaggtctctgtttagtaaatacatcactgtatacc<br>gatcaggaatcttgctccaa |
| 201722_s_at (SEQ. ID. No. 3) | Human | /DB_XREF = AV692127 /CLONE = GKCAOB04 | attttgattcatctgtgatagtcatggatgcttttattttccttggggtgctgaa<br>attgagctgaaaaaaaaaggctctttgaatatagttttaatttctctctacagtt<br>tttttgtttggtttgtgggctgaggaattgtaatttttaattgccttctaaaaa<br>atggaaatttaacaatgtctgatctcagctgaacaaattagatgtttcagttgct<br>cttgggtcaactggcttacagatttacatgtgcacacacacacaaatttcttatc<br>acatttcgacttcttcacttgacctaactgattatgcgaaatacccaagattca<br>tgctactgtaccacagatttgttttcacagcaataaatcttcagttctgttgttt<br>atgattccacttaacaaaaggcctgcagaagtgatttattatttgggtatttgga<br>gataatacatttgatggtatttggaaaacctttttcactccatactcagatatgc<br>ttcattgtcaaatgcatatttagattagattattgaattgtaatgtttatctgct<br>gctttt |
| 201919_at (SEQ. ID. No. 4) | Human | /DB_XREF = wp03g05.x1 /CLONE = IMAGE: 2463800 | atccatttcttgcccttcaataattgtccatgcctgccttttgttgtttacatgc<br>tcttctgcccagactgttagtaatctagggacccccttttggagctgataagtaca<br>gttcagccttttctcctcaaatatataatganctttaacattcctaagaatatag<br>gtatttctgaatgatttaaatttgaggaattttaatacataaaatacaatgtaca<br>aactttctgcccactcagatctcttctccatcatgtacttagtatttcccattaa<br>cctacacactgatttttatgctactccttgtagaaacaaaattctggtttgactc<br>agtttttgtgtttataaacttttggaatgtgtaccccgtttatgtgaag |
| 202333_s_at (SEQ. ID. No. 5) | Human | /DB_XREF = wh25c12.x1 /CLONE = IMAGE: 2381782 | ggctcatgcgggatttcaagccttaccagaggacccacctgttgctgtcagtggc<br>gcaccatctgaaaacaacatcatgcagtggaatgcagttatatttggaccagaag<br>ggacaccttttgaagatggtacttttaaactagtaatagaattttctgaagaata<br>tccaaataaaccaccaactgttaggtttttatccaaaatgtttcatccaaatgtg<br>tatgctgatggtagcatatgtttagatatccttcagaatcgatggagtccaacat<br>atgatgtatcttctatcttaacatcaattcagtctctgctggatgaaccgaatcc<br>taacagtccagccaatagccaggcagcacagctttatcaggaaaacaaacgagaa<br>tatgagaaaagagtttcggccattgttgaacaaagctggaatgattcataataga<br>caactggtctgttaatctttttcatcattgttgtgtataatttacctctcatta |
| 202758_s_at (SEQ. ID. No. 6) | Human | /DEF = *Homo sapiens* regulatory factor X-associated ankyrin-containing protein (RFXANK), | gtgacaacctcgtcaacaagccagacgagcgcggcttcacccccctcatctgggc<br>ctccgcctttggagagattgagaccgttcgcttcctgctggagtggggtgccgac<br>ccccacatcctggcaaaagagcgagagagcgccctgtcgctggccagcacaggcg<br>gctacacagacattgtggggctgctgctggagcgtgacgtggacatcaacatcta<br>tgattggaatggagggacgccactgctgtacgctgtgcgcgggaaccacgtgaaa |

TABLE 3-continued

| Probe Set ID | Organism Common Name | Sequence Description | Target Sequence |
|---|---|---|---|
| | | mRNA.<br>/GEN = RFXANK<br>/PROD = regulator y factor X-associated ankyrin-containing protein | tgcgttgaggccttgctggcccgaggcgctgacctcaccaccgaagccgactctg<br>gctacaccccgatggaccttgccgtggccctgggataccggaaagtgca |
| 203092_at (SEQ. ID. No. 7) | Human | /DEF = *Homo sapiens* putative mitochondrial inner membrane protein import receptor (hTIM44) mRNA, nuclear gene encoding mitochondrial protein, complete cds.<br>/GEN = hTIM44<br>/PROD = putative mitochondrial inner membrane proteinimport receptor | ggcaactccagacctctgggaacaagactgcgggctctgcccccagctctgccag<br>gacggctgcaagaccagctggcccgggaggggacaacgggctgttgcgggtgcgc<br>ggcagctggagacactcccccgcagggccaacccctgccctgttgctctgccctg<br>caggggtcccggcgcatggtcacctggggtgcacacaggtcacacagtgccaaga<br>ggccccagggcccagggactccccccacagcagggtgggacccgggacccgcggc<br>tcagtggcccgctagccacgtcagccaagccactttaggtccatttttttaatttt<br>aacagtgctcttccatcttgtgcataagcctgagatttggaaagaataaaacacc<br>gaattgcagaaga |
| 203846_at (SEQ. ID. No. 8) | Human | /DEF = *Homo sapiens*, TAT-INTERACTIVE PROTEIN, 72-KD, clone MGC: 4116, mRNA, complete cds.<br>/PROD = TAT-INTERACTIVE PROTEIN, 72- | tgctccacctttcagtgacatttaagacatcatattcccgtaacattatgtctc<br>agtctgatcgtctttaccagtatgaaagtcattcatttagtgctaccaaagggg<br>atacacaagccctttaggaagcagtacctctcgcctggaggatctgtgccatct<br>tggattgagaattgcagatgtgacagaatggattgaccctagttggttggtatt<br>gatgacttcagcctggaaattgcttgccttttaaagaagcatatatgggttgga<br>attatgccaaagcataggaagctgggaataagcaaacaaatgctgatatagtca<br>gcaaatttggatagtctctagggctcatcatttttcatactacctctctcttct<br>ggcctgtgtctaaggaattgtacaacataggccagggccaacaaagtggagagg<br>tggacacattttcatgttcattactaaaacaaacagcaaaactattggtttgtt<br>attctgtgttttcctcaagtcagtacatactatttggtttcaggatttctttcc<br>atttctctatcaagcatt |
| 205042_at (SEQ. ID. No. 9) | Human | /DEF = *Homo sapiens* UDP-N-acetyiglucosamine-2-epimeraseN-acetylmannosamine kinase (GNE), mRNA.<br>/GEN = GNE/<br>PROD = UDP-N-acetyiglucosamine-2-epimeraseN-acetylmannosamine kinase | ttacatttgaactatatccttcctagtgggttagtgtgaaaaagagtttggctg<br>attcctaaaactctgccagccctgcagtaatctccaggcctggttattgttcag<br>acattccatggtgattcctgggaaggaagcttggctgctcagtttctgagtctg<br>gggtgagataatgttctggaaggacatctgttctttggtgtaatctctcatggt<br>gaaatctgctctgtacatcagacaattgcattgctaccaagtttcataccaa |
| 205046_at (SEQ. ID. No. 10) | Human | /DEF = *Homo sapiens* centromere protein E (312 kD) (CENPE), mRNA.<br>/GEN = CENPE<br>/PROD = centromere protein E | aatcagcatctttccaatgaggtcaaaacttggaaggaaagaacccttaaaagag<br>aggctcacaaacaagtaacttgtgagaattctccaaagtctcctaaagtgactgg<br>aacagcttctaaaaagaaacaaattacaccctctcaatgcaaggaacggaattta<br>caagatcctgtgccaaaggaatcaccaaaatcttgtttttttgatagccgatcaa<br>agtctttaccatcacctcatccagttcgctattttgataactcaagtttaggcct<br>ttgtccagaggtgcaaaatgcaggagcagagagtgtggattctcagccaggtcct<br>tggcacgcctcctcaggcaaggatgtgcctgagtgcaaaactcagtagactcctc<br>tttgtcacttctctggagatccagcattccttatttggaaatgactttgtttatg<br>tgtctatccctggtaatgatgttgtagtgcagcttaatttcaattcagtctttac<br>tttgccactag |
| 205105_at (SEQ. ID. No. 11) | Human | /DEF = *Homo sapiens* mannosidase, alpha, class 2A, member 1 (MAN2A1), mRNA.<br>/GEN = MAN2A1<br>/PROD = mannosidase, alpha, class 2A, member 1 | acttcttctctcatgaatcatccagtcattccaatggcaaataagttctcaccta<br>cccttgagctgcaaggtgaattctctccattacagtcatctttgccttgtgacat<br>tcatctggttaatttgagaacaatacagtcaaaggtgggcaatgggcactccaat<br>gaggcagccttgatcctccacagaaaagggtttgattgtcggttctctagcaaag<br>gcacagggctgttttgttctactactcagggaaagatattggtacagaaactttt<br>aaacaagtttattgtcgaaagtctcacaccttcatcactatccttgatgcattca<br>cctcccggcactcagaatataagtgagatcaacttgagtccaatggaaatcagca<br>cattccgaatccagttgaggtgaacctgactttcacatttggattgagaatcatt<br>ggcttttatacctttcttggt |
| 205481_at (SEQ. ID. No. 12) | Human | /DEF = *Homo sapiens* adenosine A1 receptor (ADORA1), mRNA.<br>/GEN = ADORA1<br>/PROD = adenosine A1 receptor | gaggagaacactagacatgccaactcgggagcattctgcctgcctgggaacgggg<br>tggacgagggagtgtctgtaaggactcagtgttgactgtaggcgcccctggggtg<br>ggtttagcaggctgcagcaggcagaggaggagtaccccccctgagagcatgtgggg<br>gaaggccttgctgtcatgtgaatccctcaataccccctagtatctggctgggtttt<br>caggggctttggaagctctgttgcaggtgtccgggggtctaggactttagggatc<br>tgggatctggggaaggaccaacccatgccctgccaagcctggagcccctgtgttg<br>gggggcaaggtgggggagcctggagcccctgtgtgggagggcgaggcgggggagc |

TABLE 3-continued

| Probe Set ID | Organism Common Name | Sequence Description | Target Sequence |
|---|---|---|---|
| | | | ctggagcccctgtgtgggagggcgaggcgggggatcctggagcccctgtgtcggg<br>gggcgagggaggggaggtggccgtcggttgaccttctgaacatgagtgtcaactc<br>caggacttgcttccaagcccttccctctgttggaaattgggtgtgccctggctcc |
| 206003_at (SEQ. ID. No. 13) | Human | /DEF = *Homo sapiens* KIAA0635 gene product (KIAA0635), mRNA.<br>/GEN = KIAA0635<br>/PROD = KIAA063 5 gene product | ctttttcttctaagcctgtgtgttataatttaccagttccccaaaatgccatttt<br>taacgccgaactgtgtaatatacatggaaaacagctttttacaattaattttcaa<br>agttgtaattttaaagaatttgggtgtatacctatgttaatgaaacaacagaagt<br>acaaaaaagaatatcagatacaaaaatcaatcgtgaagaaaatctgttcttaata<br>tatttcattatgattgaaaaacataaaaactaacataggaaagtgaatgatcagt<br>tacttatgatatattttgtttcctcttgtggtttaataaagtgaagtgtgtgtgt<br>gtgtgtgtgtgtgtgtgtgtgtgtatacctgggggtgggcagtgctctttttcta<br>aaactaatatggcttatatatctgaattatgcccttttttagtgtgtattaggatg<br>tgggctggtttgcttttctaccacctttgtaattttatgtatcccatctcctttg<br>tgtgaattcatatattatagcaaaatacaagagacatgggactgtttgcaatac |
| 208369 s_at (SEQ. ID. No. 14) | Human | /DEF = *Homo sapiens* glutaryl-Coenzyme A dehydrogenase (GCDH), nuclear gene encoding mitochondrial protein, transcript variant 2, mRNA.<br>/GEN = GCDH<br>/PROD = glutaryl-Coenzyme A dehydrogenase isoform b | tacgccctcgacaggatgcagtttggtgtcccactggccaggaaccagctgattc<br>agaagaagctggcagacatgctcactgagattaccctgggccttcacgcctgcct<br>gcagctcggccgcttgaaggaccaggacaaggctgcccccgagatggtttctctg<br>ctgaagaggaataactgtgggaaagccctggacatcgcccgccaggcccgagaca<br>tgctggggggaatgggatttctgacgagtatcacgtgatccggcacgccatgaa<br>cctggaggccgtgaacacctacgaagtcgttcagatgtgttccttaaaaagaaga<br>tggaattctctgtagagcgtctcaatccacttttaaccatggatgagagcagact<br>ccatttaccctgaaatagcagcttctcttgagaggagagtgacatggaagcaact<br>ccgtctgctgcagctgacccccctcacactgagttcacagtgcgccctccctccct<br>cccatctgggggtagtgccttatgctgg |
| 208848_at (SEQ. ID. No. 15) | Human | /DEF = Human class III alcohol dehydrogenase (ADH5) chi subunit mRNA, complete cds.<br>/GEN = ADH5<br>/PROD = alcohol dehydrogenase 3 | gttggttgtgactgtactattctagtatagtgaactacatactgaatatccaagt<br>tctcagcacctacttttgtcaaatcttaacattttgccacttcgagatcacattg<br>ccttcctcccctccaagaggtaacaattatccacaatttgatgtttatcattcct<br>gtgttgttgtactttcactgtgtataacctaaaccatctactctttagtactgtt<br>ttatatatttttaagcctcatacttgctcattctacagctttttttcactcattat<br>tgtataattatatctgaagctctcgttcattaattttagtcctgtgtagcagaat<br>tcaattacgggaaactaccataatttatctgttctccagtccagttgaaggcatg<br>aagttgttgccagtttctgtattataacactgtagtggaacattcttctgcattg<br>ggctactcgcgtgttacctaagacgt |
| 208951_at (SEQ. ID. No. 16) | Human | /DEF = *Homo sapiens*, antiquitin 1, clone MGC: 1569, mRNA, complete cds.<br>/PROD = antiquitin 1 | gtggcacagtggtctatgggggcaaggttatggatcgccctggaaattatgtaga<br>accgacaattgtgacaggtcttggccacgatgcgtccattgcacacacagagact<br>tttgctccgattctctatgtctttaaattccag |
| 209161_at (SEQ. ID. No. 17) | Human | /DB_XREF = qd24g04.x1<br>/CLONE IMAGE: 1724694 | tgttcgaatgccttatagccttcctcacagcacccaggattgtgactgactctgc<br>atttttaattcttgaaacttggctttccataacatggtacatgcttcaggactac<br>atatgacccagagagcaaggtggctgaactatagtctggaagccctcaggtaaag<br>aggcacatctcaccactcattggttaaacaatgcatcatagcgagcacttttcct<br>ttccctggagaatgggatgtgaagcagtagaccgcagccacgccgatggttatac<br>agtgaagaagacttcacctcttcctattgagtttgcttggaatgctgacagcatc<br>aggcaactctgaactgaacatttgctttgtcagaaaatatcttttttttttacttt<br>gaagtttggcaaccttcatgttaccccaaagcaaaaccattgtgtcaggagtcaa<br>acaaatgtttagaaagcaaacatgacgtctctattgtacaacctcc |
| 209758_s_at (SEQ. ID. No. 18) | Human | /DEF = Human microfibril-associated glycoprotein-2 MAGP-2 mRNA, complete cds.<br>/PROD = microfibril-associated glycoprotein-2 MAGP-2 | taatctggtgaatgatcccgctacagatgaaacagttttggctgttttggctgat<br>attgcaccttccacagatgacttggcctccctcagtgaaaaaaataccactgcag<br>agtgctgggatgagaaatttacctgcacaaggctctactctgtgcatcggccggt<br>taaacaatgcattcatcagttatgcttcaccagtttacgacgtatgtacatcgtc<br>aacaaggagatctgctctcgtcttgtctgtaaggaacacgaagctatgaaagatg<br>agctttgccgtcagatggctggtctgccccctaggagactccgtcgctccaatta<br>cttccgacttcctccctgtgaaaatgtggatttgcagagacccaatggtctgtga<br>tcattgaaaaagaggaaagaagaaaaaatgtatgggtgagaggaaggaggatctc<br>cttcttctccaaccattgacagctaacccttagacagtatttcttaaaccaatcc<br>ttttgcaatgtccagctt |
| 211974_x_at (SEQ. ID. No. 19) | Human | /DB_XREF = AL513759<br>/CLONE = CL0BA008ZD02 (3 prime) | gagagagtatgctctgtgtcgtcccagacatttctgcattccgagaaggttggag<br>atgggtccggcaaccagtccaggttccagtaactttggtccgaaatgatggaatc<br>atttattccaccagccttacctttacctacacaccagaaccagggccgcggccac<br>attgcagtgcagcaggagcaatccttcgagccaattcaagccaggtgcccccctaa<br>cgaatcaaacacaaacagcgagggaagttacacaaacgccagcacaaattcaacc<br>agtgtcacatcatctacagccacagtggtatcctaactaccgtctttttgctagg<br>acttaaactgacttgagtgtggcaaaaagttaacaaaaaaggagaaaaaatgaac<br>aatcgtttgtggtttcttgggaaaacttttcataccaggtgatactattcaaaaa<br>ccccgttgtctccctgcaagtgctgatttg |

TABLE 3-continued

| Probe Set ID | Organism Common Name | Sequence Description | Target Sequence |
|---|---|---|---|
| 211976_at (SEQ. ID. No. 20) | Human | /DB_XREF = xz95g12.x1 /CLONE = IMAGE: 2872006 | tgtcttcacagcgtccctaaggaagattttgcagcactctctggagctgaggggagtgaaatttggtccagagaaggcggaaggaaatagttttcctgtttccttttctcgaggtggatgtcctcaggcttccttcacacctccttctcatgggtncggntggcagtacagtcaggctgtggaggagggctgagaagaaaggggcactggtccagccccanggtttggtctgagacaggtacacagcagataccatcccaccttcctctctaaagaacaggccagccacacatataacccttccctactttactaatgtatccctatgtggtaccagcaatggaggacaggcagacttacccctgccatctagagagaatgttgttattacccgtaaaacttgaccaccccatatcccactcctttttgtaaaaacaaatgcttaaacctgtgagcctgccgttcctttctatgtgttaatcagtttccttccatttgagctgt |
| 212394_at (SEQ. ID. No. 21) | Human | /DEF = Human mRNA for KIAA0090 gene, partial cds. /GEN = KIAA0090 | gcacctggcccataaattgtcatacttttaaagagcctattacacaaagtatcatcagaatcatcccaagactcatttcctgattcctaattatttaaaattttgcttttaggcgaggcatggtgnctcaagcctatnntcccagcactttgggagncnaaggcaggcagatcatttgaggtcaggagtttnngaccagcctggccaacatggtgaaacctgaaaccccatctctaccaaaaaaatggaaaaatttagccaggtgtggtggtgcatgcctgtaatcccagcctcccgagtagctggggctcaggcgtgcgccaccatgcccggctaatttttgtatatttatggaaatgccaagagatagttcaatctgcctctctggcaagccatggacaccaggtctgacaaactctcttactccttaagacaaatgctcacctgatcaatatggggaaataagctgcatggtaccataatttctattctaaaagggaaaagtatctctttggtattgctttggaa |
| 213677_s_at (SEQ. ID. No. 22) | Human | /DB_XREF = 602507842F1 /CLONE = IMAGE: 4604891 | gatcaacttacctgtctgatcctcgtcttacagcgaatggtttcaagataaaattgataccaggagtttcaattactgaaaattacttggaaatagaaggaatggctaattgtctcccattctatggagtagcagatttaaaagaaattcttaatgctatattaaacagaaatgcaaaggaagtttatgaatgtagacctcgcaaagtgataagttatttagagggagaagcagtgcgtctatccagacaattacccatgtacttatcaaaagaggacatccaagacattatctacagaatgaagcaccagtttggaaatgaaattaaagagtgtgttcatggtcgcccatttttcatcatttaacctatcttccagaaactacatgattaaatatgtttaagaagattagttaccattgaaattggttctgtcataaaacagcatgagtctggttttaaattatctttgtattatgtgtcacatggttattttttaaatgaggattcactgacttgttttt |
| 214086_s_at (SEQ. ID. No. 23) | Human | /DEF = *Homo sapiens* cDNA FLJ11118 fis, clone PLACE1006011, highly similar to *Homo sapiens* mRNA for poly(ADP-ribose) polymerase-2. | gacatgtcttccaagagtgccaattactgcttnnnnnnncgcctaaagnatacaggactgctgctcttatcagnngtagctctaggtcagtgtaatgaactactagaggccaatcctaaggccgaaggattgcttcaaggtaaacatagcaccaaggggctgggcaagatggctcccagttctgcccacttcgtcaccctgtaagtactcagaaccaggaggactagaagactccttttggccagataagactacgttctctattgcagcttctgaaccagagactgatgttgacacactttttttccatttggcaggaatgggagtacagtgccattaggaccagcaagtgacacaggaattctgaatccagatggttataccctcaactacaatgaatatattgtatataaccccaaccaggtccgtatgcggtaccttttaaaggttcagtttaatttccttcagctgtggtga |
| 214585_s_at (SEQ. ID. No. 24) | Human | /DEF = *Homo sapiens* mRNA; cDNA DKFZp547l194 (from clone DKFZp547l194). /GEN = DKFZp547l194 /PROD = hypothetical protein | ttctgatgtgccagaaaccgccctgagatctgccggtcatctccatggacttctgcaccccattccataccctcttcacctggggtaccccttccagttttccccttgcttcccaggcccttgacatggcttacctgccttcactcccagcaccttgcccaacaggataagctggatccccttggccttctgaatatcccagtgtcttcaggtttcccaagaccacttccctgtgggcttccaaaatggcctttatcatttctccagtctgtcaccctcctttcctgctcccatacacccaaggcttgtttcttcccctgtaaaaaccactgcctcaatctctggttcactcaactagtcaccatgtcctgaggcatgaagcctcctcagctcttggaattgctggcaaggggtgactgcctctgagtcattgtgttttttcaaagtgatttcttttctgtagctttttgacctaagatctcagcaatttgaacactaacctctcccctcctggctcaagaattactccgaagtcagtctgcag |
| 214672_at (SEQ. ID. No. 25) | Human | /DEF = *Homo sapiens* mRNA for KIAA0998 protein, partial cds. /GEN = KIAA0998 /PROD = KIAA099 8 protein | tgaagcatccaccagcacttcaaggggtccatagtattttttttttgctgcctcaaagtccccaaagccttcgagcagaagtggcagtagatggttgccaatcagccaatgcagactttcactgggacaacaagaaagcagatcttctgggttttgatggaacttggcagtggggacattcagctgatgcattatataccccgtcagagcacacttgtatcttttaccttccctttgccccatgcccccaaactgcttaggtcttctctgtccctttactgctgctgcacagagatgatataaaagaggctctttggctatttgcattntgcttcctcttcttttccagattacagtatgaagctttattttctttgtacaagcttaaaatttcaacatcatcatccgccaaagttgttcctccccttttcggaggatctaggggaaagaggagcattcatcacaagtttcctagagagaggagacaaatcggtgtgccattgacaacatgagccagggtaaaggcaccctttgg |
| 214844_s_at (SEQ. ID. No. 26) | Human | /DEF = *Homo sapiens* mRNA; cDNA DKFZp566A0946 (from clone DKFZp566A0946); partial cds. /GEN = DKFZp566A0946 /PROD = hypothetical protein | gtcctggctaattgtgtggtcattggaaaactctgcaatacaataattttctttattttctttttctttttaaattcttagtgtaattgaaacgtgctctatagatattgactctgtgttccctcttttacagctggacagaaagaagtcaatgtcacgaaatgattttctattgtagatactttgtcccttgcacttctctgaatctgtccttttgtggattcttgtgatttccttccaagtgtttcagttgtatgacagtcagtattgacaataaaatggcttttaattatttgttatttgtttacaccctattcctcagttattattactgtggttctgattaactactggaaattatatttgattatatcaccaattagttaaatcagtgcttcgactcactcttatctgttctgttcaaaactatttgttcaaagaacccgttagtgttgtttacagggttacagtttctctcacatgctttcctcaccccnttaccccnctttttgaaagcctttatttgttcggagtctctt |

TABLE 3-continued

| Probe Set ID | Organism Common Name | Sequence Description | Target Sequence |
|---|---|---|---|
| 217797_at (SEQ. ID. No. 27) | Human | /DEF = *Homo sapiens* hypothetical protein (HSPC155), mRNA. /GEN = HSPC155 /PROD = hypothetical protein | atgcctgacggatcatttcaaacctttgtgggccaggaatgtgcccaaatttggactagctcatctcatggctctggggctgggtccatggctggcagtggaaatccctgatctgattcagaagggcgtcatccaccacaaagagaaatgcaaccaatgaagaatcaagccactgaggcagggcagagggacctttgataggctacgatactattttcctgtgcatcacacttaactcatctaactgcttccccggacaccctccacctctagttgttactaagtagctgcagtaggcattgctggggaagaaacaaacacacaccaaacagtactgctacttagtttctaaggctgcacagggaagggaaagactgggctttggacaatctagaggtaatttatatccgcccccaggtggagcaacatgcgattctggaggcacgggagtaactgaaagtgagtacatatagtctttctggtttc |
| 217895_at (SEQ. ID. No. 28) | Human | /DEF = *Homo sapiens* hypothetical protein FLJ20758 (FLJ20758), mRNA. /GEN = FLJ20758 /PROD = hypothetical protein FLJ20758 | catagctgctggaatcacacctgagaactgagatataccaatatttaacattgttacaaagaagaaaagatacagatttggtgaatttgttactgtgaggtacagtcagtacacagctgacttatgtagatttaagctgctaatatgctacttaaccatctattaatgcaccattaaaggcttagcatttaagtagcaacattgcggttttcagacacatggtgaggtccatggctcttgtcatcaggataagcctgcacacctagagtgtcggtgagctgacctcacgatgctgtcctcgtgcgattgccctctcctgctgctggacttctgcctttgttggcctgatgtgctgctgtgatgctggtccttcatcttaggtgttcatgcagttctaacacagttggggttgggtcaatagtttcccaatttcagg |
| 218625_at (SEQ. ID. No. 29) | Human | /DEF = *Homo sapiens* neuritin (LOC51299), mRNA. /GEN = LOC51299 | attcaagagagagatgtccacggccgaaacatacggtgaataattcacgctcacgtcgttcttccacagtatcttgttttgatcatttccactgcacatttctcctcaagaaaagcgaaaggacagactgttggctttgtgtttggaggataggagggagagaggaaggggctgaggaaatctctggggtaagagtaaaggcttccagaagacatgctgctatggtcactgaggggttagctttatctgctgttgttgatgcatccgtccaagttcactgcctttattttccctcctccctcttgttttagctgttacac |
| 218768_at (SEQ. ID. No. 30) | Human | /DEF = *Homo sapiens* nuclear pore complex protein (NUP107), mRNA. /GEN = NUP107 /PROD = nuclear pore complex protein | ttggatgccctaactgctgatgtgaaggagaaaatgtataacgtcttgttgtttgttgatggagggtggatggtggatgttagagaggatgccaaagaagaccatgaaagaacacatcaaatggtcttactgagaaagctttgtctgccaatgttgtgttttctgcttcatacgatattgcacagtactggtcagtatcaggaatgcctacagttagcagatatggtatcctctgagcgccacaaactgtacctggtattttctaaggaagagctaaggaagttgctgcagaagctcagagagtcctctctaatgctcctagaccagggacttgacccattagggtatgaaattcagttatagtttaatctttgtaatctcactaattttcatgataaatgaagtttttaataaaatatacttgttattagtaattttttcttttgcattaccatgtaaaatttagacatttgaattttgtacttttcagaatattatcgtgacactttcaacatgtagggatatcagcgtttctctgtgtgct |
| 218818_at (SEQ. ID. No. 31) | Human | /DEF = *Homo sapiens* four and a half LIM domains 3 (FHL3), mRNA. /GEN = FHL3 /PROD = four and a half LIM domains 3 | ttttctaaaccacctctgggactcagctccccccgccaaaaaaaatgggtctccttctgggctccaggattgtctccccactccagcatccccaaactggtactccctgacccaggcccccaatcctgggctcttacagagcatccatgagtcaagccccctccccacacctggactccagaattcaccctctcccctgcagtctgggttcccagactgagtcctctccccaaatcagggctctagacccgagccctccaaacctggactctgggacttaggccccttaaatctagacttctctttataggtttcaggtctcctatgggtgcctgggaagtccttgaaagtggactgttctcaggcttgacctgccccacccc atccccgcggttgaggctgtgggggcagcagatcaggagcccactgataaggggccctagggtacagggtgctgcccagcaggtcgccaccgagtgtcttctcattttatttcagctccattttgnccatagatgggcagaggggtgagattggctcatccccc |
| 218998_at (SEQ. ID. No. 32) | Human | /DEF = *Homo sapiens* hypothetical protein FLJ20457 (FLJ20457), mRNA. /GEN = FLJ20457 /PROD = hypothetical protein FLJ20457 | cagtcttctataatgtgcctaccaaaaagcctagtcctagcccatctgcctcaactcctctcccttttaggttgtagggaagaggccggagtgtagagtatattatatcttctgtccccttatgccaacaagatggccttcccctctgaaacaaagtaaaactgcaacactgtgacttcttaaatgagggatatgtgaaaaggctatgaaaaatacaaaggctttcctaggaaatgtgttataatgcagcgggaagctaattcttgaaatatgcacattatagttactcagtctcacatactctagttactggcaaagaagttactgagaatatggtcattcaaaggcataggggcctttgaatggaacaaatgctttcacatcatttaaagtaaaaaaaaacctccaacaactgtgaatttat |
| 219595_at (SEQ. ID. No. 33) | Human | /DEF = *Homo sapiens* zinc finger protein 26 (KOX 20) (ZNF26), mRNA. /GEN = ZNF26 /PROD = hypothetical protein FLJ20755 | ataatatcccccagtattttccatattaaatgctaattatcttttgatttcttttttcataagcagatctggcatttattacagggctgccgcttaagagaactcattataatgaacgtttattatatttgcagttccatgcctgttgtccattgattgacatgagcacccctgtttctctggagaaatacctcccctctctggggtgcttcctgtggtagtgtctttcaggtatccgttccactagctacaggtgagcattttacccattgttggataatggtaatctctttttcagaattttgagtctgtaattcatttgtacatgaaccagaaaatgtgggaactcattcattcttgtcccagaattctgttgagaacatccattcattctggctaattgattacaagaataactgtggatacgatccctttagaacctgcttctctgatctgt |
| 219906_at (SEQ. ID. No. 34) | Human | /DEF = *Homo sapiens* hypothetical protein FLJ10213 (FLJ10213), mRNA. /GEN = FLJ10213 /PROD = hypothetical protein FLJ10213 | ggatcagctcaagaccatgggttggagaattaatgttcacacttctatttggagactttgaatcccctctacacaagctacgcaagtcaagttagttgccaagaaagcacagatgacaacctattaatgctgtgagaatgtttctagatcagtgcatggatggctccattgctctacgggccattgtgtctgagatcccagtctttgaggagaaaaaaaacaatggttaaaaaggcattggggaaatattttgagtttgggggtgtactttgccaccccattattggggagctgtcaccacgaatgttcccaaacttagcaacagcggcaaactactgggccaagatgagcaaccccacatttttgggatttaaagctcctgatgttataccaggatcaaccatcacactccctttgcttcaaatggcgtctaccccgtaagatcttgaggg |

TABLE 3-continued

| Probe Set ID | Organism Common Name | Sequence Description | Target Sequence |
|---|---|---|---|
| 221214_s_at (SEQ. ID. No. 35) | Human | /DEF = *Homo sapiens* DKFZP586J1624 protein (DKFZP586J1624), mRNA. /GEN = DKFZP586J1624 /PROD = DKFZP586J1624 protein | caggaaggaagggcgcagcgtcccctccttcagaggaggctctgggtggggcctg<br>ctccccatcccccaagcccacccagcactctcattgctgctgttgagttcagct<br>tttaccagcctcagtgtggaggctccatcccagcacacaggcctggggcttggca<br>ggggcccagctggggctgggccctgggttttgagaaactcgctggcaccacagtg<br>ggcccctggacccggccgcgcagctggtggactgtaggggctcctgactgggcac<br>aggagctcccagcttttgtccacggccagcaggatgggctgtcgtgtatatagct<br>ggggcgaggg |
| 221249_s_at (SEQ. ID. No. 36) | Human | /DEF = *Homo sapiens* CEBP-induced protein (LOC81558), mRNA. /GEN = LOC81558 /PROD = CEBP-induced protein | gagaagacgccacagatttccttccctctcctccaggagaccataagatagatcc<br>cccatcctctcagccctattcccatgcctccctctcattggaggagctgaccaaa<br>gcagccctaacgggccataacacttgaccaattcagctgctggcagagggaggaa<br>acaagtgttttcccaagtggcattttcatctcgctttcaccctgactaaagattg<br>tcttaagtagcagcccagcccgcccagccccaggtgggtagtggggaggagagct<br>ggcattcctccaggtggcaaatggcgactctatactctccgcccgccccagggct<br>ggatggattagaaaaatccctatttttcttgtatcgatgtagagactctattttc<br>tcccaaagacactatttttgcagctgtttgaagtttgtatattttccgtactgca<br>gagcttacacaaaattgaagaatgttaatgttcgagttttcttatcttgtgttt |
| 222587_s_at (SEQ. ID. No. 37) | Human | /DB XREF = 602127301F1 /CLONE = IMAGE: 4284168 | gacatttgggatttacttttctccaatacctgccaatacagaaaactattatcag<br>ttgttattgttatcccttgaaaagcgagggtgacaaaaacaacaaaacaccgtta<br>taaacacatcaaaggttcattctgactgaggtaagactttccaagcccttgttag<br>attaggccttataaaacttgtgtgcattataacctaagctgtgcaacctggtgaa<br>gccaagagtgaactgatgtttcatttatattttcatccaaatgacattatctgca<br>cgtttttaaaatttaaaaacaaaggactatttaaaaatacagtttattaacaaac<br>gtgaaactactttctgttacattaggtgttccctagtgtttcttaatttct |
| 222612_at (SEQ. ID. No. 38) | Human | /DB_XREF = yw86h04.s1 /CLONE = IMAGE: 259159 | cagaatagccaagaaatccctccttttcaacgctctgtgcctggnaaccattaga<br>ggagntttaaaaaccatccctcatagcccacaattttgggtcaactctcaaaatt<br>gggaataagaaaactggcactgttgggagaaaaatcgttcttactgaaacatgaa<br>ctggctcaggcaagcaaatagcgggagtcggcacaggaaggagtgtgtgctgcgg<br>ggatgcgtggtggcgtcaccttcaaaactaaagtggtgccaggcggacagatgag<br>tccttgatcttgtttcctgatcttgtttccatttgactgaattctgaaccttcat<br>tgtcttcacagtcttgccacttgcctagtgaggcttttccgaacctggaaggaga<br>cgtctagaaatcccaactttgctgtgtaaggaccattagctgcaagtcagtggaa<br>gtctatagaaagcagtgtgaattccatagtggtcttgacttct |
| 222775_s_at (SEQ. ID. No. 39) | Human | /DEF = *Homo sapiens* cDNA: FLJ22567 fis, clone HSI02118. | ttgatggattttcatttcttcgcacttctgagacggcaaagccaaccacttagaa<br>gccttccacatctttgtcacctgcctggctcctgctctctgatgtacctctgggt<br>agtgagatggaaatggtgcctgcagaagttggggagaaggatacttttgcacagc<br>ctccatgatgtctttattgcaaatatggatgacaagggtctctgttacaggggcc<br>tcagagcaccttcgtttctcctctagaccagggacaggtgtagagataaggactg<br>gcaaccagagcctcagcatccaaagatggactgaagtgggatggctgacaggcac<br>atnacttacgggaaagggaatttcatacatacgattttttgttttgtgggtaggag<br>ggcttatcatcaacactg |
| 222807_at (SEQ. ID. No. 40) | Human | /DB_XREF = 7b44a06.x1 /CLONE = IMAGE: 3231058 | taagatgcgctgatctctggtggttgtcactagttctnctaggtgataatgattt<br>acccatagatggagctgttggatattattttattgtacaaattcatgtttaaaaa<br>actttgtgactgtttctagttaagtaatttttttaacctttcttgggtcatagact<br>tctttggtaaactatgaactctcaccaaaaagatacacatgcaacatgttaaata<br>catgttagactttgcatacaattttaggggctcatgggcctctaagcctatccat<br>gtattccaggttaagccctctgttatgatcaatccatt |
| 222906_at (SEQ. ID. No. 41) | Human | /DEF = *Homo sapiens* cDNA FLJ10557 fis, clone NT2RP2002537. | gagtcatcacactgttggaatagtctgctctttnacatgctcaggtagggaaaat<br>aggaccaaatatatttccanagtgcctaccactgtgtcatgtttacagtgagagt<br>ttaaatattgttgatgtcctgactctgtgagctcatagggagtatcttcatagta<br>atgacatttgatcagccataaaatttacattatgttcatatgcacccaaaaaagc<br>tagtcaggtaatgaatacccttgaagtgaatagcaattttgatttaggcagtgtg<br>ttaggccatccttg |
| 223175_s_at (SEQ. ID. No. 42) | Human | /DEF = *Homo sapiens*, Similar to feminization 1 a homolog (*C. elegans*), clone MGC: 4216, mRNA, complete cds. /PROD = Similar to feminization 1 a homolog (*C. elegans*) | tgttctttcagctgctccaaggattgagacccaagtcatcatgaaaaaggcccaa<br>gtacagtcttaatgcgataaatccactagctaagacgtcgagtgccaagaccagc<br>cttccagccgaggtttggacaaagtctcaggttcccgtgactcagggtaaggtgc<br>tggggctgccagaggacctgccccagcaagattttgtcaagagcgagactccat<br>cagcccaggcagacgggagcaggttcttggccagcgtagacagcagcaaacagca<br>gcagggaagccattctcactgcatcctccctgcagtagccacggccaggccctta<br>ggaggagcagtgaccgggggtgtccagaaatatcctgtccctggatggaaactag<br>gtctcgtttggatttttttttttttttttttttttttgccgtgttaggaaattatttatt<br>aatttacaagacaggttttaactcagccgaggtgggaaatggtgtccctgtccct<br>cccaaagcacagagcacagaaatgaggccgtttacatggcgagtctccgtgctgg<br>tgtttaagtc |
| 223197_s_at (SEQ. ID. No. 43) | Human | /DB_XREF = wf38a09.x1 /CLONE = IMAGE: 2357848 | tgttcattttccaactgcactaattgtgcatattactctgcctaatcttgtgcat<br>gttttcattgatttccctctcccggcttttgcttctcttgaaactgttgcccagt<br>cacttctgctccaattctcttcctctctaaatagtagtttaattactgccacatc<br>tccatgcatcagcaaaatgttggtgacatttttctagcctggcagaacagattac |

TABLE 3-continued

| Probe Set ID | Organism Common Name | Sequence Description | Target Sequence |
|---|---|---|---|
| | | | ttaaagctatttcanttcaaagcagactgaatgtgacttcatctaaaggcagcat taggtactgcatggaaataggtcattaacttgaaactcttatcaaaatatatttt accagtttccagaatttccagtacaggaccgcctgaagagagagccattgttcaa ttccaattcagtgtgagtgacaaagtgaaatttagaagtgaagttgtctatttga tatttaactctttattaaatctttctttaaatttctgcctgtcagtctatattgc tgtttttattatacatcagtttctttgtataacttgtgagttcccatgtgttttg t |
| 223206_s_at (SEQ. ID. No. 44) | Human | /DEF = *Homo sapiens*, HSCARG protein, clone MGC: 11351, mRNA, complete cds. /PROD = HSCARG protein | atttccgggacattggcgttcccatgaccagtgtgcggctgccctgctattttga gaacctcctctcccacttcttgccccagaaagccccagacggaaagagctacttg ctgagcttgcccacaggtgacgttcccatggatggcatgtccgtgtctgacctgg gtcctgtggtgctcagccttttgaagatgccagaaaaatacgtcggccagaacat cgggctgagcacttgcaggcacacggccgaggagtacgctgccctgctcaccaag cacacccgcaaggtcgtgcacgatgccaagatgactcctga |
| 223448_x_at (SEQ. ID. No. 45) | Human | /DEF = *Homo sapiens* brain my045 protein mRNA, complete cds. /PROD = brain my045 protein | tttgcccagtttgagccagattccacagagtatatcaaggttcatcacaagacct atgaagatatagataaacgtggaaaatatgaccttttacgttcaacaagatactt tggtggaatggtgtggtattttgtaaataataaaaagattgatggtttgctgatt gaccagattcagagagatttaatcgatgatgcaaccaacttggtccagctgtatc acgtgctccatccagatggccagtcggctcaaggggccaaggatcaggctgctga gggaataaatttaatcaaggtctttgcaaaaacagaagcacagaagggagcctat atagaactaacactgcagacttatcaagaagcactcagtcgccattctgcagctt cctaaaaatattttaaaaatacatttattttactaaatactgactacatttctct gttaatattgagctaaatgttaaaaaatggccagattaaaagatatcaatttgta gttctccctacaaagcaaaaattattaccctactcacttttcgtaggctacaagg atatttgagtgcctggtta |
| 223470_at (SEQ. ID. No. 46) | Human | /DEF = *Homo sapiens* PIG-M mRNA for mannosyltransferase, complete cds. /GEN = PIG-M /PROD = mannosyltransferase | ttttaacaaagtctgcacctcccagtactttctttggtacctctgcttactgcct cttgtgatgccactagtcagaatgccttggaaaagagctgtagttctcctaatgt tatggtttatagggcaggccatgtggctggctcctgcctatgttctagagtttca aggaaagaacacctttctgtttatttggttagctggtttgttctttcttcttatc aattgttccatcctgattcaaattatttcccattacaaagaagaacccctgacag agagaatcaaatatgactagtgtatgttccacaccctctgctactgtgttacatt ctgattgtcttgtatggaccagaagagagctttgggacatttttctgaacattc taagcattctagtgaaagttcccatgttccaacagaacttaaaagcaatgtttgc cttatatataaaaggtacacaataattgaggtccaccttctaggaaatcctagga ctcgtttatttgggacatggt |
| 223518_at (SEQ. ID. No. 47) | Human | /DEF = *Homo sapiens* DNA fragmentation factor DFF35 (DFF35) mRNA, complete cds. /GEN = DFF35 /PROD = DNA fragmentation factor DFF35 | ttttgttcacctctgcagactgtgaatcctagctgccagtttgcctattatatgc caaggcatttgcaaaaatctcattaatctaaatcaaaatagctttaaagaaaaat gcatacacttcctcagatcatcaaacagactctggtccaaggttggtaatgaaat gactgttcctgacagggaggaatagcagggcccaatcttctgagatggcttctgg gtctttccatggtcagagaagatctatagtccgtcctgaggtctgtcaatgtcac aggaaaaggcaaacttgaggggatcgtcgcctgctggctaagaccagggagctaa aaacttgaggaagggaacctgcctgggtgggtgctacttctgattcattgtcctt gtccctgtcataagtacctccctattgtagatagaagggaaggaaactgttgact tgagcttggcta |
| 223528_s_at (SEQ. ID. No. 48) | Human | /DEF = *Homo sapiens* false p73 target protein mRNA, complete cds. /PROD = false p73 target protein | ggagaatggaacaaaagctgggcacagccttctcatggatgccagggatctggtc cttaagggaaaagggaagtcacctttggaccctcgacctggttttgtctttgccc cgtgtccccatgaactcccttgtccccagttgaccaacctggcctgtagcttctc acaggcgtaccatcccatccccttcagctggaacaagaaaccaaaggaagaaaag ttctctatggtgatccttgctcggggggtctccagaggaggctcatcgctggcccc gtatcactcagcctgtccttaaacggcctcgccatgtgcattgtcacttgtgctg tccagatgggcacatgcagcatgctgtgctcacagcccgccggcacggcaggtat ggggggtgtgaccaaaatcagtgggatgtggcaggaagctgcagcccacgccagc atctgttcccacagggatttgtatcgttgtgcccgtgtcagctcctggggagatc ttttacctgtgcttactccgtctgcgtttcctccatctacggctcaggatccctc tgagagttgatgag |
| 223570_at (SEQ. ID. No. 49) | Human | /DEF = *Homo sapiens* mRNA; cDNA DKFZp434H152 (from clone DKFZp434H152) complete cds. /GEN = DKFZp434H152 /PROD = hypothetical protein | ttttgggaggttgttgtgggagatggttgatttaggttttcaaaagctagaaata aaatttacatgccttagatttcataaaattctgctctaattgggtggaaggtgct gtatctaacttgtgttcctcctaaggttatgtcctaataactattcttttaggag tatacttctactttatagaaggttgcttttctttttaatttttttctaacaaagaa aagaataaagtatttattaataagaaccagaaagcacttgaaactgatgtttta atggctcatttagggtagatttatttatctcattaacttaaaacagctatgtgta tgaaataggtcacaacagaacttgaacaccaggttggtgtctgagcaatcccttt cttatgggaaaaacaatgttcttgtttgaacagagggtatcattgcagtcagtat tcacgtgtatattgttatataagttgtataatatgcttgtaaaggctgagggtga gctgtatctggatgccttttttacaatttgatt |
| 224473_x_at (SEQ. ID. No. | Human | /DEF = *Homo sapiens*, clone MGC: 2586, mRNA, | gatggccccaaaggctgagggccccaaagccacttgtctcctaggatccaggcct ctgggcttctgccaagaactcagggtggccctatgacttggaggagcaagatcag |

TABLE 3-continued

| Probe Set ID | Organism Common Name | Sequence Description | Target Sequence |
|---|---|---|---|
| 50) | | complete cds.<br>/PROD = Unknown<br>(protein for MGC:<br>2586) | accgctcaaaggtccccgtgttcactgttacccagaggctcttgttactacccac<br>ttcattccccaccgctgccagtgccactgccaaccctgttcacaggcgcttccag<br>cccactccagccaggggagcagggaagaagaaggggctccctcctcttcacattc<br>cccccgaccccaaagccagagaaagccagatggcaccagctgctccggatgtgcc<br>tgcccacattgggggacagggccgggcctgggctcggttcccaggtttgagctct<br>gcagcctctctcctggagtgaggggctgaagtcagaccaaaggaagaactcaga<br>aatgtcttgtttatttgtgtttgtgaccaagcagcctctcccttcacccaggttt<br>atggcctcgttttcacttgtatattt |
| 224721_at<br>(SEQ. ID. No.<br>51) | Human | /DB_XREF = ts83b12.x1<br>/CLONE = IMAGE:<br>2237855 | gcagaagaaagtcttcccacaaccccattttatttcatattgggaaaacacaggc<br>aacagcaggatgaaaaactaaacgaaactttagagaatgagctggtacaactacc<br>cttaacagaaaacatacccgcaattagtgagcttcttcacactccagcccatgtc<br>ctgccatctgctgctttcctgtgctccatgtttgtaaattcattgctgctgtcta<br>aagagactaagagtgctaaggaaattcctgaagatgtagatatggaagaagaaaa<br>agaaagtgaagattcagatgaagaaaatgattttaccgaaaaagtccaggataca<br>agtaacacaggtttaggagaagacattatacatcagttgtcaaaatctgaagaaa<br>aagaactgagaaaatttaggaaaatagactacagctggatagctgccctttaagc<br>cttggagatggggaggatccttggactttgtgtttttga |
| 225025_at<br>(SEQ. ID. No.<br>52) | Human | /DEF = *Homo sapiens*,<br>clone IMAGE: 3687782,<br>mRNA, partial cds.<br>/PROD = Unknown<br>(protein for<br>IMAGE: 3687782 | gaagccatcggctgagactacacagcttggggccccgaggatgaaggcgtgtaac<br>cactgtgcccccagcgcctgggtgcagcatgccgactacagctggtaccaggngg<br>gcagtgccngctcagggcctgttacagtctaccccctacatgccctggacaccta<br>tttgtgcctctgctggtgggtacaggggtggccctagtcactggtgccactgtcc<br>ttggtaccatcacttgctgcttcatgaagaggcttcgaaaacggtgatcccttac<br>tccccaggtcttgcaggtgtcgactgtcttccggcccagctccaagccctcctct<br>ggttgcctggacaccctctccctctgtccactcttcctttaatttatttgacctc<br>ccactacccagaatgggagacgtgcctccccttccccactccttccctcccaagc<br>ccctccctctggccttctgttcttgatctcttagggatcctatagggaggccatt<br>tcctgtcct |
| 225097_at<br>(SEQ. ID. No.<br>53) | Human | /DB_XREF = 7n04b01.x1<br>/CLONE = IMAGE:<br>3563472 | agggcttgaacctgagtctgcccagctccagaactgagcttgcagccattagcca<br>cagctgtctcctgcatgtctgagcaaagaaaggcctttacacagcatcaccctgt<br>gccatcccatgncaccgtgggactcagctaaaggactgtgcaaagaggggctcc<br>tgagttggatttaggcaaaaggggcagaattcgttttgatttttagagaaaatct<br>ctggagagtttcttttgattcatagaattccttttagatttctttccagcatacc<br>aactagctttagtagtgctacaaccagctcttataagtaagagtgaaaaagtatt<br>cttttcttctttaaaaaataagtttttcttgcttatagttaattctagaaaggca<br>atactaaaggtatatatttttttcaaaatgctatttttactgcacttgataattat<br>cctgacagctctgatctctgtaatagattcactcttcagctctgggcagaaccag<br>aggcagggttcacaccaaatttgtaaataccatatgtgggtctggtgtccaggaa<br>ctttttct |
| 225506_at<br>(SEQ. ID. No.<br>54) | Human | /DB_XREF = ng25h11.s1<br>/CLONE = IMAGE:<br>935877 | taactagttagttatcacctchtcccttaaagtcagtgacctgtgtttgatgtat<br>attacatagagtcttaagtcagtgtacagttccactggaatttgacagttgtctc<br>tacagtcatgcaactcgaagtagaaaagagtgctggacataggaaggggggtgctt<br>ggtttgaggggttaatgtgaggccttttgaaaatgaatattttgataaaagaatt<br>cttgttttagcacagttgatgcacataagtgattctcatatttgttgtataaact<br>ggtttaatacatttggaacatagttggattacattcatttcctgggaaagctagc<br>ttaccatacattcaagtttataaaacaatttnccatangcaaagccatttaaaaa<br>gttcattctgaaaattatttcatttacctacagtgaaataattgtgaactaagta<br>gtctttctgaaaactgttgggttctaggcattcctg |
| 225554_s_at<br>(SEQ. ID. No.<br>55) | Human | /DB_XREF = zl35g07.s1<br>/CLONE = IMAGE:<br>503964 | gtgattgcagcaggggtctctgccccctcgctcccaattcctagtcgtgacttca<br>tttctaaaacagagcctgaccaaccttccatgtatctccatcctcccctgctcca<br>gccagggaggactgagggagtgccccgagacccacgcacatgttggggcttctgg<br>gccaagagtacttttatataactaatttctaaatccaaaagctcaaggaatagac<br>agtgttctgtgacatggattggtttgaaggagttacccaccatcccagcacgata<br>atgtcatctcccaagttggatggcagcacgatctggccctagggagcttcctgtt<br>cccagaagtcattgtcctgggctatccagatgtccctagtaaatcttgcttcctt<br>ctgcaatgttagtaatgccttaagctgacagttgctatttgcagaacagttttcc<br>tctttgcttagctagtaacttgcctctgagcctgggctgatctgagaaacaggtg<br>tgacaagagcatgaaccagaggtgcacctggggcagttccctaataaa |
| 225584_at<br>(SEQ. ID. No.<br>56) | Human | /DB_XREF = qp96b11.x1<br>/CLONE = IMAGE:<br>1930845 | gtgctgaattgtcactcatgggcttgagagtaggagactggagaccaaggtggct<br>agaatccagttgggcctgatgctccctgttgaaagggctccttgtggaatgaata<br>gcacatggctcctgtggtggatctgatagtggcatagcaccaagtgcaggcctgc<br>caaggggccacagacacagaagatgctcccggggtcccccatgtactccagacac<br>actgcaggccacctctcccagcaggttgccagtcatgggccccatcatcatgact<br>tctgtccaaggtactgtgtgcagaatgtgattgagattcaagtcagggcctctct<br>gccctttccctccagaaacaaaaccaagataatttatcctgaacacaggtgaaa<br>aaaggaagggagggaggagaaaaagtccgggtctcacctgggattctctgtctcc<br>tgcaacatgaaggatttagcctgggaggaggtggtgagaactctgggagagaaaa<br>agaaggaaagaatagttttacccatgctgaagtt |

TABLE 3-continued

| Probe Set ID | Organism Common Name | Sequence Description | Target Sequence |
|---|---|---|---|
| 225841_at (SEQ. ID. No. 57) | Human | /DB_XREF = hy16b02.x1 /CLONE = IMAGE: 3197451 | gacattggtggctcaaaggcccctgtcccatgctttggaccagtcttcacagagg<br>ttgagaaggccaagatagagaactctcccacacccttctgtgttggagataaatt<br>tttcgtacctctgcagagactccttgcgtatcccaagttgaaccgcttatgtgct<br>aatgaagagatgatgagatcagtcattgctgactcaattcctctgagcagtgatg<br>gttctgcagtggtggctgacctgcgtaattattttgatgaacagtttgagttttg<br>aaccatgtttatttcctgaaatttcagggtctcagcgatagttgtgctcacttag<br>aatttagtttttttgtgtaatcctaattcaagtaatgtttttaaagtttcactg<br>caaaagtctatgttccaagccattggacagacctgcttgagatatggcc |
| 225947_at (SEQ. ID. No. 58) | Human | /DB_XREF = ot61d03.s1 /CLONE = IMAGE: 1621253 | accttcaccctacagcattacaggctttaatcagattctgctggaaagacacagg<br>ctgatccacgtgacctcttctgccttcactgggctggggtgatccttggtgcctt<br>tgtttccacaaggccttttcctgcccccctgccttgccaaagacatttaatcagca<br>cacagctgccagactattcccacagtgctccaaatgcacatgaacaacagtgacg<br>gctccagccttcgacccagagccccgtgcccagtgcgtcagtgggcctggggttc<br>caggctacatcaagcactgatggtgtcagggctggtagttaccaaatcagggtta<br>agaaacatcagggccacatttcactaccttcacagatcaaactcagcagcagtca<br>tgactgtctgtcactacactggggatcccaattccacataagcacttttggaaga<br>aaacagccaaagttggcctaaaattggcgctggaatttgggctgggaa |
| 226124_at (SEQ. ID. No. 59) | Human | /DB_XREF = nx88c07.s1 /CLONE = IMAGE: 1269324 | ggtgcaccatgattagctcacacacaatgccaaggctgtgcttctattatctgat<br>acatagtttgacaatgggtaattctactcagaccctccctactgattggctagga<br>tgcctgtcaggaactcattatgctactggttgtttggggatccccatagtggact<br>actttcaggaatggcatgaattgtaaccaactgagtgctgcccccactgttacgg<br>aagtttataaaaccttagttccagaagacccaaaggagagtactggtttgtgttt<br>ggtgcttggcctagatccagccaccactctgaaactcancacatcttcattgaca<br>gggagggagcccaggacatatgtgtggctcattgaccagaaggctttcttagtcc<br>caacagccatgaaccatgcacttatggatacccagcctttta |
| 226139_at (SEQ. ID. No. 60) | Human | /DB_XREF = 7e37b01.x1 /CLONE = IMAGE: 3284617 | gcttgcacagaccagcagtcacagaaatcattcttcctgctgtactgggccttaa<br>ctgcctgcaaatgtccagcactactgcataggatgccagagccaccgaaggaaaa<br>cacagccaagtttaataataataaaaggaaaaatctcagcctgcagaactctggt<br>tttgacccaccatcggccagatgcacatcttcagggcctgttgagcaccttctga<br>aaagcagggctcgtaatagactccagcacattccatcagagtcaggaaaactgcg<br>gtgagtcccagagaatctagggtgcagggcagggagcaggagtcataaggagtga<br>taacctaaactgtgtgtagtcagcggggagggtcttatgttatcaggtgaaatga<br>gagccagtaagttagttgatcctgtcacagatataaccctgataacaccccatag<br>atacgcgacacgtgtgtcctgcccctgctttccccatccaacatggttcttctgt<br>tccacagac |
| 226308_at (SEQ. ID. No. 61) | Human | /DB_XREF = zn45g12.s1 /CLONE = IMAGE: 550438 | atgggcagcagctcttagacgccctgcagcatgaactggtgaccactcagcgcct<br>cctgggagaacttgatgcttggtgattcggaagaaaatgtgcaggtgtggactta<br>ctgagcgaactcaaggacgtgacngcgaaaaaggaccttgagctccgaaggagct<br>ttgcccaggtgctggaactctccgcagaggcaagcaaagaggcagccttggcaaa<br>ccaggaagtctgggaagagacccagggcatggcgcccccccagccggtggtatttc<br>aatcaagacagtgcctgcagagaatctgggggagcacccaagaacacgcccctgt<br>ctgaggacgacaacccgggtgcctcgtcagcccccgctcaggccacgttcatcag<br>cccaagcgaagatttttcttcaagcagccaggcagaagtcccgccctctctctct<br>cgttcagggagggacttgtcatgactcatggttacattcaggatacttgagcact<br>ttatatactaccgtagc |
| 226428_at (SEQ. ID. No. 62) | Human | /DB_XREF = wl62h06.x1 /CLONE = IMAGE: 2429531 | tccagttctttgaagcatcctctgctgggtcttggggtgtgtggatggattggct<br>gtctgatgggattggtaacccctcgctactcaagatggggggatacaaacacctt<br>cagggaaggggagcctggttcttctcgttttccttttttttttttttttnnnaaa<br>aaaaaactatttaatttttttaatttattttggttgtttttttgcacaatgaagtt<br>tcagcttctcaaccttctcccctacccagggctgtggacccagactggccttgag<br>ccacagtccctctttccctcctcaccctcttccccctgcgggctcccgggtctgt<br>ccatttgttactgtgctgtgctggggattggcg |
| 226616_s_at (SEQ. ID. No. 63) | Human | /DEF = *Homo sapiens* NADH dehydrogenase (ubiquinone) flavoprotein 3 (10 kD) (NDUFV3), mRNA. /GEN = NDUFV3 /PROD = NADH dehydrogenase (ubiquinone) flavoprotein 3(10kD) | gtgtttgctgcggcaaggacgagccggggcgctgaagactatgctccaggaagcc<br>caggtgtttcgaggacttgcttctacggtttctttgtctgcggaatcagggaaga<br>gtgaaaagggtcagccacagaattccaagaagcaaagtccaccaaaaaagccagc<br>cccagtgcctgctgagccgtttgacaacactacctacaagaacctgcagcatcat<br>gactacagcacgtacaccttcttagacctcaacctcgaactctcaaaattcagga<br>tgcctcagccctcctcaggccgggagtcacctcgacactgagggccctcggtgtg<br>aagatgaaccttccaccgtcttc |
| 226651_at (SEQ. ID. No. 64) | Human | /DB_XREF = wx26b03.x1 /CLONE = IMAGE: 2544749 | ttaatactttcctactgataatgaaatttaaaantggaaantttgtgagtgtttt<br>tcttgtccaatagagcctaattgtttcctttttttagtgatttaacaatctcttga<br>gggctgcacctttaaattcccagattgtcaatagacatgtacagtatatgggata<br>aggtggacacaagtgcacatataaataaaatcttcttaagacttttaactattca<br>tttacagtaggagagtatgtagaaatcatcatccacaagtcataattaggttgtg |

TABLE 3-continued

| Probe Set ID | Organism Common Name | Sequence Description | Target Sequence |
|---|---|---|---|
| | | | tgcctactgtagttttttccatttctgtattatataaacatttgcatattaaaat ttgatttttcccagagacaagtattatatactgtatctatatttaaatcaaactg tggtaatatatttctcagaaaataatgttggggactatagcctgaacatgtggac ttgaagcgacatggaggaggaggttgatcccattgtgtataag |
| 226693_at (SEQ. ID. No. 65) | Human | /DB_XREF = xj03e02.x1 /CLONE = IMAGE: 2656154 | gatgtctttttggcagtgcacagccagagaacaacacatcacacacaagaaaca gttgtgctcatgtgatgggggcctcagcactaggaaggagtggactgttggcgca cgcagcagcttgaataaatctgaaagtcactacgctgcgtaagagaagccaaata aagcgcatgctgtgtacagagggtgtcgagaatgcctcctacgtgacggaaagca gatccgtggttccctgcagactggcaggagcagattccaaaggcacaggaagaag cttgcaggtagaatgtgttcattaccttctgcgcattataccacaa |
| 226749_at (SEQ. ID. No. 66) | Human | /DB XREF = AL582429 /CLONE = CS0DL001YO17 (3 prime) | gaattgattaccagctttacttcccgatcacacaggacagagaacagctgatgtt ccctttccactttgttgaccggctgggaaagcacgacgtgacctgcacagtctca gggggcgggaggtcngcgcaggctggagcaatacgactggcaatggcaaaagcct tgtgcagctttgtcaccgaggacgaggtcgagtggatgagacaagctggactact tactactgatccacgtgtgagggaacggaagaagccaggccaagagggagcccgc agaaagtttacgtggaagaaacgctaagggtttgctcccaggaaaggagaggaag agctatatatatgtgccgacatgtggcagacacacagtaaataatggctgaccag catgagggcagtact |
| 226810_at (SEQ. ID. No. 67) | Human | /DB_XREF = 7a33c06.x1 /CLONE = IMAGE: 3220522 | ggctttaagttgtttcctatgtaaggtaatctttctttttagtattatctaaga aggatggtagattatgtcattttggaaactattgtgtcccttgtattttaaatat ttcaggaaaatgcctacgattgttacaaagatgtgtgttttacttataacataag ctctgattctccagtggccactgggccttctctgtgctctgtattcaactgcagt atgaattacagaatgctgtgcatgttcgttagtaccaataccatgtgtatgtggt agaagttgtaaccagtttctggatctgtatggtactataaaatacttattttata attctgtaaccgtatggcagtgttatgccaaaaatgtataaagagcaatagtttt tgttgcttactgctgtattttaaaatattgtttctaaaataatagagttagagtt ccttttgagtaattatttttaagaactattgccaaatatacatcctgtaaaacta ataaaagccactccatcttagataaca |
| 226839_at (SEQ. ID. No. 68) | Human | /DB_XREF = yx78b03.s1 /CLONE = IMAGE: 267821 | tttttggccgtgtggtcatctaccacctgcgggtgcttggggagaaggtgtgag acctctaggggctgtctcctccaggaagccctccgggaagcacagcaaagtccct cattctgcacagaaggtttattggttcctcttgggaagggtcccctcccaccacc tgtccagaagctgcctttgaagtcagttctgggtttccccagctctggctgacca ttttgttccctgagtgtctgagtccccggcaggcggccttcactcagggtcagcg ggcaccaggttgctctggaagagcttgaggatgtggttctcgatcacctgttgca ctgagatggggcagggaaaaggtgggctgtgagcttgaatcgggagtggggtgga ggcacaggccaacctgcgctctnccccttaggggacaaacagggacccttgcagag acctgcattacagagcaaagctgggagaaccgaggactcaccc |
| 226917_s_at (SEQ. ID. No. 69) | Human | /DB_XREF = no87g06.s1 /CLONE = IMAGE: 1113850 | ggaagaagtgttgtcggagtcagaggcagagaaccaacaagctggtgctgccgct ttagctccagagatagtcattaaagtggaaaaacttgaccctgagctagactcct aatctagcttgccattattgtgtgtgtaattatggccaaaaggacataggagatg gactaagatgtcttggaccacctttgtgt |
| 227181_at (SEQ. ID. No. 70) | Human | /DB_XREF = qr33c07.x1 /CLONE = IMAGE: 1942668 | atggagaagcacacatggctcccctgtttgaaaaagggcctgaataatactctgc ttctgcctcatgacatcagatgctactgttttggtttttttctttgagccccaat tcaccatttcaggatgtggatgggggcggggttgggggtaaaaacagctataaaa agcaactgcagatgctgactgactgcagtgggcagggtatgtagctgctccaaga tgacttgcatcataccccaattactgctggcatcttagttgagagtataatctgc ttggttgccttttttatgggaataaagagaataaaaggtattttaatagaataaag aaaaatttgaaaatataatggaaggtatttaaagagccacccacatagcttcacc aacccttctcacacatcaactcataaat |
| 227412_at (SEQ. ID. No. 71) | Human | /DB_XREF = zq40h02.s1 /CLONE = IMAGE: 632211 | agaaagaggtctctacacaagcccgtgattcttcatggcaagggataacatcaga aatgtttcattttctgctattagtttccattcctttccccatccaggcataaaga gaaacaaaagacaatgatggtattctctgtgtcctcagctttggcacttttgttg atgttgctaaggagcagtgaccttgctaaaaagactgaataatccacccactgaa tagctaacctggggaggaaatgaaaatttcctttgtggatctccccaaatccatt gttgtcaccaggccctcccagaacctcctcagttccttcacagtgcaaccctgtg tacttggcccgcaacccaatagtat |
| 227427_at (SEQ. ID. No. 72) | Human | /DB_XREF = wd34g06.x1 /CLONE = IMAGE: 2330074 | ctgctgctgtcacccaaaggggaggtggccagagccctcttgccactggataaac aggcccttggtgacatcccccaggctccccatgactctcctccagtctctccaac tccaaaaacccctccctgccaagccagacttgccaagctggatgaagatgagctg taactggtgaaaaccatgggggtggtgctgactcagccgcctattccccaaggag cttcagggcagtccttctggcactggctccagaattcctccttcttggtgtgtctg gagggtgggcaaggctgggagggatatcaacttggaggagaacacctagacccaa ggactttttttctgcccaaggaacacagtttccttcagctcccatccctatgcatg catcatggtcccccaaaaggaggatatgtgggtgggtgggagggctggggcagg ggccagatagaaattatt |

TABLE 3-continued

| Probe Set ID | Organism Common Name | Sequence Description | Target Sequence |
|---|---|---|---|
| 227472_at (SEQ. ID. No. 73) | Human | /DEF = *Homo sapiens* mRNA for KIAA1623 protein, partial cds.<br>/GEN = KIAA1623<br>/PROD = KIAA162 3 protein | gctccccagacgatgttccaggaggcgggtgtgccagaaggggccacgtcttgca<br>aaccaccgcgctgtcctctttgagaaggagtcttactcaggactggggcctgtgc<br>acacattgtcgcctcttttcagcacttagagattccttcctttgtctagtngctg<br>aagccagggctgaagttggcctccaaatctgggccgtctcagagngcngcgcagc<br>ctggagttttccatctgtggccaagacccagtttttgggaggaggccctcatggg<br>tcaagccagcctgtaccaggatggggggagggggttcccaacntangccccagcc<br>acccagactcccccacccccactcccttttccactgctctgacctcgggcactgt<br>tgaaatatagtttttattgcatttctgccgttttacaaaa |
| 227603_at (SEQ. ID. No. 74) | Human | /DB_XREF = zb80d11.s1<br>/CLONE = IMAGE: 309909 | gcaccacccagcttgggtatctggtgaattctgtggtctgcatgtccatgttttt<br>gacattctgggaagggtgngcccaggctgtgatttgccatctactgctgcaggct<br>atggatggtattcagaagggaggggagatgctgtgtgcgtgttctgaagggtttc<br>ccactaaatggagagactgactctctccataagtatttgattttttactttatctc<br>ctcgttgacttcacagtgtaagtgcagtttgtctctactgggtgatgcatgcaga<br>taaatgtttatgtgaacataagaagtctgcatgtgtgggtgaactctccacatca<br>tgtcatttattgtccatcattacgtatctgtggtgtctagcacattcctctacct<br>tattttctgtcattgtacctacttctacctgaacacgtatt |
| 227810_at (SEQ. ID. No. 75) | Human | /DB_XREF = xd99f12.x1<br>/CLONE = IMAGE: 2605775 | ggtattctgcagtgactatgggaaagccttgaatgttctatcggtttttaaggga<br>cttgagaattaattctggagagaatgccccattgaacatcatcaatattggagag<br>ctttctgtttttctacatttgttaggaaacttgtgagcattcacactacagagaa<br>acttgaaatataaagaagaagagaaagccttcagtgatgcctctgtgttagggaa<br>aatatggaacttctccctggatgcaaaacctatgagtatattaatattggaaaat<br>ttttcagtgattcttctctttcttgtatatgagagaacttanatggagaaacccc<br>taggaatgtaatcagtgttaggatgcctcagcctgaactcttcactgagtggcca<br>caattttcactgggaacaaaaagtataatcactgttttgagtgtgggatatcctt<br>tatcagtgtctcatctgtagattggactgctggctcattaattttttagtcttt<br>ttttcttttaatataaacatttgtgtatagctgttccctaa |
| 227921_at (SEQ. ID. No. 76) | Human | /DB_XREF = we90c08.x1<br>/CLONE = IMAGE: 2348366 | agctttccttttttgactgtcttattttacttaacagaatgttttgaanatttgtc<br>cttattgtagtacttttcaagatttccttatttttaaggctgaatgctatcccag<br>tgattgtacgtgccctgtttgctgaatctactcatccttaagggtacatttgctt<br>ccaggtaacatgtttgtgagtaatactacaatgtgcatatatctattccatgttc<br>tgctttgtctgtttgggatatttttcatacactgattcagtaccatgtgtattcc<br>cttgcttttgttgtctcatccgttgatgntacgtcccccaaattattgccacgac<br>cagttgtnatgaagcttcacccttctgtattgtgctaggaattttacagctatag<br>gttttacattatagtcttcattcatttttta |
| 228286_at (SEQ. ID. No. 77) | Human | /DEF = *Homo sapiens* cDNA: FLJ21836 fis, clone HEP01654. | gaaatgggcaaaatagctcaacaggnttttntgcaaagaagaaatacaaatgncc<br>aagangcacatttaaaaatttncagnnctattnactcatcaggaaaatgcaaatc<br>aaaaccncaagacacccaatgtctacaatcaaaaagataatanctagtattgatg<br>aggatgtggagaaattgaaattctcataacatgctggtaggaatgtaaaatgggg<br>cagccactttggaaaaagtctggtagttcttcaaatggttaaatgtagagttacg<br>atatgatccagcaattcctctcccaggtatatacccaagataaatgaaaacttat<br>atccacataaaaacctgtgcacaaatgtccatagcagcgttattcataatagcct<br>aaaagtggaaacaatcccagttccagaatgaggaaggggagaaactaatgtgtat<br>tagctattgtgtgctaagcattcaactagattatttacaaaccttgtatcatctc<br>aactctttaaagactgtattgcaatgttttgaa |
| 228650_at (SEQ. ID. No. 78) | Human | /DB_XREF = wf38b04.x1<br>/CLONE = IMAGE: 2357839 | agggcattaatccccttcatgagggatattctctcatgacttaatcacctgccaa<br>agaccccacctcttaatactacatcagtgatgggttcaatgtatcaattgggtgg<br>gagggggcacattcagaccatagcatctagtcattctggttttattaagatttat<br>tagacctgaggcatgaaaaatagcatactggatgggacttcagcatcgatgagtt<br>gccttagtaatactgtt |
| 228736_at (SEQ. ID. No. 79) | Human | /DB_XREF = xa46a03.x1<br>/CLONE = IMAGE: 2569804 | ataccttgctcaaagagaccaacatttggactgtatctgaaaaantnaanangcc<br>ncgaggnatanatncaaantnttctcacnggaacngccncattcncatrtttgng<br>ntgnnacatttctgnnaggagcttgaggagttttgggtttacagagccctttttgg<br>tagaacttaccaagaagctgacttactgtgtaaaggcagaattaatccctctcat<br>ggaagttactggagttttagagggtcgagcaaaacagttatacagtgcaggttac<br>aaaagtctaatgcacttagctaatgcaaatcctgaagtgctcgtaaggacaattg<br>atcatttatcaagacgccaagccaagcaaattgtttcatcagcaaagatgctgtt<br>gcatgaaaaagcagaagccctgcaagaagaggtagaagagttactaagattgcct<br>tctgatttccct |
| 228930_at (SEQ. ID. No. 80) | Human | /DB_XREF = tu75d08.x1<br>/CLONE = IMAGE: 2256879 | gacttgtaagggtgccttaaatcctgaantactngtactnctngtattnactaaa<br>cccnatgttagtttnacgccnaagattcntgtggtggtttnacatattctttttc<br>ccctttgttaaggtggggaggccacagcttatgtgaatgactttctcaggagtta<br>taaagtgatacaggtaaagctaagaaaagaacagatttgataacttttgtttta<br>actgtccagtgttagggattgtggctacagtggtctaatttttaaaaactctttt<br>ttttgctttgtttttttaacagacttatcagcaggttgcaggtgaacatggccttg<br>aggtaaatctgtcccttgctgaatacagtttcagtagattgtttatagtagtttc<br>aggaattgagatttttttacaaaaatacaaaagttttgcttggttctgttctagat<br>gttttcttctaaataaatgagaaagatgtttcaacaaaggctctttatgctgaat<br>aattgtgatgcttgaagttgctaatctgctt |

TABLE 3-continued

| Probe Set ID | Organism Common Name | Sequence Description | Target Sequence |
|---|---|---|---|
| 229001_at (SEQ. ID. No. 81) | Human | /DB_XREF = 601115521F1 /CLONE = IMAGE: 3356236 | gtctccgaagaggaagtccctgactagctatataactttgggcgagttacctctc<br>acttctttgtgccccagtgttctccttgggaaactggatttaggttagatgacct<br>tttaaggctccttgtatgatattttgtgatctgtacatggcagagtatagattag<br>gagccaaattttccaacctagtgctatggttcagaatacatagcaccccaagcgt<br>ctggctggagccgaggatgggtcctccagtattggcacagatgttccggagccca<br>ggaagcatcccataaccaaccttcagccccaccgccacccccagcgtattccaga<br>gccgcttccaaaccacagcctatccctctgctccatttcactcttgccctcacaga<br>ctttcagcctccatgctctgagacaactgtgggtaggtacatctctgttggtgga |
| 229035_s_at (SEQ. ID. No. 82) | Human | /DB XREF = we88c03.x1 /CLONE = IMAGE: 2348164 | ctgccctcgctgctggaaggcaaggggccgttctcgccttggttttctaggttgt<br>gttgcggcaggagctgactgcccctaggcctagatctctgcacaacttcgctcag<br>ggacacctgcctctgtgcatgtctcatggtgtgaatgtgtttcctgctcacaggt<br>accgttttgtgtcatgcagttactggaatgtacaaaagcagctgtgatctttgtg<br>agagctgcacagagcaggagtctgagagctgcacagagcaggagtctttatttgg<br>ttcacttctggtctgcagcaaccacttgctactaaaagatggaaaagatgtacaa<br>aaatgtcacagccctttagaaagngacattatcagaaatgtatgaccttcagtcc<br>tccctccctctcctatgcccccaccagaccaggcggcgagaagga |
| 229384_at (SEQ. ID. No. 83) | Human | /DB_XREF = ho39h11.x1 /CLONE = IMAGE: 3039813 | cacagtgagttgcaggttcaccccagcgtcagtggcgggcgggaagtggggatga<br>cacaaggacctgagtgtccaaggggggcttcatggagccctcatgtgaagtcccca<br>gcatggaccctgacacatcgtaggtcctcaacaaatgtcactccctgttgtcact<br>ctgtttagtactaagaataatgatataaaactgggacagtaaggaaaacacaaac<br>tgttgggacctatatctgaatctattagtctgcctaatagaaaagccaccatcag<br>gattttggagattacaagctcactttagattagccatactggagtcagccctgga<br>ggctcccagagatcagaacaatcccagcgcttgacaggatggctgggaaacaata<br>catatgaatgccggaaaatgcagaactaatctaggaaaaagtgtaagaagaaaat<br>aaacatcatctgtcattctatctatcagagataactgctgtcaatattttggttt<br>ccttccaatattttttctattcactctgtgcat |
| 229421_s_at (SEQ. ID. No. 84) | Human | /DB_XREF = nab38b03.x1 /CLONE = IMAGE: 3268156 | cctagctcctcaagtgtgctttttttaatatatagttgatatattattgaaggtac<br>tacaaaatagaaatctctggagtgcagaagttaagaaaataaccttcatactgaa<br>aatatatccttaaaaaaacaacaacaaaaacctctatacaaatgtagtacagcat<br>acaaatttttaaaagatggaatgaaggcacgaaccattgcaagtcttttggaaat<br>gtatgaacgtaggcatgctaagttgaaaatagtcttaaaaaactagtgaaaactt<br>catgtatataaaataattcagaaataaatctgctaacattcttcactttcaggtt<br>gcatgtgtgaatccaacatgttccttcttcataaatagtcaagcgttccttcagt<br>ggtgtttgtgtggtctgtcttcgtgctggtcaccagcctcagtatgtctggtaga<br>cgtcggggatggggacctgaatggcagcag |
| 229534_at (SEQ. ID. No. 85) | Human | /DB_XREF = zk70e10.s1 /CLONE = IMAGE: 488202 | taagcacagtagcattccaccattgggctatgacctgaggagaatcaangtagcn<br>ttntnaggcctngtggacatcgtggatatnaaggaatgctctcgtaggagggtac<br>aagaaccccancatgattccaatagagaaggcccaggggcccatcctgctcattg<br>ttggtcaggatgaccataactggagaagtgagttgtatgcccaaacagtctctga<br>acggttacaggcccatggaaaggaaaaaccccagatcatctgttaccctgggact<br>gggcattacatcgagcctccttacttccccctgtgcccagcttcccttcacagat<br>tactgaacaaacatgttatatggggtggggagcccagggctcattctaaggccca<br>ggaagatgcctggaagcaaattctagccttcttctgcaaacacctgggaggtacc<br>cagaaaacagctgtccctaaattgtaatgcatttgtctgttgttgacatgagaga<br>ttcaagatcagattctagtgttcagtaaccctatg |
| 229570_at (SEQ. ID. No. 86) | Human | /DB_XREF = hv48b07.x1 (CLONE = IMAGE: 3176629 | gcctcgggagccccgaatagcagctgggagaaggggcgaggactngagcctcnnn<br>nnccnctgccggccgggctagagatacgggcgtgcccccccattgtgcgcctcccg<br>cccntccggtcccctcaccctgcggccacntggggcgtggggcggtgctcctgcc<br>cgtgcacgtagccgctgcgagcggaggcctgctcacctggtgcctgctactcact<br>cccccgggccggtgggcgaaggacacccgcaggaactcggcagaggagaaattca<br>gacggctcccgagggtaggaaaagaccccggcccaccgtggaatctgaaacaccc<br>gaccactctgccatcccatgtttcaccagtcagaccccccagggcagggcaggggga<br>agcagaatgcaaactggggcaccgtttccctgaagcgtgttggccgcgtttgtcg<br>tagtgctagaggtgcatacccttggac |
| 230048_at (SEQ. ID. No. 87) | Human | /DB_XREF = 7j53a06.x1 /CLONE = IMAGE: 3390130 | tagtgcaagcaacatgccatttcaaatccgtagacttgtttctttgatactcttg<br>ctgtaggtcgccgtgaggggtagggaagcatatatactgtagggagaagtatcaa<br>aatcatttaaggtctttttttccaaactagtgttcccctcccacatcccaataact<br>cttggaagtctggtgctccctctaggtgaaaatcatttgctggcttatggagtca<br>ctgttgctgagtcccatcccccagttacagtgcagtggaaaacaggtttagaatc<br>tagaacttgtttgtatgttgtcacttggttatgttccaagtaggttagaaccatg<br>gaaaagagattgcaaatggtagtttcttctag |
| 230791_at (SEQ. ID. No. 88) | Human | /DB_XREF = AU146924 /CLONE = HEMBB1001899 | gtggttgtatgtgtctgatggcttatgtaaacatagaagaagtcttcagatggct<br>aaaataaacatgcgcgtgttaccaaaggatatgtttacacaaaccatttgctcag<br>cctctgaaataatgaataaatgaagattttactaaaataattgggaggatttttg<br>tgtttctgcggatgccataattgaatggcaccaaagagacttttatcagctattt |

TABLE 3-continued

| Probe Set ID | Organism Common Name | Sequence Description | Target Sequence |
|---|---|---|---|
| | | | tccgtgttacatgtgttagcagttcctttctgtgggttgaatacttcattctgta<br>gttactttacacatgtttttctaagaaattgtcgtttattactgcaattctagag<br>agttgcttgatttctcaagagaaatttagcagccagtaaaggttatttggatctg<br>gttggtcag |
| 230922_x_at (SEQ. ID. No. 89) | Human | /DB_XREF = ym01a03.s1 /CLONE = IMAGE: 46241 | gttctcatgagatctggcacttcacccctcactctctcttgctcctgctttggcc<br>atgtggagtgctcactccccttttgccttctgccatggctgtaagtttcntgagg<br>cgtccccagaagncccatcagataccagtgccatgcttcctgtacagcccatgga<br>actgtgagccaactaaacctcttttatttataaattaccgagtctcaggcacttt<br>ttatagcaatgcaacaatggactaatacatatactttagcataaaaacatttaaa<br>agagtctgaaactggagtagttaactcagtaaaaataacttggcaataaaacaca<br>gaaaaacaatctatttgatcatgtagtgattcctaatgtaaatcctagtacaact<br>gtcaactgat |
| 230983_at (SEQ. ID. No. 90) | Human | /DB_XREF = 7e87b12.x1 /CLONE = IMAGE: 3292127 | cttgctgtgagccttttgggtttgtttcctagctccaaatcttaacttggtgtca<br>agtttcctggctuggagacaagcttttaccgacttcctctgcttgccagcaaagt<br>catctgctaactggatattggcagcttctctgctgtcttgcagctgcttccggag<br>tgggttccacagggattcccgtgtgttcttggttcagcttgcagagggactttca<br>cactccctggagaccgtttcctcccattctgtctggagttttcggcctaccccaa<br>gacaatgagatattcctgacctttccacctatttccctccaaccccaccttccga<br>aatacatttgct |
| 231271_x_at (SEQ. ID. No. 91) | Human | /DB_XREF = oz47c03.x1 /CLONE = IMAGE: 1678468 | gtcagggaccgagacaatagtggctntgggtgtagcaggtcgggagaccccagcc<br>catccggcctccctgccccgccacctccccggggcantggaggacgccggccacga<br>caggctcctctgcttccagatgactcctgaggactacgaaaagcttggctttccc<br>ggtgcccgggacctggccaacatgttccgtttntatgccctgagacccgaccgtg<br>acatcgagctgaccctgagactcaaccccaaggccctgacgctggaccagtggct<br>ggaacagcacaaaggggacttcaacctgctgtgacctgcccgcctcgcggcccct<br>tgtggggatcgggggcaccagaggggcagaggcaccaacatctgaataaagccat<br>t |
| 232524_x_at (SEQ. ID. No. 92) | Human | IDEF = *Homo sapiens* cDNA FLJ11019 fis, clone PLACE1003611. | atctacattatcttcttttactattctagaagattcactttataaaatgtgcat<br>cttaaggagacatactgatatttctcaatctgtgagtaatggactaattgctatt<br>aaatttgggagctttacatatgccacaacagaaaaagtcagaagaagcatctaca<br>gttgtttagatgcacagttttatgatgatgaaactgtaacagtagttcttaaaga<br>cactgtaggacgtgaaggaagagatagactcttggtccagctgcctttgtcttta<br>gtatataacagtgaagattctgcagaatatcagttcactgggacttattctacaa<br>ggctagatgaacagtgtagtgctattcccacccgtaccatgcatttcgagaagca<br>ctggagattactggaaagtatgaaagcacagtatgttgctgggaatggttttcga<br>aaagtgtcctgtgtgttaagctcaaatcttcgtcatgtgagagtatttgaaatgg<br>acatagatgatgaatgggagctcgatgagtcttcag |
| 232527_at (SEQ. ID. No. 93) | Human | /DB_XREF = AU146179 /CLONE = HEMBA1007062 | gagttgatggtgttgctgggttataancagcttcaaagagaaggcattttgaatg<br>aaggtggaaacataatggccaggagaacaagcaaaggactaggaancagtgaact<br>tcatcttggcctcaagttcctgaggtgcatatgaataaacagtctctaacccaga<br>gggtttcaagaaaagcagagtcctcaaaatccaaaggtagagtttccccacattg<br>atattatactaattacacgtataacagtactttggaaaagcacaggtctctggtc<br>acctctaaaaggcaaggttggtaaggaggtcagggtgtcacctgttggtagtctt<br>aactaaatggtctcttcaagggatctaaggatggaaaggggatatataatggttg<br>gattaaaggctcatcattgattagcaaattgtccctttttgtttctt |
| 233214_at (SEQ. ID. No. 94) | Human | /DEF = *Homo sapiens* cDNA FLJ11900 fis, clone HEMBA1007341. | aaaccagcctttggagagggcctcatggcaagaaactaagggtggcctctagcca<br>gtagtcagcaagaaaacagatccttgttctagtagtgtgccaggaactgaagatt<br>gccaacaaccttgttatttggaagtgaatcctggttcagtggagccctagctga<br>gaccttagctctggctaacaccttgattgcagtcttttgagaccaggaaacagaa<br>agaagccagctaatctgtgcttggactcctgacccacagaacctgtgagataata<br>aatgtgtcttgttcttaacacaccagatttgtggtaatattgttacacagtgtag<br>aaaactaacaaactaggcctcaaaataaatctataaacagttttgcaggtacact<br>gtagaacacacaataaaaagtagccacagaaagagacatgagtgaataccagcag<br>gagcttctattta |
| 233302_at (SEQ. ID. No. 95) | Human | /DB_XREF = AU146285 /CLONE = HEMBB1000025 | tgtgtgtctaagcaattctggcccctggctcccaccaccctaccctctccacaaa<br>ataatagacattaggggaggtaagggancagaagaggtctcttngcagatattat<br>atttttaaaaantggttctatgntaataagcagcagctaaggagacagaaagnca<br>gtagatgaagagagtgccaatatcttccatggggaaaaatgaatgaactgaaaga<br>gaatattatttttctagaatacagaaagctgtcctctcacagatcagctggaatt<br>ccaaggtggattatggacttcttctaactcccattgatagtgcttcttaccaggt<br>gaagggaagggctactttttcctaaaggagaaaaaagctttcagacaaagctcgt<br>accaacccctgaactgcaaatttgctcaagtgaccgtgcatacttatattcctaa<br>tttaaatgattatttatgtcaaacgctcattgtgaaactt |
| 233429_at (SEQ. ID. No. 96) | Human | /DB_XREF = qm62e07.x1 /CLONE = IMAGE: 1893348 | ttgggcaccacttccatcaggaaaacagtgtgcaagatggagaaactaaggacaa<br>accccagagaaactggacaaacccagcagaagaaaggaagaactgcaactcagaa<br>atcacataaccaccaagcaggtntggaccacacatgctaaatgtgcatccactat<br>ggcgagtcccaggcctttaacagcagggactaaggagggcagaggctgacaccaa<br>ccccctttcatactgtagcactacatccctctcagataccagtttaacacgaagt |

TABLE 3-continued

| Probe Set ID | Organism Common Name | Sequence Description | Target Sequence |
|---|---|---|---|
| | | | ctccctgtttgactcctgtgagttgtgtattgaactanaaagtgnttnctgagtt naaaataaaagcgcnntnncnnnnnnanaannnanattgtgtatcttgacttctc aatgatagcaagttacattttgcagttttcttcctatacccacaaatgaaactat tcagacttaaatatcttcctgtgtgcctaaacgtt |
| 233440_at (SEQ. ID. No. 97) | Human | /DB_XREF = DKFZp761l07121_s1 /CLONE = DKFZp761l07121 | taagaaatgtcgaaggaggccgggcgcggtggttcatgcctgtaatcccagcact ttgggaggccgaggcgggcggatcacgaggtcaggagatcgagaccatcctggct aacacggagaaaccccgtctctactaaaaatacaaaaaattagccgggcgtgtgg cgggcacctgtagtcccagctacttgggaggctgaggcaggagaatggcgtgaac ccgggaggcggagcttgcagtgngccangatcgcgccactgcaccccagcctggg agacagagcgagactccgtctcaaaaaaaaaaaaaannngacaaaggaaattctt ctagttcctttaaggatttctctagcacaggatcagagaggatcttggttattgg tgactggtgagattctgttgggtgtttggaagcttcaaatgcatggagccacccc ttaaaaatgtctcactggaggcaggcacggtggcttatgcctgtaatccmgcatt ttaggaggccgangcaggtggatggcttgagtatatatacttcgcgagcaccgtg g |
| 233493_at (SEQ. ID. No. 98) | Human | /DEF = *Homo sapiens* PAC clone RP5-988G15 from 7q33-q35 | atgagaacatggtcttggccggagcaatttctgggctggtgggacccttgtccac aattgtagtttcatatatgtgcatcctctgtgctatccttcagatccaatcaagg gaagttcagaggaaagccttccgcacctgcttctcccacctctgtgtgattggac tcgtttatggcacagccattatcatgtatgttggacccagatatgggaaccccaa ggagcagaagaaatatctcctgctgtttcacagcctctttaatcccatgctcaat ccccttatctgtagtcttag |
| 233599_at (SEQ. ID. No. 99) | Human | /DEF = *Homo sapiens* cDNA: FLJ21498 fis, clone COL05627. | ctgtgttgttttgctggtggccacgaatccgaaaggcccatgctgcagcgtgccc ntgctttgagtttggttgatatgcnttaaataagaacattagttttcntgggagaa tttggtagcacccgttcttcccttcactgtgtggggggaaatagtgttgattgaaa ggaagaggactccgagattggattggagcaagaaagtgtgggtatcgtgtgttgt gactgtgtcttctccggggtgctgcttcactggaggtctccnttcagggtctggc cctcatgcctggccccaggtgctcgtgtgcacgtgagcggctcttcctgctgact gactacagctaatt |
| 234735_s_at (SEQ. ID. No. 100) | Human | /DEF = *Homo sapiens* clone PP1490 unknown mRNA. /PROD = unknown | caaagattccctcgaatcctcgtgctccatctgaatcgattttctgcctcccgag gctccatcaaaaaaagttcagtaggtgtagactttccactgcagcgactgagcct aggggactttgccagtgacaaagccggcagcgtccactatggccactacacagcc ctgtgccggtgccagactggttggcatgtctacaatgactctcgtgtctcccctg tcagtgaaaaccaggtggcatccagcgagggttacgtgctgttctaccaactgat gcaggagccaccccggtgcctgtgacacctctaagctctggcacctgtgaagccc tttaaacacccttaagccccaggctccccgtttacctcagagacgtctatt |
| 235363_at (SEQ. ID. No. 101) | Human | /DB_XREF = 7l45h09.x1 /CLONE = IMAGE: 3524585 | cccgaagagcacccagcatatagctctcatttgttgattctgttagatcatgatc aatgttaagcctaaaaacaaggtggccacatcagtggtttgtaacccatgtttat tctaatcagtcaatctggggctatatataatagtagttgaatgtttatagtacta cccttnggaaaattcccatatattcncncccagcatggatataaatacnggaaag atttcccattgagtacttctctttagcactccagntaacactagacaaataagca cctaaatgccgagtgtttgtcagttttaaaattagaaaagaaggcaagttgtttt cttgtctacctgtttaataaatttttttattgnccaagtanntatgttcatttgat ttaatacgttgaaatgtagtttaaaatatatattcaaataactaacaa |
| 235467_s_at (SEQ. ID. No. 102) | Human | /DB_XREF = 602272817F1 /CLONE = IMAGE: 4360612 | cctctcttaaagcggcaccaacgtgagagagacaggcagacagacagaaagccag aggcttagggaaactctggaacccagacaagaatcttacgctgggaaagactcag atatccttgtttgcacaggactggtggaaaatctcccatgcgaccctcggggccc agagccatctgggtctgatgttctgttccattgtacatcgaagagatatatatgc acatatagtatctatattcatacatattatactcttgtgtgtagtgca |
| 235634_at (SEQ. ID. No. 103) | Human | /DB_XREF = 7a17e03.x1 /CLONE = IMAGE: 3219004 | tcatcaagcctttcgttttcaaaccaccatttgtcagccttgaggtagagagaca tatagatttgaaaatactttcttaagagatcatgtaactatataactctgaattt aaaaattgaggggggagggataatttcaacccactgcctcttaccagaaacattt ttttaaatctgtaactgctttagtgttaacagggtgcaaggtggtttttgtcccg tattgttcttaaaaggactcatttattgtgattgtattgtactgtatgagaacaa antcataaattgccttgtattgtttataatagaccataccacgtactacttcagt attatgttccaagtattcagtgatgcatgttaacagttaggtcctaaaattctgt ggtgctaattctcccatacccaatggtgcttttgtggatgctaactgcacacatg ctgaac |
| 236312_at (SEQ. ID. No. 104) | Human | /DB_XREF = oc10d11.s1 /CLONE = IMAGE: 1340469 | cctatccctggccaaggaagtatgcaaattgtattgtggtttttgaagtttaggt gatctcttccttctatccctagccaaggaagttcatcctgactccccaacaagca tatcaaaaggagtgtttcgtcaccttttttcctcttaccctttacatccttttagc aataaagtgttcagaacaaactggttttcctttactgtgctttgcaaaacttatt catgttttattgggtgactttgtatttacactttcctcagatagtctgttgtcag atgactttgaccaatgattgggaggaaccaaatacagaggattttatcctatgcc taatctatattgtctacagagtaaatcaggtntgaatttgtgaacagtaatgaaa caattttccaactaatcagaagaattgtttgttaagtaaccttaattactcagtt tttggtgaattgtttgcggcttaacttg |

TABLE 3-continued

| Probe Set ID | Organism Common Name | Sequence Description | Target Sequence |
|---|---|---|---|
| 236875_at (SEQ. ID. No. 105) | Human | /DB_XREF = wb57e03.x1 /CLONE = IMAGE: 2384860 | gaaggagagctgttctgcatccataaaaaccagttaaaagggatttcataaggtc tgaaattgagaactttcccaagaatactgcatcttgttctcttgtgcaatataca gacgtgtgaatattcctaacagtaaccaaatgggtgcactctctgtgaaaacgca tctttcaaagagtttttaaacaaaggagactcctgggcctttagaaataattgc cacaaactgcaaaaacaatctccaacctcccacttctgtaattctcatctgttgt cttactagaaaatttatttctctggtaataatgttataattgatatccctgtctt ctcaagatgtaaaatacttgtaaaaacttctctgtccatcagaaaat |
| 237023_at (SEQ. ID. No. 106) | Human | /DB_XREF = 7q84f05.x1 /CLONE = IMAGE: 3704985 | tagaaagataattccgtctctcctttggcagtaggcatgtccctgtgagggagga gatcagcaggatttttccaagcacctgtcaaaaccctgntgatcaaaacagaaca tancaataacaaagaatggccaaaaccagctcggaataggaattaaaatgcattt gcataagatactcccaccagggccatgacagtttacaaatgatcccacggcaata acccaggaattatcttatatggttccaggaacttcctgttcctagtttatgaata acctgcctcttatttagcatataattagcagtggbtataaatatagctagccagc aatcctggagtgctattctacctgtggggtagccctgctctgtctgtggagcagc cattttgctgtac |
| 239496_at (SEQ. ID. No. 107) | Human | /DB_XREF = xy02b11.x1 /CLONE = IMAGE: 2851965 | gtagagatgggctgtcttgccttagagacattaaggtctgttataaagctataat aacgaagacagcctggtattagggtgccagtgtagttacagacaaagagaccaat ggaacaggataaaaagcccataaataatctcatgcatatatgcacacttgactta caatggaaggagtattgcagatcagtggggagagactgaactaatcaataaatca tgcagttacaagatcatacatgtggagaaacaaaatgaaaccagatcctgaagta cacaaaaaatcggttccaggtatattgaatat |
| 240130_at (SEQ. ID. No. 108) | Human | /DB_XREF = yd76e12.s1 /CLONE = IMAGE: 114190 | attacttgaccaattttcatagcaaactgattggnttcacttatccccccactga actgttaagacctggcgagatcctttttatagttctttaaacttccaggactttc tgcttatcttcaggaaggacagtggaccttcaggggagaggagaaggaggaaatt tgcatatttaaaatgtgtgatctgagccaaacgctcttcagctaacttgatctcg catcattttcccagcttcctttgagaattcagaatcaaaattcaggcatcaccat ctagtgaccacagggtcctgcaccccagcccaaacctggggganccccttagggata atgccctttctcatttgtcttt |
| 241395_at (SEQ. ID. No. 109) | Human | /DB_XREF = AL572553 /CLONE = CSODI008YD03 (3 prime) | attctgactgtatcactgaaaggctgtgtagctgtgtgaccgtaagcaagtcact taactccagattctcagtgctgtcatctataaacagggatgaatgaatatacacc tcagagttgttaagaatccaatgagaaaatcacgggtaacccttatataaatggt tgtgaaacatttcaaagatacaagcatccttggcctttgcagcccagaatcatcc ctccacattttcctacaatccaaccacatcaagaaatgataactgctcagaaag tttatcaatatttaccaaaactcatggatttaaaataaacattaagtttctncaa taaaaaannnnnnaattctatgccatttgtactcccttgatcttcaccctatttg gcaatatcaacttttttttttgagatggagtctcactttgtcacccaggctgca ttgcacgtggtgcaa |
| 242171_at (SEQ. ID. No. 110) | Human | /DB_XREF = zi55d08.s1 /CLONE = IMAGE: 434703 | gtcattgctggtcaatgaagcatactaacagaccaatctgagcagtaattgtcct tgcataagcaagattttttttttttttgatggtaatgagtgatttcaaaaatacg tttaggctgggtatggtggttcttgcctgtaatcccagcaactttgggaggccaa ggtaggaggatcactcgaggccaggagttcatgaccgtcctggtcaacagagtaa gacctcgtctctgcaaaacaaaataaaataaaataaaataaaaaaacttaaaaaat catgcacctatagtcccaactgctcaagaagctgaggtgagattgcttgaggcca ggagttagaggctgcagtgtgtgattgcccactgcattc |
| 242602_x_at (SEQ. ID. No. 111) | Human | /DB_XREF = wz04g07.x1 /CLONE = IMAGE: 2557116 | ttcttgacccattacaatctcttctacgggcaaagctgagggactgttgacattt agggatgtggccatagaattctctctggaggagtggcaacacctggacattgcac agcagaatttatatagaaatgtgatgttagagaactacagaaacctggccttcct gggtattgctgtctctaagccagacctgatcacctgtctggaacaagggaaagag ccctggaatatgaagcgacatgagatggtggatgaacccccnggattggatttt cattactgtgaagaaaaacactggaattttgataaggagttctttaaatctacag gtcactttggataat |
| 242606_at (SEQ. ID. No. 112) | Human | /DB_XREF = DKFZp434B1827_r1 /CLONE = DKFZp434B1827 | ggatttagttgccatgtatcttcagtttcaattttnctttgtcttttcataacat tgactttttttaagagaacagctggtggttttatagaattccatcaatttgggtt tgtcagattattggcttatgattagattcagttatgaattttggcaaggatattg cagaagttatgataggttcttcttagtgcaacttatcacgatacacatgatgtct gtttgtcccattattggtgatgttaacttccgtaacttgctccattgaaa |
| 243003_at (SEQ. ID. No. 113) | Human | /DB_XREF = AV702197 /CLONE = ADBCOH08 | agtattgaaattcctcgagccgctgcttttctcactccataattctggccagaat ttggtacttaaaatattttgtctaaaatattacaatagctacttaagtcatctcc ctgactccactctgttgtctttcagggcgtcgtccacactgtagccaaagtgatc ttataaaaacataattctaatcatggcactcttctgcttaaaaatgttttaatgg ctttccgttaggttaaaatttaaaagtcctttgtagcctgtgagactctacatga gttgactccctagcttcatctttgagcatcttatttctttacttattataccatc agttagagttgattgttatataatccacagaagtgaattctgtccgatttaagc |
| 243185_at (SEQ. ID. No. 114) | Human | /DB_XREF = nz37f07.s1 /CLONE = IMAGE: 1289989 | ttccctccccagtcttagagactgatcactggggcagagtgacattttcccacaa tgctggctcattattttcctcctggaatngcaaatccaagggacaagtggtacag cctgncaccnatccagaaggggagggaatcccaccagaggtgccctgaaacaaag |

TABLE 3-continued

| Probe Set ID | Organism Common Name | Sequence Description | Target Sequence |
|---|---|---|---|
| | | | aanacaagtaacttcaaaaccacatcctaaaatctggacctgtgacaggacagat<br>ggaactctggattgtttgattctatcagcagaacagaggaaggaaatgttttaaa<br>acgagattatgttattttccccagttattatgaagccttcctgaaatgaacttta<br>aatatcggccaccactttcatgaggctgaatgggattcagcaattaggagcgttg<br>cagggaagtgtggcagggcagaggtgggacaaattgcagatccctgtggggtccc<br>ttggttaggtgacaattagtctataaaacacagctgtgtgtgttagggagggagt<br>ggtgtctttaaaaagctctgtgcccaataggaacat |
| 31826_at<br>(SEQ. ID. No. 115) | Human | Cluster Incl.<br>AB014574: *Homo sapiens*<br>mRNA for KIAA0674<br>protein, partial cds<br>/cds =(0,3704)<br>/gb = AB014574<br>/gi = 3327161<br>/ug = Hs.14799<br>/len = 4263 | aaccctgggtctaggcgagccacagggtgaggtcaaggtgagcattctgggaaca<br>atatttgggctcagagggtgggttggccaccttctgagccccacccccgccagac<br>ctggtgaagaggatnnnnnnnnnnnnnnnnnnnnnnnnnnnnannnnnnnnnnnn<br>gttggaagaaggactggtaggttcccctccaagccagtcacctgtaagagtcctg<br>tcctctgccagacttttnnnnnnnnnnnnnnnnnnnnnnnnnnnnnnnnnagccc<br>tcntnnacctgaatccagtgctcaactgtgccccggcaacaagacctgggctgag<br>gtctccctggtagaacnnnnnnnnnnnnnnnnnnnnnnnatcccagtgcagtcaac<br>agcctggcctatagtcctgggacatgtatcttcttctttgccttaaatctgatac<br>aagaggtcaat |
| 35150_at<br>(SEQ. ID. No. 116) | Human | Cluster Incl.<br>X60592: Human CDw40<br>mRNA for nerve growth<br>factor receptor-<br>related B-lymphocyte<br>activation molecule<br>/cds = (47,880)<br>/gb = X60592<br>/gi = 29850<br>/ug = Hs.25648<br>/len = 1004 | cactgtacgagtgaggcctgtgagagctgtgtcctgcaccgctcatgctcgcccg<br>gctttggggtcaagcagattgctacaggggtttctgataccatctgcgagccctg<br>cccagtcggcttcttctccaatgtgtcatctgctttcgaaaaatgtcacccttgg<br>acaannnnnnnnnnnnnnnnnnnnnnnnnnnnnnnnnnnnnggcacaaacaagactg<br>atgttgtctgtggtccccaggntcggctgagagccctggtggtgatccccatcat<br>cttcgggntcctgtttgccatcctcttggtgct |
| 64474_g_at<br>(SEQ. ID. No. 117) | Human | Cluster Incl.<br>AA203219: zx56d02.r1<br>*Homo sapiens* cDNA,<br>5′ end<br>/clone = IMAGE-446499<br>/clone_end = 5′<br>/gb = AA203219<br>/g1 = 1799058<br>/ug = Hs.59457<br>/len = 901 | ccatctgaagcaagagtccagcgttctgccgtgtctgtcccccaccatgcccccct<br>acaggcnnnnnnnnnnnnnnttttttttttttctgtcnnnaannnaannnnnn<br>cntgtgggccgcccacaacatatccttccctcactacctgtgtgaccaaggttgg<br>cttctgttgacctttaaaaaagaaaccctcaactcaaattgctataattagacac<br>ttgcttctgtcttgcntcctgtctgcagctgtgaatagtcatttgactgtgactg<br>ttgcccttagccagccagatgcgcctgtgaaccaaagcttcgtgcacatgtgttc<br>ccctaaaggttggggagcctcgctgtgtcttgctgttcccaggcaccaccacagc<br>agntgnngccatactcttgtggtctctgtgcg |
| 91617_at<br>(SEQ. ID. No. 118) | Human | Cluster Incl.<br>A1028241: ow01b03.x1<br>*Homo sapiens* cDNA, 3′<br>end<br>/clone = IMAGE-1645517<br>/clone_end = 3′<br>/gb = A1028241<br>/gi = 3245550<br>/ug = Hs.59457<br>/len = 752 | tttctgtcaggaaaacaatgttggcctgtgggccgcccacaacatatccttccct<br>cactacctgtgtgaccaaggttggcttctgttgacctttaaaaaagaaaccctca<br>actcaaattgctataattagacacttgcttctgtcttgcctcctgtctgcagctg<br>tgaatagtcatttgactgtgactgttgcccttagccagccagatgcgcctgtgaa<br>ccaaagcttcgtgcacatgtgttccccctaaaggttggggagcctcgctgtgtctt<br>gctgttcccaggcaccaccacagcaggtgctgccatactcttgtggtctctgtgc<br>gcccccccccccccnnnacccgtctgccaagcatgggtatgaatcgtgcacacag<br>ccatgcttcaaggccggggcaggggagcctgtgctgatgccatccagngcactgg<br>gctgtgcctggaaggcgagccttgattgtctgaacacataaagcaaactgtccag |

The invention claimed is:

1. A diagnostic kit containing a microarray, the microarray comprising the nucleotide sequences of SEQ ID NO.:1 to 118 attached to a substrate, the nucleotide sequences corresponding to the predictive genes of a gene expression profile obtained by a method for providing a gene expression profile being predictive for the specific response of an individual tumor to Avastin, the method comprising the steps of:

(a) xenotransplanting human tumor material of at least five different tumors into at least one suitable test animal, (b) determining gene expression profiles of the resulting tumor xenografts, (c) treating said at least one test animal with Avastin, (d) evaluating responsiveness of the tumor xenografts to Avastin, (e) identifying the gene expression profile of each of the tested tumor xenografts, and (f) determining the predictive genes in the gene expression profiles by comparing the gene expression profiles of responsive tumors, no-change tumors and progressive tumors, wherein step (f) comprises the steps of (i) dividing the complete set of gene expression profiles of the tumor xenografts into sub-sets, each of the sub-sets missing one of said gene expression profiles, (ii) determining the predictive genes in each sub-set, and (iii) obtaining the gene expression profile being predictive for the specific response of an individual tumor to Avastin by setting up the intersection of the predictive genes of all sub-sets.

2. The kit according to claim 1, wherein in step (f) a tumor xenograft is considered to be responsive when its T/C (therapy/control) value is less than 25%.

3. The kit according to claim 1, wherein in step (f) a tumor xenograft is considered to be no-change when its T/C (therapy/control) value is ranges from 25% to 42%.

4. The kit according to claim 1, wherein in step (f) a tumor xenograft is considered to be progressive when its T/C (therapy/control) value is more than 42%.

5. The kit according to claim 1, wherein in step (ii) an expression profile of 300 genes is determined for each subset.

* * * * *